(12) United States Patent
Dowdy et al.

(10) Patent No.: US 9,260,493 B2
(45) Date of Patent: Feb. 16, 2016

(54) TRANSDUCIBLE DELIVERY OF NUCLEIC ACIDS USING MODIFIED DSRNA BINDING DOMAINS

(75) Inventors: Steven F. Dowdy, La Jolla, CA (US); Akiko Eguchi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 376 days.

(21) Appl. No.: 13/319,326

(22) PCT Filed: May 7, 2010

(86) PCT No.: PCT/US2010/034013
§ 371 (c)(1),
(2), (4) Date: Nov. 7, 2011

(87) PCT Pub. No.: WO2010/129853
PCT Pub. Date: Nov. 11, 2010

(65) Prior Publication Data
US 2012/0101045 A1    Apr. 26, 2012

Related U.S. Application Data

(60) Provisional application No. 61/176,326, filed on May 7, 2009.

(51) Int. Cl.
*C07K 14/47* (2006.01)
*C12N 15/11* (2006.01)
*C12N 15/87* (2006.01)

(52) U.S. Cl.
CPC .............. *C07K 14/47* (2013.01); *C12N 15/111* (2013.01); *C12N 15/87* (2013.01); *C07K 2319/80* (2013.01); *C07K 2319/85* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| 4,888,278 | A | 12/1989 | Singer et al. |
| 6,468,986 | B1 | 10/2002 | Zuckermann et al. |
| 2005/0147993 | A1 | 7/2005 | Khan |
| 2009/0093026 | A1 | 4/2009 | Dowdy et al. |

FOREIGN PATENT DOCUMENTS

| WO | 00/40723 | A2 | 7/2000 |
| WO | 2004/007721 | A1 | 1/2004 |
| WO | 2004/048545 | A2 | 6/2004 |
| WO | 2008/008476 | A2 | 1/2006 |

OTHER PUBLICATIONS

Shan et al ('A small molecule enhances RNA interference and promotes microRNA processing' v26(8) Aug. 2008 pp. 933-940).*
Romano et al ('Autophosphorylation in the activation loop is required for full kinase activity in vivo of human and yeast eukaryotic initiation factor 2alpha kinases PKR and GCN2' Molecular and Cellular Biology Apr. 1998 pp. 2282-2297).*
PKR NCBI entry (retrieved from http://www.ncbi.nlm.nih.gov/protein/AAA36409 on Jan. 13, 2014, 2 pages).*
Laurila et al ('A protein-protein interaction guided method for competitive transcription factor binding improves target predictions' Nucleic Acids Research v37(22) 2009 e146 pp. 1-11).*
Russell lab ('Histidine' entry retrieved from http://www.russelllab.org/aas/His.html on Jun. 24, 2014, 4 pages).*
Gerlt et al (Can sequence determine function? Genome Biology v1(5) 2000 pp. 1-10).*
Garcia et al ('Impact of Protein kinase PKR in cell biology:from antiviral to antiproliferative action' Microbiology and molecular biology reviews v70(4) Dec. 2006 pp. 1032-1060).*
Protein calculator v3.4 (retrieved from http://protcalc.sourceforge.net/cgi-bin/protcalc on May 4, 2015, 2 pages).*
UIC (retrieved from http://tigger.uic.edu/classes/phys/phys461/phys450/ANJUM04/ on May 5, 2015, 12 pages).*
Chauhan et al., "PTD-Fusion Peptide as a Delivery Vehicle for SiRNA to Target HIV Reservoirs", Molecular Therapy, Academic Press, San Diego, CA, US, Jan. 1, 2006, vol. 13., p. S277.
Grotzinger, Thilo, Supplementary European Search Report, Date of Completion of Search: Jan. 26, 2010, Application Number: EP07750474.
Choi, Joong Hwan, International Search Report and Written Opinion, PCT/US2010/034013, Korean Intellectual Property Office, Mar. 17, 2011.

\* cited by examiner

*Primary Examiner* — Karlheinz R Skowronek
*Assistant Examiner* — Ronald Niebauer
(74) *Attorney, Agent, or Firm* — Joseph R. Baker, Jr.; Gavrilovich, Dodd & Lindsey LLP

(57) ABSTRACT

The disclosure provides fusion polypeptides and constructs useful in delivering anionically charged nucleic acid molecules including diagnostics and therapeutics to a cell or subject. The fusion constructs include a protein transduction domain and a nucleic acid binding domain, or a protein transduction domain and a nucleic acid that is coated with one or more nucleic acid binding domains sufficient to neutralize an anionic charge on the nucleic acid. Also provided are methods of treating disease and disorders such as cell proliferative disorders.

12 Claims, 28 Drawing Sheets

TRANSDUCIBLE DELIVERY OF NUCLEIC ACIDS USING MODIFIED DSRNA BINDING DOMAINS

CROSS REFERENCE TO RELATED APPLICATIONS

This application is a U.S. National Stage Application, filed under 35 U.S.C. §371 and claims priority to International Application No. PCT/US10/34013, filed May 7, 2010, which application claims priority to U.S. Provisional Application Ser. No. 61/176,326 filed May 7, 2009, the disclosures of which are incorporated herein by reference.

TECHNICAL FIELD

This invention relates to compositions and methods for transducing cells.

BACKGROUND

The discovery of RNA interference (RNAi) as a cellular mechanism that selectively degrades mRNAs allows for both the targeted manipulation of cellular phenotypes in cell culture and the potential for development of directed therapeutics (Behlke, Mol. Ther. 13, 644-670, 2006; Xie et al., Drug Discov. Today 11, 67-73, 2006). Although short interfering RNA's (siRNAs) have great potential for manipulation of cellular phenotypes, due to their size and negative (anionic) charged nature, siRNAs are macromolecules with no ability to enter cells. Indeed, siRNAs are 25× in excess of Lipinski's "Rule of 5s" for cellular delivery of membrane diffusible molecules that generally limits size to less than 500 Da. Consequently, in the absence of a delivery vehicle or transfection agent, naked siRNAs do not enter cells, even at millimolar concentrations (Barquinero et al., Gene Ther. 11 Suppl 1, S3-9, 2004). Significant attention has been focused on the use of cationic lipids that both condense the siRNA and punch holes in the cellular membrane to solve the siRNA delivery problem. Although widely used, transfection reagents fail to achieve efficient delivery into many cell types, especially primary cells and hematopoietic cell lineages (T and B cells, macrophage). Moreover, lipofection reagents often result in varying degrees of cytotoxicity ranging from mild in tumor cells to high in primary cells.

SUMMARY mRNA degradation by short interfering RNA (siRNA) induced RNA interference (RNAi) responses allows for selective manipulation of cellular phenotypes for discovery research and potentially RNAi based therapeutics to treat cancer and viral diseases. However, due to their size (~14,000 Dalton) and extensive anionic charge, siRNAs have no bioavailability to enter unperturbed cells. Current siRNA delivery approaches fail to deliver siRNAs into a high percentage of cells in a non-cytotoxic fashion, especially primary cells. Peptide Transduction Domain-dsRNA Binding Domain (PTD-DRBD) fusion protein siRNA delivery approach have been described. DRBDs bind siRNAs with high avidity (KD ~$10^{-9}$) independent of sequence, mask the siRNA negative charge and allow for PTD-mediated cellular uptake. PTD-DRBD delivered siRNAs induced RNAi responses in the entire cell population of 20+ cell types assayed in a non-cytotoxic fashion, including primary HUVEC, fibroblasts, keratinocytes, hematopoietic lineages and human embryonic stem cells. PTD-DRBD mediated siRNA delivery into cells occurs by a specialized form of fluid phase endocytosis, termed macropinocytosis. However, due to strong DRBD binding to the siRNA, DRBD release of siRNA into the lumen of the macropinosome limits siRNA escape into the cytoplasm. During endocytotic maturation, the pH of the macropinosome vesicle decreases to ~5. The disclosure demonstrates a pH dependency of PTD-DRBD binding to siRNA and a pH-dependent siRNA release from PTD-DRBD starting at pH 6 that increased further at pH 5. In an attempt to enhance the pH-dependent siRNA release, Histidine pair (pKa ~6.5) mutations were introduced into the non-conserved, non-RNA contact, backbone DRBD structure. Four of 12 Histidine mutants generated resulted in dramatic increases in RNAi responses inside cells. The disclosure demonstrates that the introduction of pH sensitive Histidine pairs in the DRBD structure resulted in a significant enhancement of PTD-DRBD mediated siRNA induced cellular RNAi responses. These new PTD-DRBD versions have the potential to dramatically enhance systemic in vivo RNAi therapeutics responses.

The disclosure provides a modified nucleic acid binding protein (mDRBD) comprising amino acid substitutions that increase the cationic charge of the polypeptide, while maintaining nucleic acid binding capacity. In one embodiment, the substitution comprises an amino acid selected from Histidine (H), Arginine (R) and Lysine (K). In one embodiment, the disclosure provides a substantially purified polypeptide comprising (i) from about 60-90 amino acids, (ii) two or more histidine amino acid substitutions compared to a nucleic acid binding polypeptide selected from the group consisting of histone, protamine, PKR (having accession no. AAA36409, AAA61926, Q03963), TRBP (having accession no. P97473, AAA36765), PACT (having accession no. AAC25672, AAA49947, NP609646), Staufen (having accession no. AAD17531, AAF98119, AAD17529, P25159), NFAR1 (having accession no. AF167569), NFAR2 (having accession no. AF167570, AAF31446, AAC71052, AAA19960, AAA19961, AAG22859), SPNR (having accession no. AAK20832, AAF59924, A57284), RHA (having accession no. CAA71668, AAC05725, AAF57297), NREBP (having accession no. AAK07692, AAF23120, AAF54409, T33856), kanadaptin (having accession no. AAK29177, AAB88191, AAF55582, NP499172, NP198700, BAB19354), HYL1 (having accession no. NP563850), hyponastic leaves (having accession no. CAC05659, BAB00641), ADAR1 (having accession no. AAB97118, P55266, AAK16102, AAB51687, AF051275), ADAR2 (having accession no. P78563, P51400, AAK17102, AAF63702), ADAR3 (having accession no. AAF78094, AAB41862, AAF76894), TENR (having accession no. XP059592, CAA59168), RNaseIII (having accession no. AAF80558, AAF59169, Z81070Q02555/S55784, PO5797), and Dicer (having accession no. BAA78691, AF408401, AAF56056, S44849, AAF03534, Q9884), RDE-4 (having accession no. AY071926), FLJ20399 (having accession no. NP060273, BAB26260), CG1434 (having accession no. AAF48360, EAA12065, CAA21662), CG13139 (having accession no. XP059208, XP143416, XP110450, AAF52926, EEA14824), DGCRK6 (having accession no. BAB83032, XP110167) CG1800 (AAF57175, EAA08039), FLJ20036 (having accession no. AAH22270, XP134159), MRP-L45 (having accession no. BAB14234, XP129893), CG2109 (having accession no. AAF52025), CG12493 (having accession no. NP647927), CG10630 (having accession no. AAF50777), CG17686 (AAD50502), T22A3.5 (having accession no. CAB03384) and Accession number EAA14308, and (iii) the ability to bind an anionic nucleic acid molecule to form a complex with a net cationic charge. In yet another embodiment, the polypeptide has the consensus sequence of SEQ ID NO:1, wherein at least 2 histidines are present in the sequence and wherein the histidines are at residues selected from the group consisting of residue 16, 18, 19, 20, 37, 38, 44, 46, 57 and 58. In a further embodiment, the histidines are immediately adjacent. In yet another embodiment, the histidines are separated by 1, 2 or 3 amino acid residues. In one embodiment, the polypeptide has the consensus sequence of SEQ ID NO:1, and which comprises a plurality of histidines at the N- or C-terminus. In a further embodiment, the plurality of histidines comprise from about 2-12 histidines.

The disclosure also provides a composition comprising a nucleic acid binding polypeptide comprising non-conservative substitutions of histidine to increase the cationic charge of the polypeptide compared to a wild-type nucleic acid binding polypeptide having a sequence as set forth in SEQ ID NO:7 and wherein the polypeptide is in complex with an anionically charged nucleic acid to form a nucleic acid binding protein-nucleic acid complex having a net cationic charge.

In yet another embodiment, the modified DRBD further comprises a protein transduction domain (PTD) linked to the anionically charged nucleic acid or the polypeptide (mDRBD). In one embodiment, the nucleic acid binding protein comprises SEQ ID NO:1 wherein at least 2 histidines are present in the sequence and wherein the histidines are at residues selected from the group consisting of residue 16, 18, 19, 20, 37, 38, 44, 46, 57 and 58 and/or wherein the polypeptide of SEQ ID NO:1 comprises a poly histidine tail.

In some embodiments, the polypeptide (mDRBD) comprises a sequence selected from the group consisting of: (a) ffmeelntyrqkqgvvlkyqelpnsgp-phdrrftfqviidgrefpegegrskkeaknaaaklaveilnke (SEQ ID NO:2), wherein at least 2 histidines are present in the sequence at a position selected from residues selected from the group consisting of 16, 18, 19, 20, 37, 38, 44, 46, 57 and 58; (b) ffmeelntyrqkqgvhlkyqelpnsgp-phdrrftfqviidgrefpegegrskkeaknaaaklaveilnke (SEQ ID NO:3); (c) ffmeelntyrqkqgvvlkyqelpnsgp-phdrrftfqviidgrefpegegr-skkeaknaaaklaveilnkehhhhhhhhhhhh (SEQ ID NO:4); (d) ffmeelntyrqkqgvvlkyqelpnsgp-phdrrftfqviidgrehphgegrskkeaknaaaklaveilnke (SEQ ID NO:5); and (e) ffmeelntyrqkqgvvlkyqelpnsgp-phdrrftfqviidgrefpegegrskkeakhhaaklaveilnke (SEQ ID NO:6). In yet another embodiment, the modified DRBD is derived from a polypeptide comprising a sequence set forth selected from the group of sequences set forth in the following accession numbers (Accession numbers in parenthesis): PKR (AAA36409, AAA61926, Q03963), TRBP (P97473, AAA36765), PACT (AAC25672, AAA49947, NP609646), Staufen (AAD17531, AAF98119, AAD17529, P25159), NFAR1 (AF167569), NFAR2 (AF167570, AAF31446, AAC71052, AAA19960, AAA19961, AAG22859), SPNR (AAK20832, AAF59924, A57284), RHA (CAA71668, AAC05725, AAF57297), NREBP (AAK07692, AAF23120, AAF54409, T33856), kanadaptin (AAK29177, AAB88191, AAF55582, NP499172, NP198700, BAB19354), HYL1 (NP563850), hyponastic leaves (CAC05659, BAB00641), ADAR1 (AAB97118, P55266, AAK16102, AAB51687, AF051275), ADAR2 P78563, P51400, AAK17102, AAF63702), ADAR3 (AAF78094, AAB41862, AAF76894), TENR(XP059592, CAA59168), RNaseIII (AAF80558, AAF59169, Z81070Q02555/S55784, PO5797), and Dicer (BAA78691, AF408401, AAF56056, S44849, AAF03534, Q9884), RDE-4 (AY071926), FLJ20399 (NP060273, BAB26260), CG1434 (AAF48360, EAA12065, CAA21662), CG13139 (XP059208, XP143416, XP110450, AAF52926, EEA14824), DGCRK6 (BAB83032, XP110167) CG1800 (AAF57175, EAA08039), FLJ20036 (AAH22270, XP134159), MRP-L45 (BAB14234, XP129893), CG2109 (AAF52025), CG12493 (NP647927), CG10630 (AAF50777), CG17686 (AAD50502), T22A3.5 (CAB03384) and Accession number EAA14308. In yet another embodiment, the nucleic acid comprises a dsRNA. In yet another embodiment, the PTD is operably linked to the nucleic acid binding polypeptide. In yet another embodiment, the PTD is operably linked to the nucleic acid. In one embodiment, the ratio of nucleic acid binding polypeptide to nucleic acid is 1:1. In yet another embodiment, the ratio of nucleic acid binding polypeptide to nucleic acid is 2:1. The PTD can be selected from the group consisting of a polypeptide comprising a herpesviral VP22 protein; a polypeptide comprising a human immunodeficiency virus (HIV) TAT protein; a polypeptide comprising a homeodomain of an Antennapedia protein (Antp HD), and functional fragments thereof.

The disclosure also provides a method of introducing an anionically charged nucleic acid molecule into a cell comprising contacting the cell with a composition of the disclosure comprising a mDRBD or of fusion construct with a PTD in complex with the nucleic acid molecule. In one embodiment, the nucleic acid is a dsRNA or siRNA The disclosure also provides a method of inhibiting expression of a target nucleic acid in a cell or subject comprising contacting the cell or subject with an inhibitory RNA molecule in complex with an mDRBD of the disclosure. In a further embodiment, the complex is operably linked to a protein transduction domain. In one embodiment, the target nucleic acid is a nucleic acid that promotes a cancerous phenotype.

DETAILED DESCRIPTION

Figure 1:
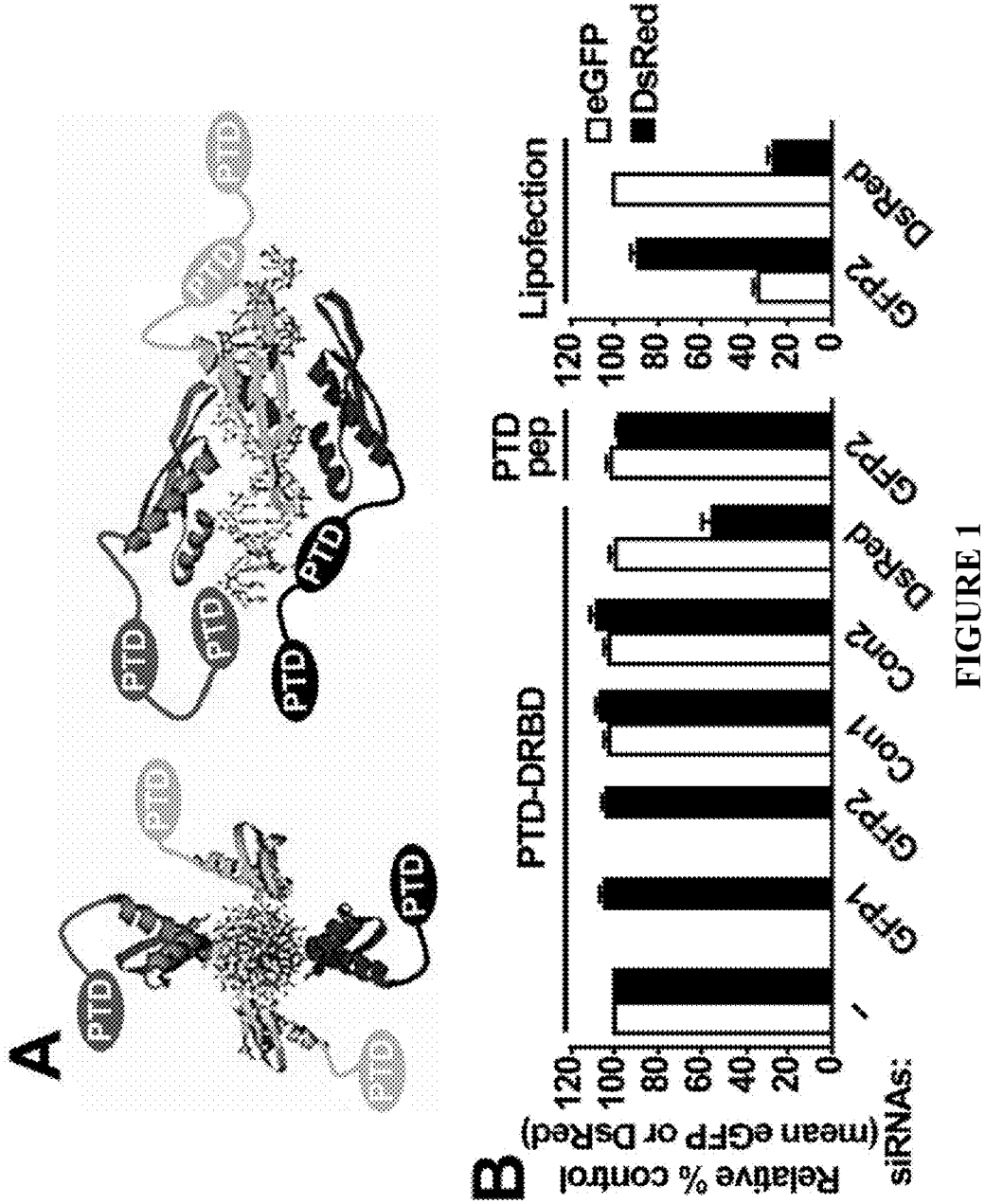
FIG. 1A-J shows PTD-DRBD Mediated siRNA Delivery. (a) Hypothetical cartoon of PTD-DRBD bound to siRNA. DRBD Ribbon structure derived from Ryter and Schultze13 (b) Normalized RNAi knockdown of dGFP and dDsRed by PTD-DRBD:siRNA (left panel) and lipofection (right panel), as indicated, in H1299 dGFP/dDsRed cells. Mean values were normalized to percent control. (c,d) Single cell flow cytometry histogram analysis of dGFP RNAi response at 1 and 2 days post-treatment of H1299 dGFP/dDsRed cells, as indicated. (e) Flow cytometry analysis of dGFP RNAi knockdown decay kinetics following a single siRNA treatment of dividing H1299 dGFP/dDsRed cells. (f) Flow cytometry analysis of dGFP RNAi knockdown decay kinetics following multiple siRNA treatments of H1299 dGFP cells, as indicated. Mean values are normalized to percent control. (g,h) Quantitative RT-PCR analysis of endogenous GAPDH mRNA expression at 6 and 12 h post-treatment in H1299 cells, as indicated. Mean values normalized to β2 microglobulin and reported as percent of mock GAPDH control. **($P<0.001$) and *($P<0.005$) of specific siRNA delivered by PTD-DRBD compared to lipofection. (i,j) Whole genome microarray profile M-A plot of GAPDH siRNA delivered by PTD-DRBD (i) or Lipofection (j) at 12 and 24 h post-treatment in H1299 cells, as indicated. Blue line indicates 1.6× fold up/down change.
Figure 1:
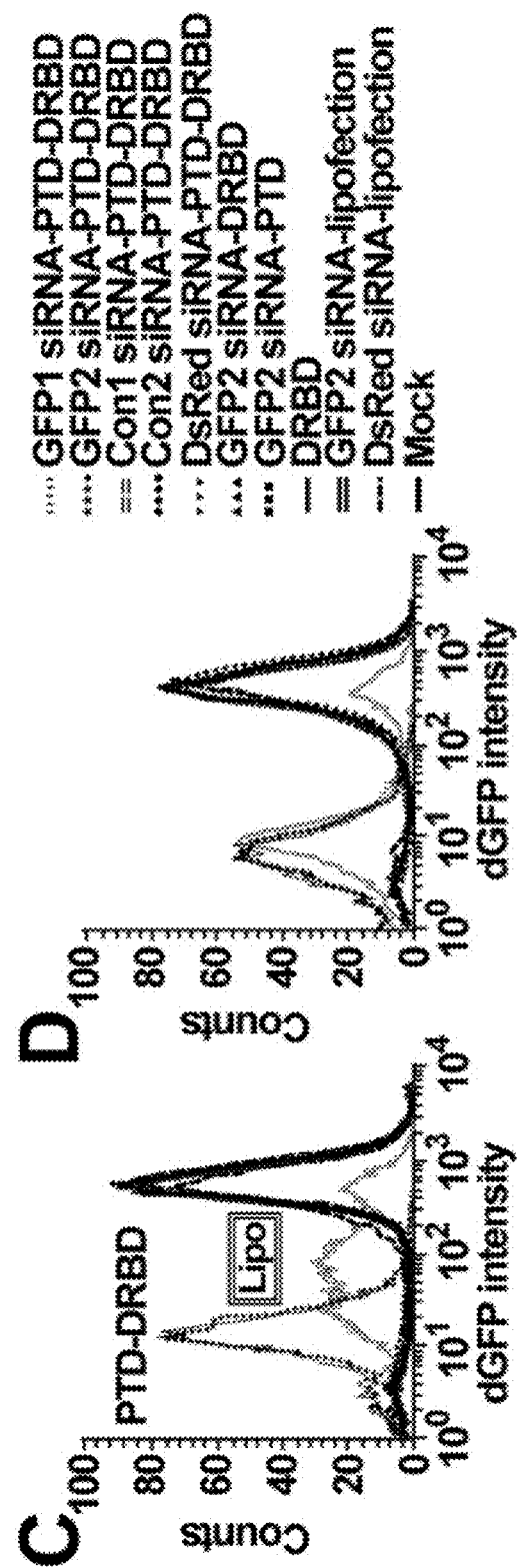
Figure 1:
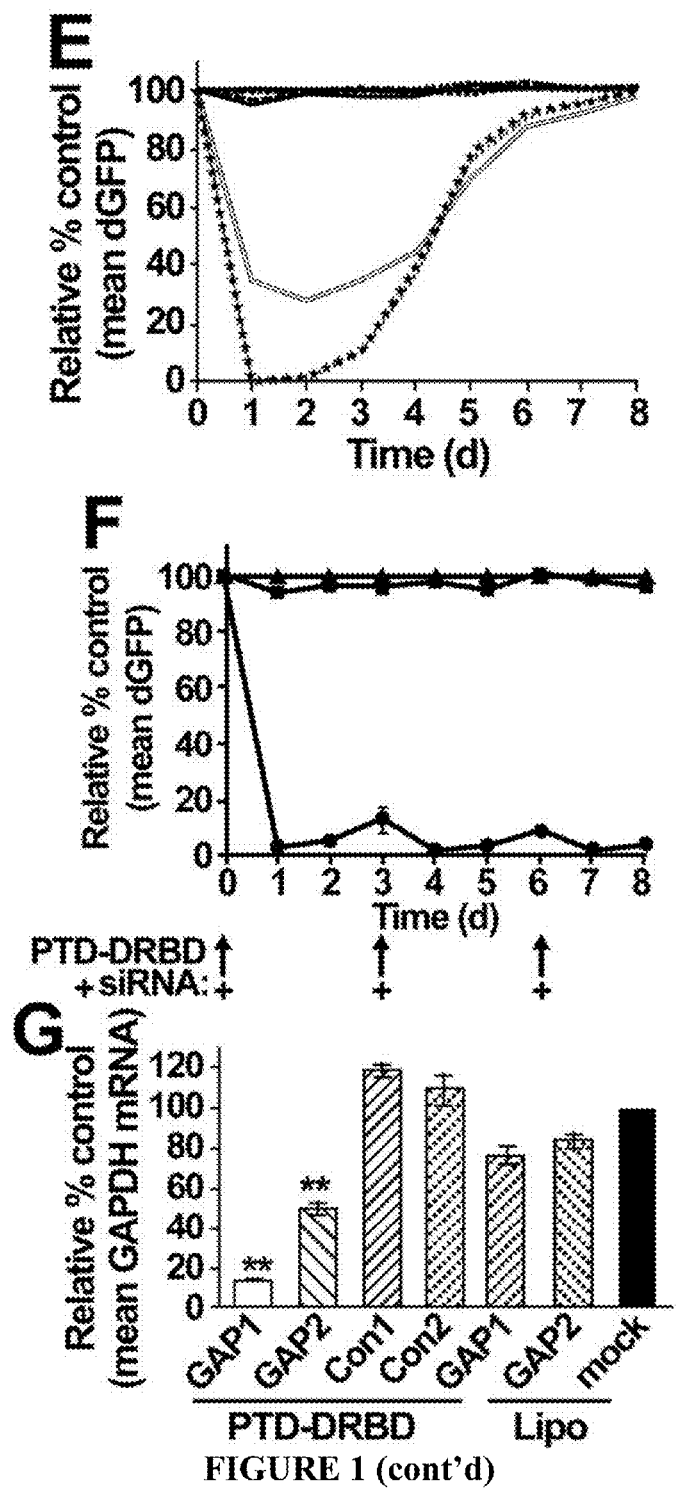
Figure 1:
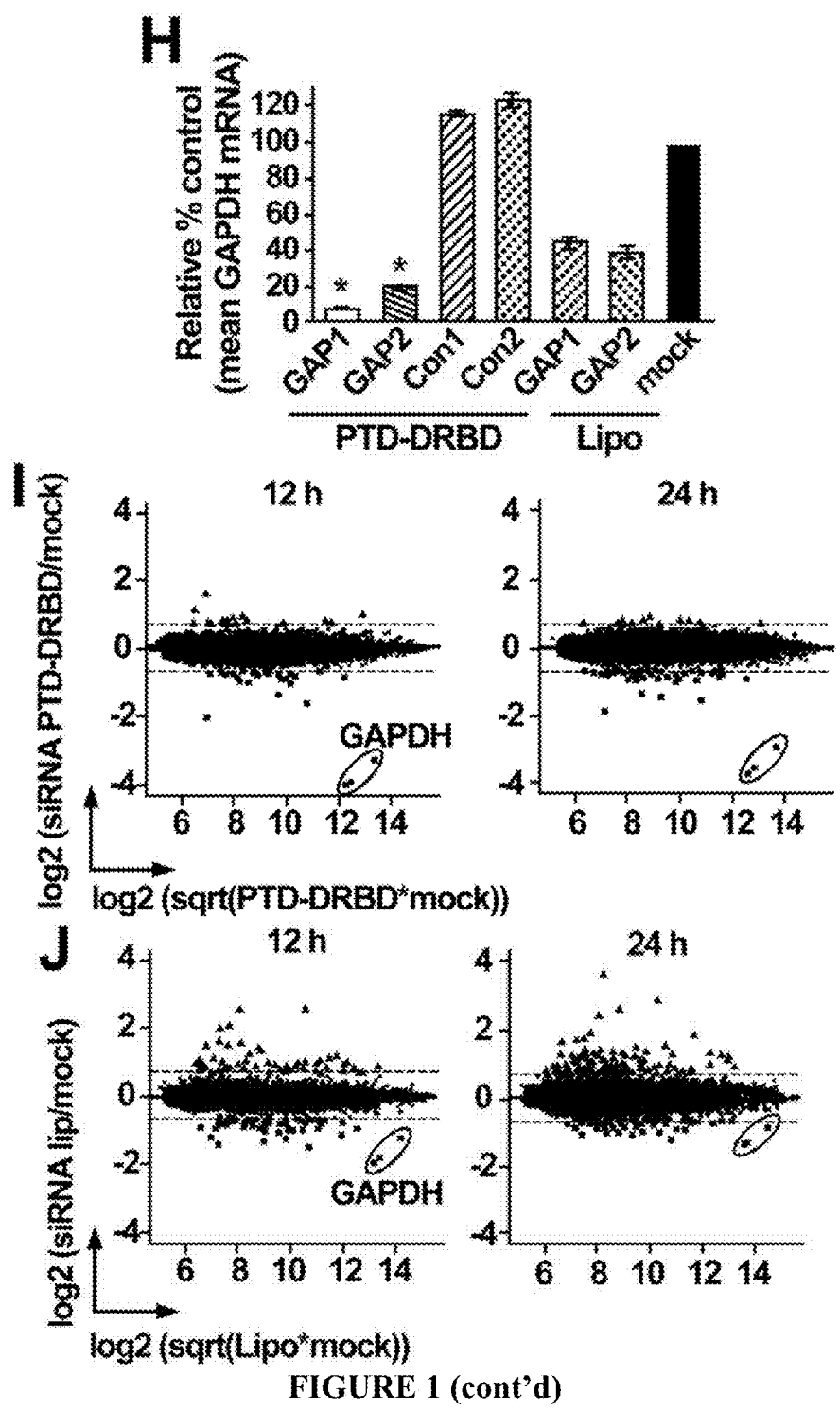

As used herein and in the appended claims, the singular forms "a," "and," and "the" include plural referents unless the context clearly dictates otherwise. Thus, for example, reference to "a PTD" includes a plurality of such PTDs and reference to "the cell" includes reference to one or more cells known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of:"

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

dsRNA binding proteins (DRBPs) include a family of eukaryotic, prokaryotic, and viral-encoded protein molecules that share a common conserved motif that facilitates interaction with dsRNA. Proteins containing dsRNA binding domains (DRBDs) have been shown to contain motifs that interact with as little as 11 bp of sequence independent dsRNA. More than 20 DRBPs have been identified. Examples include the dsRNA-dependent protein kinase PKR that functions in dsRNA signaling and host defense against virus infection and DICER, which is implicated in RNA interference (RNAi)-mediated gene silencing. The dsRNA binding protein contain an evolutionarily conserved dsRNA binding domain (DRBD) of about 65-68 amino acids. Eukaryotic dsRNA binding proteins can contain up to five DRBDs, while other DRBPs, such as viral DRBPs, usually contain only one.

The disclosure provides a modified dsRNA binding domain (mDRBD) that comprises improved RNA oligonucleotide release from a micropinosome. An mDRBD of the disclosure can be derived from any number of dsRNA binding proteins known in the art. A DRBD can be cloned and modified using techniques known in the art. An mDRBD of the disclosure comprises a consensus sequence: X(F/Y)XXX(L/I)NX(Y/I)XQKXX(V/L)X(L/V) XYXXXXXXGXXXXXXFX(F/Y)XXX(I/M)X X(R/K)E (F/Y)XXGXGX(S/T)KXEAK(N/Q)XAAKLA(V/Y)XX(L/I)XXE (SEQ ID NO:1), wherein at least 2 histidines are present in the sequence, wherein the histidines are at residues selected from the group consisting of 16, 18, 19, 20, 37, 38, 44, 46, 57 and 58. In one embodiment, the histidines are immediately adjacent. In another embodiment, the histidines are separated by 1, 2 or 3 amino acid residues. In yet another embodiment, the mDRBD of the disclosure comprises SEQ ID NO:1 with a plurality of histidines at the C-terminus. In a specific embodiment, the plurality of histidines comprise from about 2-12 histidines.

The disclosure also provides a mDRBD comprises a sequence ffmeelntyrqkqgvvlkyqelpnsgp-phdrrftfqviidgrefpegegrskkeaknaaaklaveilnke (SEQ ID NO:2), wherein at least 2 histidines are present in the sequence and wherein the histidines are substituted at residues selected from the group consisting of 16, 18, 19, 20, 37, 38, 44, 46, 57 and 58. In one embodiment, the histidines are immediately adjacent. In another embodiment, the histidines are separated by 1, 2 or 3 amino acid residues. In yet another embodiment, the mDRBD of the disclosure comprises (SEQ ID NO:1) with a plurality of histidines at the C-terminus. In yet further embodiments, the disclosure provides a mDRBD comprising a sequence selected from the group consisting of (a) ffmeelntyrqkqgvhlhyqelpnsgp-phdrrftfqviidgrefpegegrskkeaknaaaklaveilnke (SEQ ID NO:3); (b) ffmeelntyrqkqgvvlkyqelpnsgp-phdrrftfqviidgrefpegegr-skkeaknaaaklaveilnkehhhhhhhhhhhh (SEQ ID NO:4); (c) ffmeelntyrqkqgvvlkyqelpnsgp-phdrrftfqviidgrehphgegrskkeaknaaaklaveilnke (SEQ ID NO:5); and (d) ffmeelntyrqkqgvvlkyqelpnsgp-phdrrftfqviidgrefpegegrskkeakhhaaklaveilnke (SEQ ID NO:6).

The methods and compositions of the disclosure reversibly mask or neutralize the charge on a nucleic acid (e.g., dsRNA). The disclosure utilizes nucleic acid binding proteins that mask the anionic charge of the nucleic acid while maintaining a cationic charge necessary for traversal of the cellular membrane, thus permitting the cationic activity of the PTD to traverse the cell membrane and transduce a cell. The nucleic acid binding protein is however modified from the wild type sequence with two or more histidines to assist in release of the dsRNA from the micropinosomes. For examples, the extra histidines provide a proton-sponge effect that results in increases swelling and subsequent bursting of the micropinosome.

The mDRBD polypeptides above may be chemically synthesized or recombinantly generated using techniques known in the art. The disclosure also provides polynucleotides encoding the mDRBD polypeptides described herein. One of skill in the art can generate a polynucleotide encoding a mDRBD of the disclosure using available codon charts and taking into account the degeneracy of the genetic code.

The ability to deliver functional agents to cells is problematical due to the bioavailability restriction imposed by the cell membrane. That is, the plasma membrane of the cell forms an effective barrier, which restricts the intracellular uptake of molecules to those which are sufficiently non-polar and smaller than approximately 500 daltons in size. Previous efforts to enhance the internalization of proteins have focused on fusing proteins with receptor ligands (Ng et al., Proc. Natl. Acad. Sci. USA, 99:10706-11, 2002) or by packaging them into caged liposomal carriers (Abu-Amer et al., J. Biol. Chem. 276:30499-503, 2001). However, these techniques often result in poor cellular uptake and intracellular sequestration into the endocytic pathway.

The mDRBD polypeptides are useful in reducing the charge of RNA oligonucleotides to promote transport across the cell membrane and release from micropinosomes in the cytoplasm.

The disclosure provides methods and compositions useful for intracellular delivery of nucleic acids which are otherwise difficult to transfect and where microinjection is not a possible option. For instance, primary lymphocytes are very difficult to transfect, requiring electroporation of DNA constructs. This process is very inefficient, killing 90-99% of the cells, and yielding therapeutic results in less than 10% of those which survive.

The disclosure also provides fusion polypeptides and compositions useful in cellular transduction and cellular modulation. The fusion polypeptides of the disclosure comprise a transduction moiety/domain comprising a membrane transport function and a mDRBD to reversibly neutralize anionic charges on nucleic acids. In a further embodiment, the fusion polypeptides of the disclosure comprise an anionic nucleic acid molecules (e.g., dsRNA) that is capable of interacting with the nucleic acid binding domain.

Using the compositions of the disclosure various diseases and disorders can be treated. For example, growth of tumor cells can be inhibited, suppressed, or destroyed upon delivery of an anti-tumor siRNA. For example, an anti-tumor siRNA can be an siRNA targeted to a gene encoding a polypeptide that promotes angiogenesis. Various angiogenic proteins associated with tumor growth are known in the art.

It is to be understood that the disclosure is not to be limited to any particular nucleic acid binding domain or nucleic acid domain. Rather, the nucleic acid domain can be any nucleic acid binding domain capable of reversibly neutralizing or reducing the anionic charge of a nucleic acid binding domain to be delivered. Furthermore, any anionically charged nucleic acid (e.g., dsRNA, siRNA and the like) can be delivered using the methods and compositions described herein.

The disclosure provides compositions and methods for delivering anionically charged nucleic acids (RNA, DNA, nucleic acids comprising modified bases and the like). The disclosure provides methods and compositions useful for delivery of interfering RNA agents.

RNA interference (RNAi) is the process whereby messenger RNA (mRNA) is degraded by small interfering RNA (siRNA) derived from double-stranded RNA (dsRNA) containing an identical or very similar nucleotide sequence to that of a target gene to be silenced. This process prevents the production of a protein encoded by the targeted gene through post-transcriptional, pre-translational manipulation. Accordingly, silencing of dominant disease genes or other target genes can be accomplished.

RNAi proceeds by a process in which the dsRNA is cleaved into short interfering RNAs (siRNAs) by an enzyme called Dicer, a dsRNA endoribonuclease, (Bernstein et al., 2001; Hamilton & Baulcombe, 1999, Science 286: 950; Meister and Tuschl, 2004, Nature 431, 343-9), thus producing multiple molecules from the original single dsRNA. siRNAs are loaded into the multimeric RNAi Silencing Complex (RISC) resulting in both catalytic activation and mRNA target specificity (Hannon and Rossi, Nature 431, 371-378, 2004; Novina and Sharp, Nature 430, 161-164, 2004). During siRNA loading into RISC, the antisense or guide strand is separated from the siRNA and remains docked in Argonaute-2 (Ago2), the RISC catalytic subunit (Leuschner et al., EMBO Rep. 7, 314-320, 2006). mRNAs exported from the nucleus into the cytoplasm are thought to pass through activated RISCs prior to ribosomal arrival, thereby allowing for directed, post-transcriptional, pre-translational regulation of gene expression. In theory, each and every cellular mRNA can be regulated by induction of a selective RNAi response.

The ability of 21-23 bp siRNAs to efficiently induce an RNAi response in mammalian cells is now routine (Sontheimer, Nat. Rev. Mol. Cell. Biol. 6, 127-138, 2005). The 50% Inhibitory Concentration ($IC_{50}$) for siRNAs is in the 10-100 pM range, significantly below the best drugs with $IC_{50}$s in the 1-10 nM range. Consequently, due to its exquisite selectivity, RNAi has become a corner-stone for directed manipulation of cellular phenotypes, mapping genetic pathways, discovering and validating therapeutic targets, and has significant therapeutic potential.

The most interesting aspects of RNAi include (1) dsRNA, rather than single-stranded antisense RNA, is the interfering agent; (2) the process is highly specific and is remarkably potent (only a few dsRNA molecules per cell are required for effective interference); (3) the interfering activity (and presumably the dsRNA) can cause interference in cells and tissues far removed from the site of introduction. However, effective delivery of dsRNA is difficult. For example, a 21 bp dsRNA with a molecular weight of 13,860 Daltons cannot traverse the cell membrane to enter the cytoplasm, due to (1) the size and (2) the extremely negative (acidic) charge of the RNA.

Macromolecule fusion of "cargo" biological agents to a cationic Peptide Transduction Domain (PTD) (also termed Cell Penetrating Peptide, CPP), such as TAT, 8×Arg, Antp (Snyder and Dowdy, 2005, Expert Opin. Drug Deliv. 2, 43-51) can be used to facilitate uptake of the macromolecule. PTDs can be used to deliver a wide variety of macromolecular cargo, including peptides, proteins, PNAs and DNA vectors into 100% of primary and transformed cells, into most, if not all, tissues. Pre-clinical models comprising PTD's are currently being tested in several clinical trials (Schwarze et al., 1999, Science 285, 1569-1572; Eguchi et al., 2001, J. Biol. Chem. 276, 2620426210; Koppelhus et al., 2002, Antisense Nucleic Acid Drug Dev. 12, 51-63). Cationic PTDs enter cells by macropinocytosis, a specialized form of fluid phase uptake that all cells perform.

Biophysical studies on model vesicles suggests that cargo escape, from macropinosome vesicles into the cytoplasm, requires a pH decrease (Magzoub et al., 2005, Biochemistry 44, 14890-14897). The cationic charge of the PTDs is essential for the molecules to traverse the cell membrane. Not surprisingly, conjugation of cationic PTDs (6-8 positive charges) to anionic siRNAs (~40 negative charges) results in charge neutralization and inactivation of the PTD with no siRNA entering the cells (Turner et al., Blood Cells Mol. Dis., 38(1):1-7, 2007). However, chemical conjugation of cationic TAT to anionic RNA (or DNA) through a reversible disulfide bond results in charge neutralization of the cationic TAT PTD, thus eliminating or reducing the charge necessary to effectively traverse the cell surface and transduce the cell. In addition, due to a vast excess of negative charges on, for example, a 21 bp dsRNA versus the limited number of cationic charges on TAT, any free TAT PTD conjugated to the RNA results in aggregation and precipitation of the peptide-nucleic acid conjugate. Thus, while PTDs offer great potential to deliver macromolecular siRNAs into cells, PTD charge neutralization by the siRNA remains a formidable barrier for utilization of this approach.

The methods and compositions of the disclosure reversibly mask or neutralize the charge on a nucleic acid (e.g., dsRNA). The disclosure utilizes nucleic acid binding proteins that mask the anionic charge of the nucleic acid while maintaining a cationic charge necessary for traversal of the cellular membrane, thus permitting the cationic activity of the PTD to traverse the cell membrane and transduce a cell. The nucleic acid binding protein is however modified from the wild type sequence with two or more histidines to assist in release of the dsRNA from the micropinosomes. For examples, the extra histidines provide a proton-sponge effect that results in increases swelling and subsequent bursting of the micropinosome.

The disclosure provides methods and compositions useful to solve the macromolecular delivery problem of charged naked nucleic acids. To circumvent PTD charge neutralization and solve siRNA delivery problems. One embodiment of the disclosure provides a universal siRNA delivery approach comprising a PTD delivery domain operably linked to a modified dsRNA Binding Domain (DRBD) comprising 2 or more histidines inserted at non-conserved locations to form a PTD-mDRBD construct that binds the siRNA and masks its negative charge.

The mDRBDs of the disclosure bind to siRNAs in a sequence-independent manner that allows for PTD-mDRBD mediated delivery of siRNAs into cells. Using PTD-mDRBD delivery of siRNAs, RNAi responses to multiple cellular targets were observed in all cell-types tested in a non-cytotoxic fashion, including primary fibroblasts, keratinocytes, T and B cells, macrophage, neuronal cells and human embryonic stem cells (hESCs).

For example, the disclosure demonstrates that a fusion protein of a PTD (e.g., TAT delivery peptide) and one or more modified dsRNA binding domain (mDRBDs) derived from PKR (see, e.g., SEQ ID NO:7 below can effectively transduce cells. The mDRBDs bind to dsRNA and cover or mask dsRNA. In one embodiment, one or more mDBRDs can be used to cover the anionic surface of a dsRNA. For example, in one embodiment, two to four DBRDs cover the surface of the dsRNA cylinder. mDRBDs bind to dsRNA in a sequence independent fashion, which means that any nucleic acid can be delivered by this approach, regardless of sequence composition.

```
                                                            (SEQ ID NO: 7)
  1 magdlsagff meelntyrqk qgvvlkyqel pnsgpphdrr ftfqviidgr efpegegrsk 61 keaknaaakl aveilnkekk avsplllttt nsseglsmgn yiglinriaq kkrltvnyeq 121 casgvhgpeg fhykckmgqk eysigtgstk qeakqlaakl aylqilseet svksdylssg 181 sfattcesqs nslvtstlas esssegdfsa dtseinsnsd slnssslimn glrnnqrkak 241 rslaprfdlp dmketkytvd krfgmdfkei eligsggfgq vfkakhridg ktyvikrvky 301 nnekaerevk alakldhvni vhyngcwdgf dydpetsdds lessdydpen sknssrsktk 361 clfiqmefcd kgtleqwiek rrgekldkvl alelfeqitk gvdyihskkl ihrdlkpsni 421 flvdtkqvki gdfglvtslk ndgkrtrskg tlrymspeqi ssqdygkevd lyalglilae 481 llhvcdtafe tskfftdlrd giisdifdkk ektllqklls kkpedrpnts eilrtltvwk 541 kspeknerht c
```

Alternative approaches could include engineering a disulfide bond or ester linkage between a nucleic acid (e.g., an siRNA) and a PTD-mDRBD (e.g., TAT-mDRBD) fusion protein to further increase the binding avidity. In this embodiment, the complex is subsequently reduced and released inside the cell. Similarly an siRNA can be coated with mDRBDs and a TAT conjugated directly to an siRNA in a biologically sensitive reversible manner.

Once the PTD-mDRBD-nucleic acid complex traverses a cell's membrane, the PTD-mDRBD-nucleic acid complex is subsequently reduced and released inside the cell. The dsRNA is then hydrolyzed by Dicer, an RNAse III-like ribonuclease, thereby releasing siRNA that silences a target gene.

Thus, the potential of RNAi to selectively treat human disease can more effectively be delivered to subjects and cells. By reversibly neutralizing the anionic charge on a nucleic acid, the PTD can deliver anionically charged nucleic acids into the cell in vitro and in vivo.

A number of protein transduction domains/peptides are known in the art and have been demonstrated to facilitate uptake of heterologous molecules linked to the domain (e.g., cargo molecules). Such transduction domains facilitate uptake through a process referred to a macropinocytosis. However, macropinocytosis is a nonselective form of endocytosis that all cells perform. Consequently, this non-selective aspect of protein transduction also results in the majority of the PTD-cargo being transduced into non-target cells in vivo and thereby requires vastly more material. PTDs resemble currently used small molecule therapeutics in their lack of specific delivery to the cells and tissues for which they are intended in vivo.

The discovery of several proteins which could efficiently pass through the plasma membrane of eukaryotic cells has led to the identification of a class of proteins from which peptide transduction domains have been derived. The best characterized of these proteins are the *Drosophila* homeoprotein antennapedia transcription protein (AntHD) (Joliot et al., New Biol. 3:1121-34, 1991; Joliot et al., Proc. Natl. Acad. Sci. USA, 88:1864-8, 1991; Le Roux et al., Proc. Natl. Acad. Sci. USA, 90:9120-4, 1993), the herpes simplex virus structural protein VP22 (Elliott and O'Hare, Cell 88:223-33, 1997), the HIV-1 transcriptional activator TAT protein (Green and Loewenstein, Cell 55:1179-1188, 1988; Frankel and Pabo, Cell 55:1189-1193, 1988), and more recently the cationic N-terminal domain of prion proteins. Not only can these proteins pass through the plasma membrane but the attachment of other proteins, such as the enzyme β-galactosidase, was sufficient to stimulate the cellular uptake of these complexes. Such chimeric proteins are present in a biologically active form within the cytoplasm and nucleus. Characterization of this process has shown that the uptake of these fusion polypeptides is rapid, often occurring within minutes, in a receptor independent fashion. Moreover, the transduction of these proteins does not appear to be affected by cell type and can efficiently transduce ~100% of cells in culture with no apparent toxicity (Nagahara et al., Nat. Med. 4:1449-52, 1998). In addition to full-length proteins, protein transduction domains have also been used successfully to induce the intracellular uptake of DNA (Abu-Amer, supra), antisense oligonucleotides (Astriab-Fisher et al., Pharm. Res, 19:744-54, 2002), small molecules (Polyakov et al., Bioconjug. Chem. 11:762-71, 2000) and even inorganic 40 nanometer iron particles (Dodd et al., J. Immunol. Methods 256:89-105, 2001; Wunderbaldinger et al., Bioconjug. Chem. 13:264-8, 2002; Lewin et al., Nat. Biotechnol. 18:410-4, 2000; Josephson et al., Bioconjug., Chem. 10:186-91, 1999) suggesting that there is no apparent size restriction to this process.

The fusion of a protein transduction domain (PTD) with a heterologous molecule (e.g., a polynucleotide, small molecule, or protein) is sufficient to cause their transduction into a variety of different cells in a concentration-dependent manner. Moreover, this technique for protein delivery appears to circumvent many problems associated with DNA and drug based techniques. However, it is important to note that RNAi molecules are highly anionic and that such nucleic acid molecules have not been effectively transduced using PTDs prior to this invention.

PTDs are typically cationic in nature. These cationic protein transduction domains track into lipid raft endosomes carrying with them their linked cargo and release their cargo into the cytoplasm by disruption of the endosomal vesicle. Examples of PTDs include AntHD, TAT, VP22, cationic prion protein domains and functional fragments thereof. The disclosure provides methods and compositions that combine the use of PTDs such as TAT and poly-Arg, with a nucleic acid binding domain capable of neutralizing the anionic charge on a nucleic acid (i.e., the "cargo") domain. These compositions provide methods whereby a therapeutic or diagnostic agent can be targeted to cells whereby the PTD causes uptake of the composition into the targeted cells.

In general, the transduction domain of the fusion molecule can be nearly any synthetic or naturally-occurring amino acid sequence that can transduce or assist in the transduction of the fusion molecule. For example, transduction can be achieved in accordance with the invention by use of a protein transduction domain, such as an HIV TAT protein or fragment thereof, that is covalently linked at the N-terminal or C-terminal end to either a nucleic acid binding domain (e.g., a DRBD), a nucleic acid coated with a nucleic acid binding domain (e.g., a DRBD) or both. Alternatively, the protein transduction domain can comprise the Antennapedia homeodomain or the HSV VP22 sequence, the N-terminal fragment of a prion protein or suitable transducing fragments thereof such as those known in the art.

The type and size of the PTD will be guided by several parameters including the extent of transduction desired. Typically the PTD will be capable of transducing at least about 20%, 25%, 50%, 75%, 80% or 90%, 95%, 98% and up to, and including, about 100% of the cells. Transduction efficiency, typically expressed as the percentage of transduced cells, can be determined by several conventional methods.

PTDs will manifest cell entry and exit rates (sometimes referred to as $k_1$ and $k_2$, respectively) that favor at least picomolar amounts of the fusion molecule in the cell. The entry and exit rates of the PTD and any cargo can be readily determined or at least approximated by standard kinetic analysis using detectably-labeled fusion molecules. Typically, the ratio of the entry rate to the exit rate will be in the range of between about 5 to about 100 up to about 1000.

In one embodiment, a PTD useful in the methods and compositions of the disclosure comprise a peptide featuring substantial alpha-helicity. It has been discovered that transduction is optimized when the PTD exhibits significant alpha-helicity. In another embodiment, the PTD comprises a sequence containing basic amino acid residues that are substantially aligned along at least one face of the peptide. A PTD domain of the useful in the invention may be a naturally occurring peptide or a synthetic peptide.

In another embodiment of the disclosure, the PTD comprises an amino acid sequences comprising a strong alpha helical structure with arginine (Arg) residues down the helical cylinder.

In yet another embodiment, the PTD domain comprises a peptide represented by the following general formula: $B_1$-$X_1$-

$X_2$-$X_3$-$B_2$-$X_4$-$X_5$-$B_3$ (SEQ ID NO:8) wherein $B_1$, $B_2$, and $B_3$ are each independently a basic amino acid, the same or different; and $X_1$, $X_2$, $X_3$, $X_4$ and $X_5$ are each independently an alpha-helix enhancing amino acid, the same or different.

In another embodiment, the PTD domain is represented by the following general formula: $B_1$-$X_1$-$X_2$-$B_2$-$B_3$-$X_3$-$X_4$-$B_4$ (SEQ ID NO:9) wherein $B_1$, $B_2$, $B_3$, and $B_4$ are each independently a basic amino acid, the same or different; and $X_1$, $X_2$, $X_3$, and $X_4$ are each independently an alpha-helix enhancing amino acid the same or different.

Additionally, PTD domains comprise basic residues, e.g., lysine (Lys) or arginine (Arg), and further can include at least one proline (Pro) residue sufficient to introduce "kinks" into the domain. Examples of such domains include the transduction domains of prions. For example, such a peptide comprises KKRPKPG (SEQ ID NO:10).

In one embodiment, the domain is a peptide represented by the following sequence: X-X-R-X-(P/X)-(B/X)-B-(P/X)-X-B-(B/X) (SEQ ID NO:11), wherein X is any alpha helical promoting residue such as alanine; P/X is either proline or X as previously defined; B is a basic amino acid residue, e.g., arginine (Arg) or lysine (Lys); R is arginine (Arg) and B/X is either B or X as defined above.

In another embodiment the PTD is cationic and consists of between 7 and 10 amino acids and has the formula $KX_1RX_2X_1$ (SEQ ID NO:12) wherein $X_1$ is R or K and $X_2$ is any amino acid. An example of such a peptide comprises RKKRRQRRR (SEQ ID NO:13).

Additional transducing domains in accord with this invention include a TAT fragment that comprises at least amino acids 49 to 56 of TAT up to about the full-length TAT sequence (see, e.g., SEQ ID NO:14). A TAT fragment may include one or more amino acid changes sufficient to increase the alpha-helicity of the fragment. In some instances, the amino acid changes introduced will involve adding a recognized alpha-helix enhancing amino acid. Alternatively, the amino acid changes will involve removing one or more amino acids from the TAT fragment the impede alpha helix formation or stability. In a more specific embodiment, the TAT fragment will include at least one amino acid substitution with an alpha-helix enhancing amino acid. Typically the TAT fragment will be made by standard peptide synthesis techniques although recombinant DNA approaches may be used in some cases. In one embodiment, the substitution is selected so that at least two basic amino acid residues in the TAT fragment are substantially aligned along at least one face of that TAT fragment. In a more specific embodiment, the substitution is chosen so that at least two basic amino acid residues in the TAT 49-56 sequence are substantially aligned along at least one face of that sequence.

Additional transduction proteins (PTDs) that can be used in the compositions and methods of the invention include the TAT fragment in which the TAT 49-56 sequence has been modified so that at least two basic amino acids in the sequence are substantially aligned along at least one face of the TAT fragment. Illustrative TAT fragments include at least one specified amino acid substitution in at least amino acids 49-56 of TAT which substitution aligns the basic amino acid residues of the 49-56 sequence along at least one face of the segment and typically the TAT 49-56 sequence.

Also included are chimeric PTD domains. Such chimeric transducing proteins include parts of at least two different transducing proteins. For example, chimeric transducing proteins can be formed by fusing two different TAT fragments, e.g., one from HIV-1 and the other from HIV-2 or one from a prion protein and one from HIV.

PTDs can be linked or fused with any number of nucleic acid binding domains (e.g., DRBDs). The nucleic acid binding domain serves to neutralize or reduce the anionic charge of a nucleic acid molecule to be delivered using PTDs. The nucleic acid binding domain promotes uptake of a fusion construct comprising a nucleic acid by sufficiently reducing the anionic charge such that the cationic charge of the PTD domain is sufficient to transduce a cell by traversing a cell's membrane.

Exemplary RNA binding proteins with respective DRBDs that can be modified to include histidines linked to a PTD include histone, RDE-4 protein, or protamine. Protamines are arginine-rich proteins and include, for example, a sequence RSRRRRRRSCQTRRR (SEQ ID NO:15). Additional dsRNA binding proteins and their Accession numbers in parenthesis include: PKR (AAA36409, AAA61926, Q03963), TRBP (P97473, AAA36765), PACT (AAC25672, AAA49947, NP609646), Staufen (AAD17531, AAF98119, AAD17529, P25159), NFAR1 (AF167569), NFAR2 (AF167570, AAF31446, AAC71052, AAA19960, AAA19961, AAG22859), SPNR (AAK20832, AAF59924, A57284), RHA (CAA71668, AAC05725, AAF57297), NREBP (AAK07692, AAF23120, AAF54409, T33856), kanadaptin (AAK29177, AAB88191, AAF55582, NP499172, NP198700, BAB19354), HYL1 (NP563850), hyponastic leaves (CAC05659, BAB00641), ADAR1 (AAB97118, P55266, AAK16102, AAB51687, AF051275), ADAR2P78563, P51400, AAK17102, AAF63702), ADAR3 (AAF78094, AAB41862, AAF76894), TENR (XP059592, CAA59168), RNaseIII (AAF80558, AAF59169, Z81070Q02555/555784, PO5797), and Dicer (BAA78691, AF408401, AAF56056, S44849, AAF03534, Q9884), RDE-4 (AY071926), FLJ20399 (NP060273, BAB26260), CG1434 (AAF48360, EAA12065, CAA21662), CG13139 (XP059208, XP143416, XP110450, AAF52926, EEA14824), DGCRK6 (BAB83032, XP110167) CG1800 (AAF57175, EAA08039), FLJ20036 (AAH22270, XP134159), MRP-L45 (BAB14234, XP129893), CG2109 (AAF52025), CG12493 (NP647927), CG10630 (AAF50777), CG17686 (AAD50502), T22A3.5 (CAB03384) and accession number EAA14308. The sequences of such nucleic acid binding proteins are known in the art based upon the accession numbers. The sequences associated with said accession numbers are specifically incorporated herein by reference in their entireties.

Nucleic acid binding polypeptides can comprise any of the full length polypeptides of the foregoing accession numbers, fragments of any of the foregoing as well as modified polypeptides comprising from 1-10 amino acid substitution comprising a sequence as set forth in the above-identified accession numbers.

It will be understood that the PTD may be fused to a nucleic acid wherein the nucleic acid is coated with one or more nucleic acid binding domains sufficient to reduce any anionic charge. Alternatively, the PTD may be operably linked to a nucleic acid binding domain (e.g., a DRBD) which in-turn coats an anionically charged nucleic acid.

A PTD and an anionic nucleic acid molecule (e.g., a dsRNA) can be linked using phosphoramidate, phosphorothioate, or phosphodiester linkers. For example, an siRNA comprising a 3'-amino group with a 3-carbon linker may be utilized for linking the siRNA to a PTD. The siRNA is conjugated to the PTD via a heterobifunctional cross linker.

A disulfide bond between the PTD and an siRNA or between the DRBD and the siRNA can be formed to facilitated targeted/time release. A disulfide bond between a PTD and nucleic acid or DRBD and a nucleic acid can be cleaved to release the nucleic acid.

Where the PTD is operably linked to a nucleic acid binding domain (e.g., a DRBD), the two domains can be linked by peptide linkers, chemical synthesized or expressed by a polynucleotide construct where the domains are operably linked such that their coding frames generate a single functional polypeptide comprising a PTD domain and a DRBD domain.

As noted, components of the fusion polypeptides disclosed herein, e.g., a PTD-nucleic acid binding domain (e.g., a mDRBD), and a nucleic acid domain, and optionally peptide linkers, can be organized in nearly any fashion provided that the fusion polypeptide has the function for which it was intended (e.g., sufficiently cationically charged). The invention provides fusion polypeptides or chimeric proteins comprising one or more PTDs linked to one or more nucleic acid binding domain which is either directly or indirectly linked to a nucleic acid domain (e.g., a therapeutic or diagnostic DNA, RNA, siRNA and the like). Each of the several domains may be directly linked or may be separated by a linker peptide. The domains may be presented in any order. Additionally, the fusion polypeptides may include tags, e.g., to facilitate identification and/or purification of the fusion polypeptide, such as a 6×HIS tag.

Peptide linkers that can be used in the fusion polypeptides and methods of the invention will typically comprise up to about 20 or 30 amino acids, commonly up to about 10 or 15 amino acids, and still more often from about 1 to 5 amino acids. The linker sequence is generally flexible so as not to hold the fusion molecule in a single rigid conformation. The linker sequence can be used, e.g., to space the PTD domain from the nucleic acid binding domain and/or nucleic acid domain. For example, the peptide linker sequence can be positioned between the protein transduction domain and the nucleic acid domain, e.g., to provide molecular flexibility. The length of the linker moiety is chosen to optimize the biological activity of the polypeptide comprising a PTD domain fusion construct and can be determined empirically without undue experimentation. The linker moiety should be long enough and flexible enough to allow a nucleic acid binding domain to freely interact with a nucleic acid or vice versa. Examples of linker moieties are -Gly-Gly-, GGGGS (SEQ ID NO:16), (GGGGS)$_N$ (SEQ ID NO:16), GKSSGSG-SESKS (SEQ ID NO:17), GSTSGSGKSSEGKG (SEQ ID NO:18), GSTSGSGKSSEGSGSTKG (SEQ ID NO:19), GSTSGSGKPGSGEGSTKG (SEQ ID NO:20), or EGKSSGSGSESKEF (SEQ ID NO:21). Linking moieties are described, for example, in Huston et al., Proc. Nat'l Acad. Sci. 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are hereby incorporated by reference.

The disclosure provides chimeric/fusion polypeptides comprising a PTD and a nucleic acid binding protein. In one aspect, the chimeric/fusion polypeptide comprises a PTD linked to a double stranded RNA binding protein that shields the anionic dsRNA charge.

In one embodiment, the fusion construct of the disclosure may comprise, in addition to the PTD and nucleic acid binding domain, a targeting domain. The targeting domain can be a receptor or receptor ligand useful for directing the fusion construct to a particular cell type that expresses the cognate binding domain.

A polypeptide (including a fusion polypeptide) refers to a polymer in which the monomers are amino acid residues which are joined together through amide bonds. When the amino acids are alpha-amino acids, either the L-optical isomer or the D-optical isomer can be used. A polypeptide encompasses an amino acid sequence and includes modified sequences such as glycoproteins, retro-inverso polypeptides, D-amino acid modified polypeptides, and the like. A polypeptide includes naturally occurring proteins, as well as those which are recombinantly or synthetically synthesized. A polypeptide may comprise more than one domain have a function that can be attributed to the particular fragment or portion of a polypeptide. A domain, for example, includes a portion of a polypeptide which exhibits at least one useful epitope or functional domain. Two or more domains may be functionally linked such that each domain retains its function yet comprises a single polypeptide (e.g., a fusion polypeptide). For example, a functional fragment of a PTD includes a fragment which retains transduction activity. Biologically functional fragments, for example, can vary in size from a polypeptide fragment as small as an epitope capable of binding an antibody molecule, to a large polypeptide capable of participating in the characteristic induction or programming of phenotypic changes within a cell.

In some embodiments, retro-inverso peptides are used. "Retro-inverso" means an amino-carboxy inversion as well as enantiomeric change in one or more amino acids (i.e., levantory (L) to dextrorotary (D)). A polypeptide of the disclosure encompasses, for example, amino-carboxy inversions of the amino acid sequence, amino-carboxy inversions containing one or more D-amino acids, and non-inverted sequence containing one or more D-amino acids. Retro-inverso peptidomimetics that are stable and retain bioactivity can be devised as described by Brugidou et al. (Biochem. Biophys. Res. Comm. 214(2): 685-693, 1995) and Chorev et al. (Trends Biotechnol. 13(10): 438-445, 1995). The overall structural features of a retro-inverso polypeptide are similar to those of the parent L-polypeptide. The two molecules, however, are roughly mirror images because they share inherently chiral secondary structure elements. Main-chain peptidomimetics based on peptide-bond reversal and inversion of chirality represent important structural alterations for peptides and proteins, and are highly significant for biotechnology. Antigenicity and immunogenicity can be achieved by metabolically stable antigens such as all-D- and retro-inverso-isomers of natural antigenic peptides. Several PTD-derived peptidomimetics are provided herein.

Polypeptides and fragments can have the same or substantially the same amino acid sequence as the naturally derived polypeptide or domain. "Substantially identical" means that an amino acid sequence is largely, but not entirely, the same, but retains a functional activity of the sequence to which it is related. An example of a functional activity is that the fragment is capable of transduction, or capable of binding to an RNA. For example, fragments of full length TAT are described herein that have transduction activity. In general two polypeptides or domains are "substantially identical" if their sequences are at least 85%, 90%, 95%, 98% or 99% identical, or if there are conservative variations in the sequence. A computer program, such as the BLAST program (Altschul et al., 1990) can be used to compare sequence identity.

A polypeptide of the disclosure can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a peptide or polypeptide, including the peptide backbone, the amino acid side-chains and the amino or carboxyl termini. It will be appreciated that the same type of modification may be present in the same or varying degrees at several sites in a given peptide or polypeptide. Also, a given peptide or polypeptide may contain many types of modifications. A peptide or polypeptide may be branched, for example, as a result of ubiquitination, and they may be cyclic, with or without branching. Cyclic, branched, and branched cyclic peptides and polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann N.Y. Acad Sci 663:48-62 (1992).)

A polypeptide domain or a fusion polypeptide of the disclosure can be synthesized by commonly used methods such as those that include t-BOC or FMOC protection of alpha-amino groups. Both methods involve stepwise synthesis in which a single amino acid is added at each step starting from the C terminus of the peptide (See, Coligan, et al., Current Protocols in Immunology, Wiley Interscience, 1991, Unit 9). Polypeptides of the disclosure can also be synthesized by the well known solid phase peptide synthesis methods such as those described by Merrifield, J. Am. Chem. Soc., 85:2149, 1962; and Stewart and Young, Solid Phase Peptides Synthesis, Freeman, San Francisco, 1969, pp. 27-62, using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with a 1% acetic acid solution, which is then lyophilized to yield the crude material. The peptides can be purified by such techniques as gel filtration on Sephadex G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

In another embodiment, the disclosure provides a method of producing a fusion polypeptide comprising a PTD domain and a nucleic acid binding domain or RNA by growing a host cell comprising a polynucleotide encoding the fusion polypeptide under conditions that allow expression of the polynucleotide, and recovering the fusion polypeptide. A polynucleotide encoding a fusion polypeptide of the disclosure can be operably linked to a promoter for expression in a prokaryotic or eukaryotic expression system. For example, such a polynucleotide can be incorporated in an expression vector. Recombinant molecular biology techniques can be used to link, for example, a PTD domain and a mDRBD domain to generate a polynucleotide of the disclosure such that upon expression the polypeptide comprising the domains are functionally operative.

The term "operably linked" or "operably associated" refers to functional linkage between regulatory and/or coding domains of a polynucleotide regulated by the regulatory sequence as well as the link between encoded domains of the fusion polypeptides such that each domain is linked in-frame to give rise to the desired polypeptide sequence.

Accordingly, the disclosure also includes isolated polynucleotides (e.g., DNA, cDNA, or RNA) encoding the polypeptides, including fusion polypeptides, of the disclosure. Included are polynucleotides that encode analogs, mutants, conservative variations, and variants of the polypeptides described herein. The term "isolated" as used herein refers to a polynucleotide that is substantially free of proteins, lipids, and other polynucleotides with which an in vivo-produced polynucleotide naturally associates. Typically, the polynucleotide is at least 70%, 80%, or 90% isolated from other matter, and conventional methods for synthesizing polynucleotides in vitro can be used in lieu of in vivo methods. As used herein, "polynucleotide" refers to a polymer of deoxyribonucleotides or ribonucleotides, in the form of a separate fragment or as a component of a larger genetic construct (e.g., by operably linking a promoter to a polynucleotide encoding a peptide of the disclosure or operably linking heterologous coding domains). Numerous genetic constructs (e.g., plasmids and other expression vectors) are known in the art and can be used to produce the polypeptides of the disclosure in cell-free systems or prokaryotic or eukaryotic (e.g., yeast, insect, or mammalian) cells. By taking into account the degeneracy of the genetic code, one of ordinary skill in the art can readily synthesize polynucleotides encoding the polypeptides of the disclosure. The polynucleotides of the disclosure can readily be used in conventional molecular biology methods to produce the peptides of the disclosure.

Such polynucleotides include naturally occurring, synthetic, and intentionally manipulated polynucleotides. A polynucleotide encoding a PTD domain or a DRBD domain or functional fragments thereof includes sequences that are degenerate as a result of the genetic code. Polynucleotide sequences that encode a PTD or DRBD or functional fragment thereof can be readily ascertained based upon the polypeptide sequences provided herein and with reference to the accession numbers provided herein. There are 20 natural amino acids, most of which are specified by more than one codon. Therefore, polynucleotides comprising all degenerate nucleotide sequences are included so long as the resulting polypeptide comprises an amino acid resulting in a functional PTD or mDRBD polypeptide domain.

Polynucleotides encoding a fusion polypeptide or domains thereof can be inserted into an "expression vector." The term "expression vector" refers to a genetic construct such as a plasmid, virus or other vehicle known in the art that can be engineered to contain a polynucleotide encoding a polypeptide of the disclosure. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a polynucleotide can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

"Host cells" encompassed by of the disclosure are any cells in which the polynucleotides of the disclosure can be used to express the fusion polypeptide or functional domains thereof. The term also includes any progeny of a host cell. Host cells, which are useful, include bacterial cells, fungal cells (e.g., yeast cells), plant cells and animal cells. A fusion polypeptide of the disclosure can be produced by expression of polynucleotide encoding a fusion polypeptide in prokaryotes. These include, but are not limited to, microorganisms, such as bacteria transformed with recombinant bacteriophage DNA, plasmid DNA, or cosmid DNA expression vectors encoding a fusion polypeptide of the disclosure. The constructs can be expressed in *E. coli* in large scale for in vitro assays. Host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology (1986)). As representative examples of appropriate hosts, there may be mentioned: fungal cells, such as yeast; insect cells such as *Drosophila* S2 and *Spodoptera* Sf9; animal cells such as CHO, COS or Bowes melanoma; plant cells, and the like. The selection of an appropriate host is deemed to be within the scope of those skilled in the art from the teachings herein.

Host cells can be eukaryotic host cells (e.g., mammalian cells). In one aspect, the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells. Chinese hamster ovary (CHO) cells are widely used for the production of several complex recombinant proteins, e.g. cytokines, clotting factors, and antibodies (Brasel et al., Blood 88:2004-2012, 1996; Kaufman et al., J. Biol Chem 263: 6352-6362, 1988; McKinnon et al., J Mol Endocrinol 6:231-239, 1991; Wood et al., J. Immunol. 145:3011-3016, 1990). The dihydrofolate reductase (DHFR)-deficient mutant cell lines (Urlaub et al., Proc Natl Acad Sci USA 77:4216-4220, 1980) are the CHO host cell lines commonly used because the efficient DHFR selectable and amplifiable gene expression system allows high level recombinant protein expression in these cells (Kaufman, Meth Enzymol 185:527-566, 1990). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

Eukaryotic systems, and typically mammalian expression systems, allow for proper post-translational modifications of expressed mammalian proteins to occur. Eukaryotic cells that possess the cellular machinery for proper processing of the primary transcript, glycosylation, phosphorylation, and advantageously secretion of the gene product can be used as host cells for the expression of the PTD-fusion polypeptide of the disclosure. Such host cell lines may include, but are not limited to, CHO, VERO, BHK, HeLa, COS, MDCK, Jurkat, HEK-293, and WI38.

For long-term, high-yield production of recombinant proteins, stable expression is typically used. Rather than using expression vectors that contain viral origins of replication, host cells can be transformed with the cDNA encoding a fusion polypeptide of the disclosure controlled by appropriate expression control elements (e.g., promoter, enhancer, sequences, transcription terminators, polyadenylation sites, and the like), and a selectable marker. The selectable marker confers resistance to a selective killing agent and upon stable integration of the heterologous polynucleotide, allows growth of resistant cells. Such resistant cells grow to form foci that, in turn, can be cloned and expanded into cell lines. For example, following the introduction of foreign DNA, engineered cells may be allowed to grow for 1-2 days in an enriched media, and then are switched to a selective media. A number of selection systems may be used, including, but not limited to, the herpes simplex virus thymidine kinase (Wigler et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy et al., Cell, 22:817, 1980) genes can be employed in tk-, hgprt- or aprt-cells, respectively. Also, antimetabolite resistance can be used as the basis of selection for dhfr, which confers resistance to methotrexate (Wigler et al., Proc. Natl. Acad. Sci. USA, 77:3567, 1980; O'Hare et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin et al., J. Mol. Biol., 150:1, 1981); and hygro, which confers resistance to hygromycin genes (Santerre et al., Gene, 30:147, 1984). Additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase), which confers resistance to the ornithine decarboxylase inhibitor, 2-(difluoromethyl)-DL-ornithine, DEMO (McConlogue L., In: Current Communications in Molecular Biology, Cold Spring Harbor Laboratory, ed., 1987).

In yeast, a number of vectors containing constitutive or inducible promoters may be used (see, e.g., Current Protocols in Molecular Biology, Vol. 2, Ed. Ausubel et al., Greene Publish. Assoc. & Wiley Interscience, Ch. 13, 1988; Grant et al., "Expression and Secretion Vectors for Yeast," in Methods in Enzymology, Eds. Wu & Grossman, Acad. Press, N.Y., Vol. 153, pp. 516-544, 1987; Glover, DNA Cloning, Vol. II, IRL Press, Wash., D.C., Ch. 3, 1986; "Bitter, Heterologous Gene Expression in Yeast," Methods in Enzymology, Eds. Berger & Kimmel, Acad. Press, N.Y., Vol. 152, pp. 673-684, 1987; and The Molecular Biology of the Yeast Saccharomyces, Eds. Strathern et al., Cold Spring Harbor Press, Vols. I and II, 1982). A constitutive yeast promoter, such as ADH or LEU2, or an inducible promoter, such as GAL, may be used ("Cloning in Yeast," Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

In one embodiment of the disclosure, distinct domains (e.g., a PTD or mDRBD) are expressed from a host cell comprising a polynucleotide encoding the domain. The domain is then purified using art-known methods (as described further herein). The domains are then chemically linked directly or indirectly (e.g., with a peptide linker) to form a fusion polypeptide. Alternatively, a polynucleotide encoding a fusion polypeptide is expressed in a host cell and the fusion polypeptide is purified using art known methods. Regardless of the method by which the fusion polypeptide is formed; the fusion polypeptide is then contacted with a nucleic acid (e.g., an anionically charged dsRNA) under conditions whereby the nucleic acid binding protein (e.g., mDRBD) interacts with the nucleic acid in a sequence independent manner. The fusion construct may comprise one or more nucleic acid binding proteins (e.g., mDRBD). In one embodiment, the nucleic acid molecules (e.g., the dsRNA) interacts with at least two nucleic acid binding proteins.

Any of various art-known methods for protein purification can be used to isolate a polypeptide domain or fusion polypeptide of the disclosure. For example, preparative chromatographic separations and immunological separations (such as those employing monoclonal or polyclonal antibodies) can be used. Carrier peptides can facilitate isolation of fusion polypeptides. Such carrier peptides or purification tags can be operably linked to a PTD, mDRBD or PTD-mDRBD fusion polypeptide of the disclosure. For example, glutathione-S-transferase (GST) allows purification with a glutathione agarose affinity column. When either Protein A or the ZZ domain from *Staphylococcus aureus* is used as the tag, purification can be accomplished in a single step using an IgG-sepharose affinity column. The pOprF-peptide, which is the N-terminal half of the *P. aeruginosa* outer membrane protein F, can readily be purified because it is the prominent protein species in outer membrane preparations. If desired, the fusion peptides can be purified using reagents that are specifically reactive with (e.g., specifically bind) the a functional fragment of the fusion peptide. For example, monoclonal or polyclonal antibodies that specifically bind the mDRBD or PTD domain can be used in conventional purification methods. Techniques for producing such antibodies are well known in the art. A fusion polypeptide of the disclosure can also be engineered to contain a cleavage site to aid in protein recovery or other linker moiety separating a PTD from a nucleic acid binding protein or dsRNA molecule.

As used herein, a nucleic acid domain can be any polynucleotide (e.g., a ribozyme, antisense molecule, polynucleotide, oligonucleotide and the like). In the specific examples provided herein, the nucleic acid domain comprises a dsRNA.

dsRNA comprising siRNA sequences that are complementary to a nucleotide sequence of the target gene can be prepared in any number of methods. Methods and techniques for identifying siRNA sequences are known in the art. The siRNA nucleotide sequence can be obtained from the siRNA Selection Program, Whitehead Institute for Biomedical Research, Massachusetts Institute of Technology, Cambridge, Mass. (currently available at [http://jura.wi.mit.edu/bioc/siRNAext/) after supplying the Accession Number or GI number from the National Center for Biotechnology Information website (available on the World Wide Web at ncbi.nlm.nih.gov). Alternatively, dsRNA containing appropriate siRNA sequences can be ascertained using the strategy of Miyagishi and Taira (2003). Typically, the longer the dsRNA sequence the increase in anionic charge requiring additional DRBDs or other nucleic acid binding proteins. Commercially available RNAi designer algorithms also exist ([http://rnaidesigner.invitrogen.com/rnaiexpress/). Preparation of RNA to order is commercially available. Once obtained the RNA molecule comprising the siRNA sequence can be bound by a nucleic acid binding protein or directly linked or indirectly linked to a PTD domain of the disclosure.

The dsRNA is operably linked to a PTD or is incubated under conditions such that a PTD comprising a nucleic acid binding protein (e.g., a mDRBD) or a nucleic acid binding protein interacts with the dsRNA. Typically the interaction of the dsRNA with the nucleic acid binding protein results in a reduction of the overall anionic charge of the complex (e.g., the mDRBD and dsRNA).

The methods, compositions, and fusion polypeptides of the disclosure provide enhanced uptake and release of nucleic acid molecules.

The term "therapeutic" is used in a generic sense and includes treating agents, prophylactic agents, and replacement agents. Examples of therapeutic molecules include, but are not limited to, cell cycle control agents; agents which inhibit cyclin protein production, such as siRNA polynucleotides to the cyclin G1 and cyclin D1 genes; dsRNA that can be cleaved to provide siRNA molecules directed to specific growth factors such as, for example, epidermal growth factor (EGF), vascular endothelial growth factor (VEGF), erythropoietin, G-CSF, GM-CSF, TGF-α, TGF-β, and fibroblast growth factor; cytokines, including, but not limited to, Interleukins 1 through 13 and tumor necrosis factors; anticoagulants, anti-platelet agents; TNF receptor domains and the like.

Using such methods and compositions, various diseases and disorders can be treated. For example, growth of tumor cells can be inhibited, suppressed, or destroyed upon delivery of an anti-tumor siRNA. For example, an anti-tumor siRNA can be an siRNA targeted to a gene encoding a polypeptide that promotes angiogenesis. Various angiogenic proteins associated with tumor growth are known in the art.

The fusion polypeptides of the disclosure are useful for the delivery of anionically charged nucleic acid molecules (e.g., dsRNA, siRNA, DNA, antisense, ribozymes and the like) for the treatment and/or diagnosis of a number of diseases and disorders. For example, the fusion polypeptides can be used in the treatment of cell proliferative disorders, wherein the nucleic acid binding domain (e.g., DRBD) neutralizes that charge on nucleic acids used to target genes that induce cell proliferation. The PTD domain facilitates uptake of the fusion polypeptide and the nucleic acid binding domain (e.g., DRBD). Thus, the fusion polypeptide is useful for treatment of cells having cell proliferative disorders. Similarly, the fusion polypeptides of the invention can be used to treatment inflammatory diseases and disorders, infections, vascular disease and disorders and the like.

Thus, it is to be understood that the disclosure is not to be limited to any particular nucleic acid binding domain or nucleic acid domain. Rather, the nucleic acid domain can be any nucleic acid binding domain capable of neutralizing or reducing the anionic charge of a nucleic acid to be delivered. Furthermore, any anionically charged nucleic acid (e.g., dsRNA, siRNA and the like) can be delivered using the methods of the invention.

Typically a fusion polypeptide of the disclosure will be formulated with a pharmaceutically acceptable carrier, although the fusion polypeptide may be administered alone, as a pharmaceutical composition.

A pharmaceutical composition according to the disclosure can be prepared to include a fusion polypeptide of the disclosure, into a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. By "therapeutically effective dose" is meant the quantity of a fusion polypeptide according to the disclosure necessary to prevent, to cure, or at least partially arrest the symptoms of a disease or disorder (e.g., to inhibit cellular proliferation). Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference.

As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (e.g., subcutaneous, intravenous, and the like), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition (e.g., enteric coatings are known in the art). The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the subject to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The following examples are meant to illustrate, not limit, the disclosed invention.

EXAMPLES

In developing a siRNA delivery strategy, the proven macromolecular delivery properties of cationic Peptide Transduction Domain (PTD) delivery vehicle (also termed Cell Penetrating Peptide [CPP]) were used. Such PTD include, for example, TAT, 8×Arg, and Antp that have been shown to deliver a wide variety of cargo into primary cells, into most, if not all, tissues in pre-clinical models and are currently being tested in multiple clinical trials. Cationic PTDs are rapidly taken up into cells by macropinocytosis, a specialized form of fluid phase uptake that all cells perform. However, conjugation of cationic PTDs (6-8 positive charges) to anionic siRNAs (~40 negative charges) results in charge neutralization, inactivation of the PTD, aggregation/precipitation, and cytotoxicity with limited siRNA entry into the cells. To circumvent PTD charge neutralization (inactivation), a TAT PTD fusion protein with a single dsRNA Binding Domain (PTD-DRBD) that binds the siRNA with high avidity (KD ~10-9) and thereby masks its negative charge was developed. DRBDs are small, ~65 residue domains that specifically binds ~12-16 bp of the dsRNA backbone on 90° surface quadrants of the dsRNA helix, resulting in four DBRDs encompassing a single siRNA (4:1 ratio) (FIG. 1a and FIG. 4).

Figure 4:
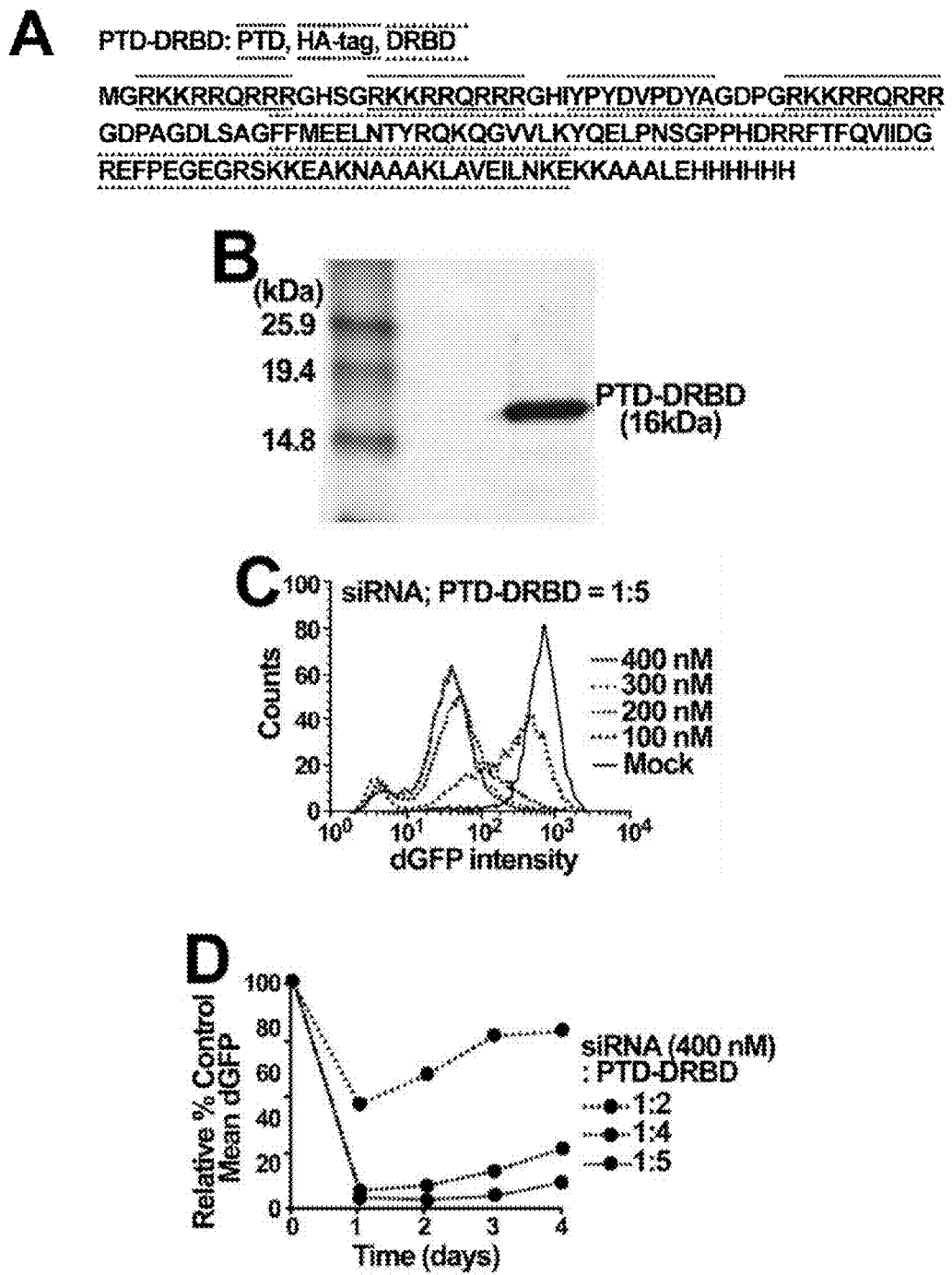
FIG. 4A-D shows PTD-DRBD characterization. (a) Single letter amino acid sequence and domain demarcation of PTD-DRBD (SEQ ID NO:22). (b) Coomassie Blue staining of purified PTD-DRBD protein (16.7 kDa). (c) Dose response curve of PTD-DRBD: GFP RNAi response in H1299 dGFP expressing cells at 24 h post-addition, as indicated. (d) Molar ratio analysis of siRNA:PTD-DRBD at 24 h post-addition to H1299 dGFP expressing cells, as indicated.

PTD-DRBD Fusion Protein Construction, Design and Purification.

pPTD-DRBD was constructed by PCR cloning of PKR DRBD-1 into a modified pTAT vector8 resulting in TAT-TATHA-TAT-DRBD-6×His (FIG. 4). The HA epitope tag was used to follow the protein by immunoblot analysis and the 6×His tag was used for purification over the first column, Ni-NTA. PTD-DRBD expression utilized BL21 codon plus (DH3) *E. coli* (Strategene) cells were transformed with pPTD-DRBD, cultured at 37° C. in LB, then at 25° C. for 12 h after induction with 400 µM IPTG. Cells were recovered by centrifugation for 5 min at 4,500 g, sonicated in Buffer A (20 mM Hepes [pH 7.5], 500 mM NaCl, 5 µg/ml Aprotinin, 1 µg/ml Leupeptin, 0.8 mM PMSF) plus 20 mM imidazole and soluble protein isolated by centrifugation for 15 min at 50,000 g.

PTD-DRBD was purified by passage over a Ni-NTA column (Qiagen), followed by loading onto a Mono-S AKAT FPLC in Buffer B (50 mM Hepes [pH 7.5], 20 mM NaCl, 5% glycerol) and eluted in Buffer C (Buffer B plus 1.5 M NaCl). Purified PTD-DRBD was desalted (PD-10) into PBS-10% glycerol, and stored at −80° C. EGFP-PEST (dGFP) or DsRed-PEST (dDsRed) lentiviruses were constructed using pCSC-SP-CW-EGFP-PEST or pCSC-SP-CW-DSRED20 and pd2EGFP-N1- (destabilized GFP; BD clontech) or pDsRed-Express-DR (destabilized DsRed; BD clontech).

Cell Culture Conditions.

H1299, HaCaT keratinocytes, HFF primary human fibroblasts, B16F0 melanoma cells were cultured in 10% FBS-DMEM, antibiotics. T98G glioblastoma cells were cultured in 5% FBS-MEM, antibiotics. HUVEC cells were cultured in EGM-2 MV BulletKit (Lonza). Jurkat T cells were cultured in 10% FBS-RPMI, antibiotics. THP-1 macrophage were grown in 10% FBS-RPMI plus 1 mM sodium pyruvate, 4.5 g/L glucose, 50 µM β-mercaptoethanol, antibiotics. Primary murine T cells were recovered from mouse spleens by MACS (Miltenyi Biotec), activated with anti-CD3ε antibody for 1 day and cultured in 10% FBS RPMI plus 2 mM L-Glutamine, 55 µM β-mercaptoethanol, 20 ng/mL IL2. The hESC line HUES9 was kindly provided by D. Melton (HHMI, Harvard University) and H9 hESCs were obtained from WiCell. H9 hESCs were grown in 20% knockout serum-DMEM-F12 plus 55 µM β-mercaptoethanol, NEAA, Gluta-Max, 4 ng/ml bFGF, antibiotics on murine fibroblast feeder layer.

HUES9 hESCs were grown in HUES media (10% knockout serum-DMEM plus 10% Plasmonate, 55 µM β-mercaptoethanol, NEAA, Gluta-Max, 4 ng/ml bFGF, antibiotics) without murine fibroblast feeder layer in media preconditioned for 24 h on murine fibroblasts.

Destabilized GFP (dGFP) and DsRed (dDsRed) proteins have ~2 h and ~12 h half-lives, respectively, significantly shorter than their wild type parental proteins (>24 h) and therefore were used as RNAi reporter targets. dGFP and dDsRed expressing cells were generated by infection with VSVG expressing dGFP and/or dDsRed (BD Clontech) lentivirus. VSVG-dGFP and/or VSVG-dDsRed infected cells were isolated by FACS.

PTD-DRBD siRNA Delivery into Cells. A typical PTD-DRBD siRNA delivery reaction mixed 10 µl of 1-5 µM siRNA in water with 10 µl of 10-50 µM PTD-DRBD in PBS-10% glycerol plus 4 µl PBS-10% glycerol on ice for 30 min, diluted 1:5 in media and added to $7.5 \times 10^4$ cells/well in 48 well plate for 1-6 h with final siRNA concentrations between 100-400 nM. Cells were then washed with trypsin or washed in 58 µg/ml heparin sulfate plus media for 10 min to remove extracellular PTD-DRBD:siRNA, followed by addition of fresh media plus FBS. For primary T cells, Jurkat, Namalwa, THP-1 suspension cells, $2 \times 10^5$ cells were treated with 100-400 nM siRNA:PTD-DRBD for 1 h in media plus 10-20% Q-serum (5 ml FBS+1 ml Source 30Q resin [Amersham Bioscience], 30 min at RT on mixing platform, followed by 0.22 µm filtration), washed 2× with media, followed by addition of fresh complete media. For H9 and HUES9 hESCs, $6.6 \times 10^5$ cells were treated with 200-400 nM siRNA-PTD-DRBD for 1 h in serum-free media with no feeder layer, followed by 5 hr in serum-free media on fibroblast feeder layer, then 24 h with full HUES media plus serum. For control siRNA lipofections, cells were treated with a dose curve that yielded the highest RNAi response with 100 nM siRNA in Lipofectamine-2000 (Lipofection) (Invitrogen) or 10-50 nM siRNA in Lipofectamine-RNAiMAX (Lipofection 2) (Invitrogen) per the manufacturer's instructions. siRNAs sequences used in this study: EGFP1 (Ambion pre-designed siRNA), EGFP2 (Ambion #4626 Silencer GFP), GAPDH1 (Ambion #4626), GAPDH2 (Ambion #4605), Oct4 (Ambion pre-designed), Nanog (Ambion pre-designed), Sox2 (Ambion pre-designed) and Silencer Negative (control 1) (Ambion #4611G); luciferase (control 2) (Dharmacon #D-001400-01-20), DsRed (Ambion pre-designed), β-gal17 (Dharmacon). Immunoblotting, RT-PCR and microarrays. $6 \times 10^4$ cells/well in 48 well were recovered with trypsin/EDTA, whole cell lysates were prepared in RIPA buffer (1% TritonX-100, 1% Sodium Deoxycholate, 40 mM Tris-HCl, 150 mM NaCl, 0.2% SDS, 5 µg/ml Aprotinin, 1 µg/ml Leupeptin, 0.8 mM PMSF) for 30 min on ice, clarified by centrifugation and proteins resolved by 10% SDS-PAGE.

Immunoblot analyses were performed on PVDF membranes blocked in 4% skim milk, PBS-T (0.05% PBS, Tween20) for 1 h at RT, reacted with anti-Oct4 (Santa Cruz), anti-GAPDH (Santa Cruz) and anti-α-tublin (Sigma) antibodies overnight at 4° C., then washed and exposed to HRP conjugated anti-IgG (Santa cruz) antibodies and detected by ECL (Pierce). For GAPDH mRNA TaqMan RT-PCR (Applied Biosystems), $6 \times 10^4$ dGFP-H1299 cells/well in 48 well plate were treated as described above with 400 nM GAPDH, control Silencer Negative or control Luciferase siRNA and total RNA isolated at 6, 12, 24, 36, 72 and 96 h post-addition. $5 \times 10^4$ HUVEC cells/well in 48 well plate were treated as described above with 400 nM GAPDH, control Silencer Negative or control GFP siRNA and total RNA isolated at 6, 12 and 24 h post-addition. cDNA was synthesized using Oligo-dT and GAPDH mRNA expression was detected using TAQ-MAN probe (Ambion) on 7300 Real time PCR system (Applied Biosystems). Mean values normalized to β2 microglobulin and reported as percent of mock GAPDH control, error bar indicates s.d., all experiments performed in triplicate. For whole genome microarrays analysis, $6 \times 10^5$ H1299 cells/well in 6 well plate were treated as described above with 400 nM GAPDH or PBS. Total RNA was isolated at 12 and 24 h post-addition, and used to probe whole genome microarrays (Illumina).

Immunohistochemistry and Flow Cytometry Analysis.

Cells were fixed with 4% paraformaldehyde for 30 min at RT, permeabilized in 0.1% TritonX100-PBS for 15 min at RT, blocked in 3% skim milk-PBS for 30 min at RT, then reacted with anti-Oct4 (Santa Cruz), anti-SSEA4 (Santa Cruz) and anti-GATA6 (Santa Cruz) antibodies in 0.1% BSA-PBS overnight at 4° C. Cells were washed and reacted with either Alexa488 or Alexa594 conjugated anti-IgG (Molecular Probes) for 30 min at RT. DNA was counter stained with Hoechst 33342 (Molecular Probes). Cells were analyzed by confocal microscopy (Olympus Flouview). For flow cytometry, $1 \times 10^4$ dGFP and/or dDsRed positive cells were analyzed on a FACScan (BD Biosciences).

IFN-α and TNF-α Analyses.

Human Peripheral blood mononuclear cells (PBMCs) were isolated from healthy donors by standard density gradient centrifugation with Ficoll-Paque PLUS™ (Amersham Biosciences) at 2000 rpm for 20 min at 20° C. To remove platelets, PBMCs were washed 4× in 50 ml PBS, centrifuged at 1500 rpm for 8 min at 4° C. $8 \times 10^5$ freshly isolated PBMCs were treated as described above with 100 nM β-gal siRNA17 plus either PTDDRBD or Lipofection and seeded into 96 well-plate ($4 \times 10^5$ cells/well). As a positive control, PBMCs were treated with 10 µg/ml Imiquimod for IFN-α induction and 10 µg/ml LPS for TNF-α induction. Culture supernatants were collected at 4 h and 24 h post-addition, and assayed for IFN-α and TNF-α by ELISA (R&D systems).

Intranasal PTD-DRBD siRNA In Vivo Delivery.

Transgenic ROSA26 loxP-Stop-loxP Luciferase mice19 (Jackson Labs) were inoculated intratracheally with 30 µl of 3 mg/ml TAT Cre21 to turn uciferase gene by removal of a loxP-STOP-loxP DNA transcriptional terminator genetic element. After 3 months, D-Luciferin (150 mg/kg) was administrated intraperitoneally and luciferase expression monitored by live animal imaging (IVIS-100 Xenogen) for 5-15 min post-luciferin injection, twice daily per mouse (Day 0). Following this baseline measurement, mice were randomized into groups (n=3) and inoculated intranasally with 60 µl (30 µl/nostril) of PTD-DRBD plus 750 pmol Luc siRNA or control GFP siRNA in PBS or PBS (mock) control. Luciferase expression was monitored by IVIS imaging, twice daily per mouse each day for 15 days.

PTD-DRBD Mediated siRNA Delivery.

PTD-DRBD was purified from *E. coli* and mixed with siRNA. siRNAs sequences used: EGFP1, EGFP2 (Silencer GFP), GAPDH, Silencer Negative control (con1), Akt1, Akt2 and Akt3 (Ambion); and EGFRvIII (Dharmacon).

Cell Lines.

Glioblastoma T98G cells (ATCC) were cultured in MEM plus 5% FBS, antibiotics. Human U87MG EGFRvIII cells were cultured in DMEM plus 10% FBS, antibiotics.

Cell Viability.

Cells were treated with WST-1 (2-[2-methoxy-4-nitrophenyl]-3-[4-nitrophenyl]-5-[2,4-disulphophenyl]-2H-tetrazolium, monosodium salt) on day 0, 1, 2, 4, 6 and 7 (Roche Applied Science, Mannheim, Germany). For TUNEL, cells were assayed 2 d after PTD-DRBD:siRNA treatment, fixed with 4% paraformaldehyde, washed, detected by in situ cell death detection kit fluorescence (Roche Diagnostic), then assayed by immunofluorescent microscopy or flow cytometry.

Immunoblotting.

Immunoblot analyses were performed on PVDF membranes (12), and reacted with anti-EGFR (Lab vision), anti-Akt1 (Cell Signaling), anti-Akt2 (Cell Signaling), Akt-3 (Cell Signaling), anti-β-tublin (Sigma) antibodies, washed, exposed to HRP conjugated anti-IgG (Santa cruz) antibodies and detected by ECL (Pierce).

Intracerebral Glioblastoma Model.

Intracerebral, right corpus striatum tumors were established in nude mice by insertion of an intracranial guide screw and stereotactic implantation of $5 \times 10^5$ U87MG-EGFRvIII cells. Whole brain paraffin embedded sections were analyzed by H&E. Immunohistochemistry was performed using anti-EGFR antibodies (Neomarkers), anti-Akt2 or anti-Ki67 (Santa Cruz) antibodies. M.O.M. for detecting mouse primary antibodies (Vector Laboratories) and developed with peroxidase substrate (Vector Laboratories). Total RNA was excised from tumor sections and analyzed by EGFRvIII TAQ-MAN probe.

Glioblastoma Longevity Model.

Intracerebral tumor bearing mice, inoculated on day 0, were untreated (n=10) or treated on 3, 8, 13 d with PBS (n=8), naked 600 pmol EGFRvlll+600 pmol Akt2 siRNA (n=8), PTD-DRBD plus 600 pmol Akt2+600 pmol control siRNA (n=8), PTD-DRBD plus 600 pmol EGFRvIII+600 pmol control siRNA (n=8), and PTD-DRBD plus 600 pmol EGFRvlll+ 600 pmol Akt2 siRNA (n=10) and assayed for survival.

In Vivo MRI.

Tumor bearing mice were treated on day 3, 8, 13 with PTD-DRBD plus negative control 1200 pmol control siRNA or PTD-DRBD plus 600 pmol EGFRvIII+600 pmol Akt2 siRNA. On 5 and 14 d, mice received 0.15 ml contrast agent (Multihance; Bracco Diagnostics) and were imaged using horizontal bore 7T GE MRI Machines (GE Medical Systems) with a 10 mm transmit/receive surface coil and image data obtained using a 3D FSPGR sequence. For 3D rendering, image data sets were semi-manually segmented using a threshold method, then volume and surface area rendered using AMIRA software (Mercury Computer Systems) to produce quantitative 3D models used to calculate tumor volume and surface.

In Vivo TUNEL Staining.

TUNEL assay was performed following the manufacturer's protocol (Roche Diagnostics, Indianapolis, Ind.) for paraffin-embedded tissue. Antigen retrieval was by Protease XXV (Lab Vision). TUNEL staining involved incubation for 1 h at 37° C. (using Boehringer Mannheim TUNEL enzyme and TUNEL label). Sections were counterstained using Hoechst stain (Molecular Probes), and fluorescence viewed on a confocal laser scanning microscope (Zeiss).

Statistical Analysis.

Data are expressed as mean±s.e.m., as indicated, and compared by two-tailed t tests. Statistical significance was assigned at $P<0.05$.

To determine the ability of PTD-DRBD fusion proteins to deliver siRNAs, a human H1299 lung adenocarcinoma dGFP/dDsRed reporter cell line was developed that allowed for direct determination of the magnitude of a single cell RNAi response and hence, the percentage of cells undergoing a RNAi response. H1299 dGFP/dDsRed reporter cells were treated with PBS (mock), PTD-DRBD plus control control (Con1, Con2) siRNAs or PTD-DRBD plus one of two sequence-independent GFP (GFP1, GFP2) siRNAs and analyzed by flow cytometry for GFP knockdown at 24 h (FIG. 1b, left panel).

Figure 5:
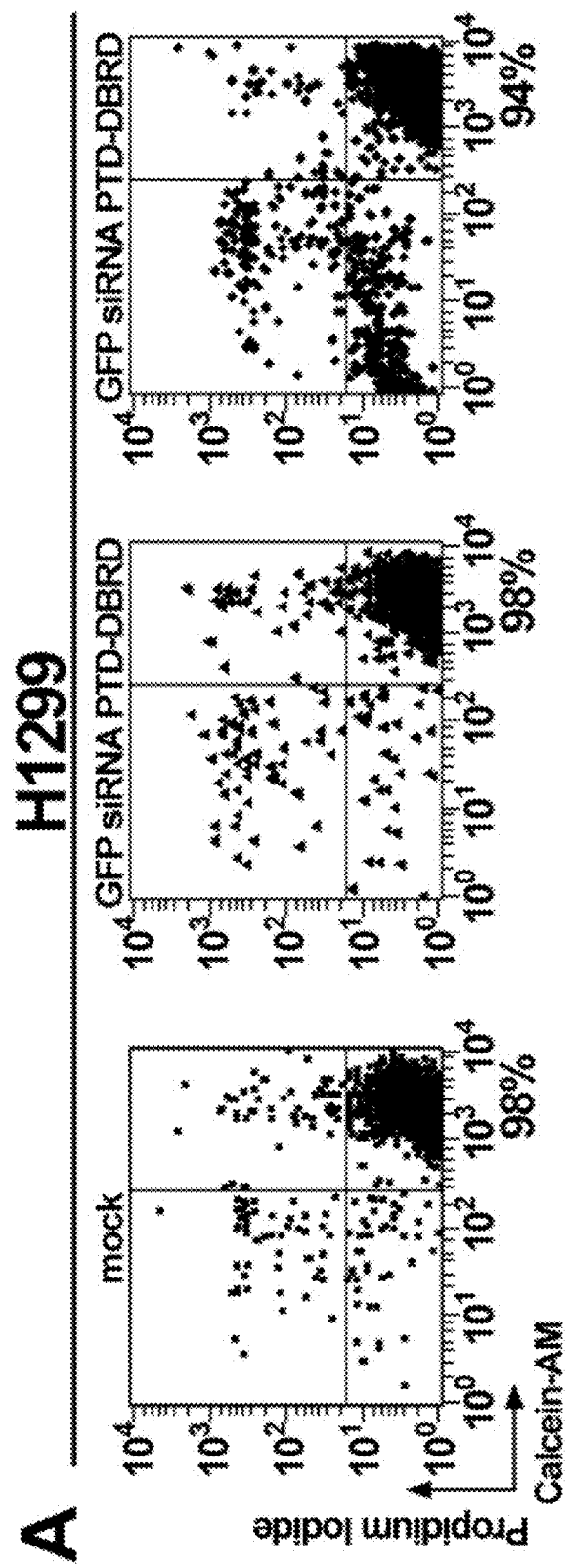
FIG. 5A-G shows PTD-DRBD siRNA delivery. (a) Cytotoxicity FACS analysis of cells treated with mock (PBS), GFP siRNA plus PTD-DRBD or lipofection with two independent means, propidium iodide and Calcein-AM. Percentage indicates percent of viable (live) cells in bottom right quadrant. (b, c) Single cell flow cytometry histogram analysis of dGFP RNAi response at 1 days post-treatment of THP-1 dGFP or B16F10 GFP cells, as indicated. (d-g) Flow cytometry analysis of dGFP RNAi knockdown decay kinetics following single siRNA treatment of dividing HFF, HaCAT or T98G dGFP cells, Jurkat T cells, as indicated using the legend in (b) above.
Figure 5:
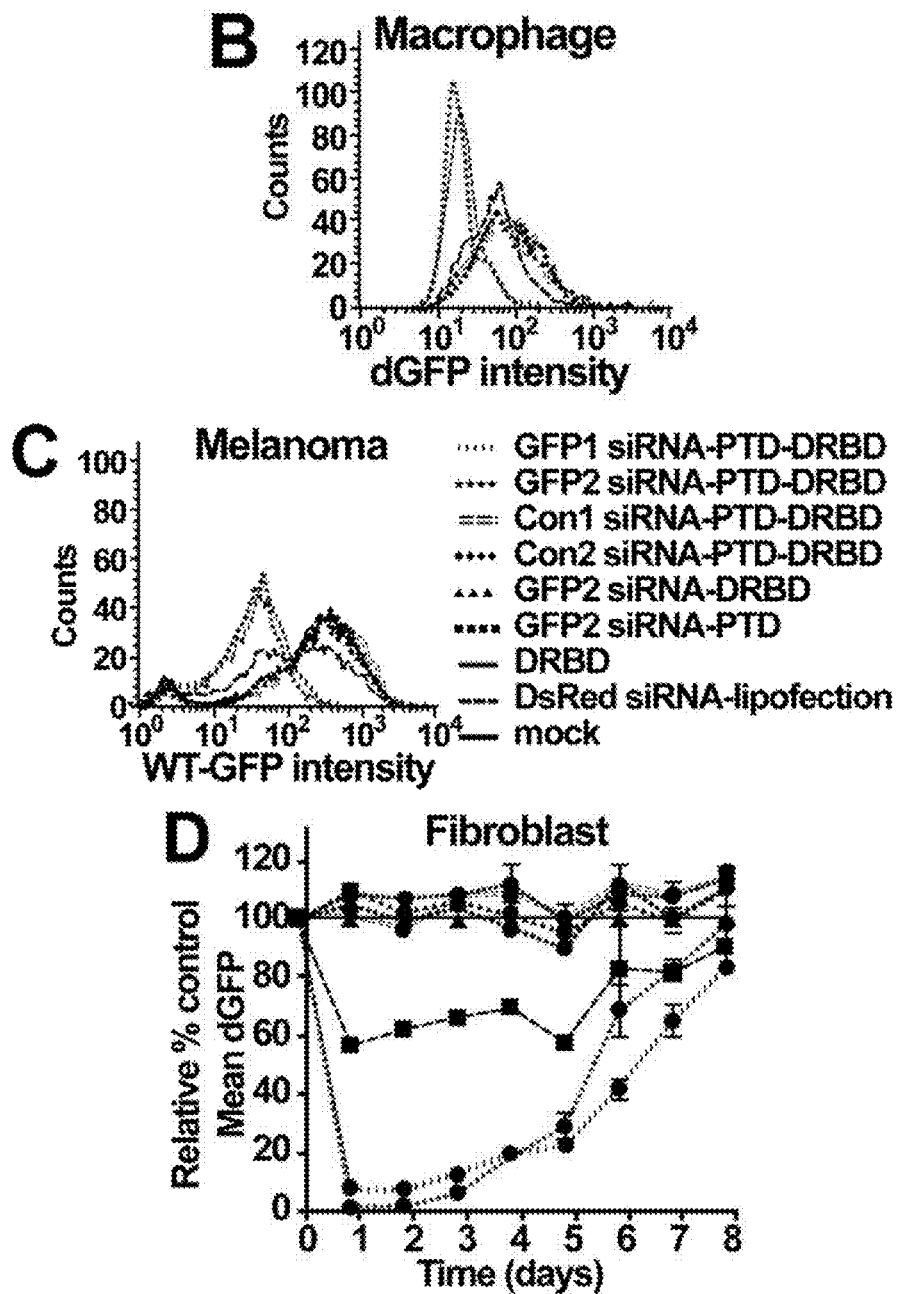
Figure 5:
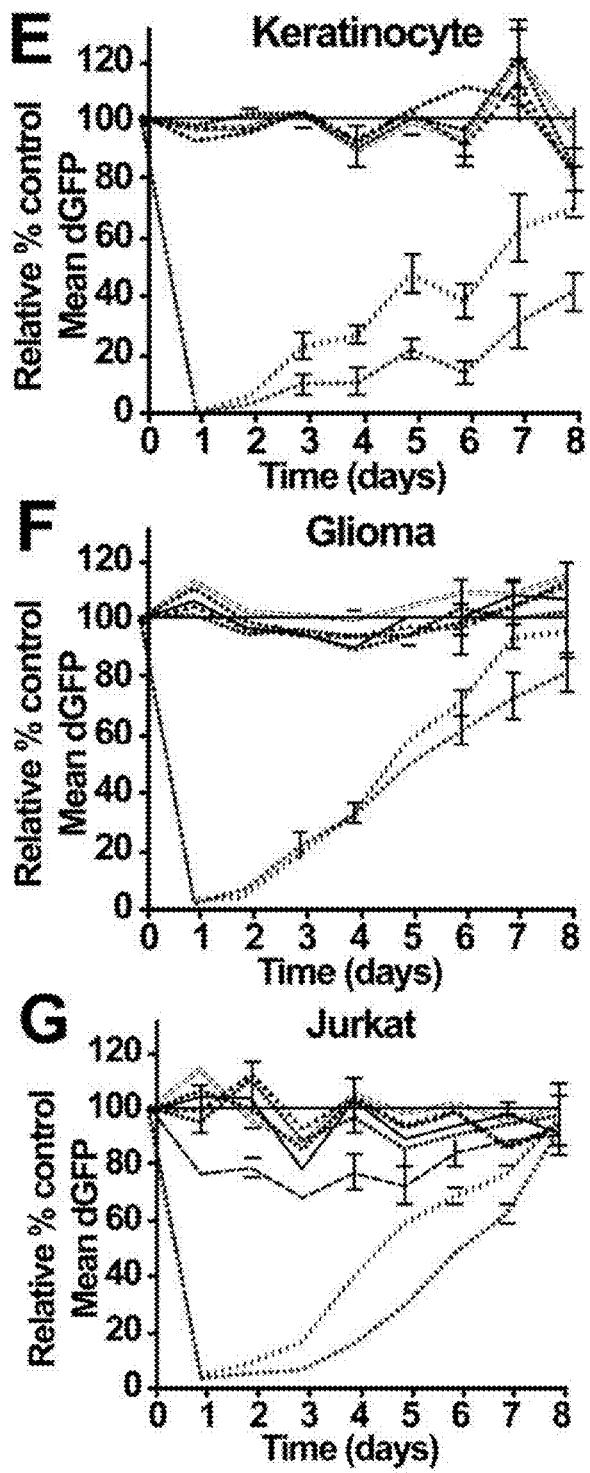

PTD-DRBD delivery of GFP specific siRNAs resulted in a significant GFP knockdown with little to no alteration of the internal DsRed control. Similar RNAi responses were induced with 3 additional GFP siRNAs delivered by PTD-DRBD. All controls (non-specific control siRNAs, PTD delivery peptide only) failed to induce a RNAi response. PTD-DRBD mediated siRNA delivery also resulted in a significantly stronger RNAi response compared to lipofection delivered siRNAs (FIG. 1b, right panel). Importantly, no alteration of cell viability were detected in PTD-DRBD:siRNAs treated cells, whereas lipofection resulted in varying levels of cytotoxicity (FIG. 5). Single cell flow cytometry analysis of PTD-DRBD:GFP siRNA treated cells showed that the entire cellular population was undergoing a maximal RNAi response at 24 h that was maintained at 48 h (FIG. 1c,d). In contrast, lipofection delivered siRNAs induced a partial penetrant RNAi response with ~20% of cells unresponsive (FIG. 1c,d). Kinetic analysis over 8 days in dividing H1299 cells showed a slow decay of the RNAi response starting 3 days after PTD-DRBD:GFP siRNA treatment that was similar to the lipofection mediated RNAi decay kinetics (FIG. 1e). Similar results were obtained in primary human fibroblasts, keratinocytes, macrophage, melanoma and glioma cells containing integrated dGFP reporter genes (FIG. 5). To circumvent the RNAi decay curve, re-treated dividing H1299 cells on days 3 and 6 with PTDDRBD:GFP siRNAs resulting in maintenance of the extent and magnitude of the GFP RNAi response (FIG. 1f).

Endogenous GAPDH mRNA was targeted by PTD-DRBD mediated RNAi. Treatment of H1299 cells with one of two sequence-independent GAPDH siRNAs delivered by PTD-DRBD resulted in a GAPDH RNAi response that was first detected by qRT-PCR at 6 h post-addition and reached a maximal RNAi response by 12 h (FIG. 1g,h). In contrast, all PTD-DRBD negative controls failed to induce a GAPDH RNAi response. Impressively, PTD-DRBD mediated delivery of GAPDH1 siRNA resulted in a near maximal RNAi response by 6 h, significantly ($P<0.001$) earlier than control lipofection delivery of the same GAPDH siRNAs (FIG. 1g), suggesting that PTD-DRBD delivered siRNAs rapidly enter the cytoplasm and are loaded into RISC.

To determine if PTD-DRBD mediated siRNA delivery caused any cellular alterations, the transcriptome of treated cells was examined. Whole genome microarrays were probed with total mRNA from PTD-DRBD GAPDH siRNA treated H1299 cells at 12 h and 24 h (FIG. 1i). Using a 1.6× fold increase/decrease filter (blue line) of cellular mRNAs, a dramatic reduction in the target GAPDH mRNA was detected along with a limited number of both up and down regulated genes. The up regulated genes were reduced in numbers and to nearly background 1.6× levels at 24 h, while the down regulated genes increased slightly in numbers and maintained a similar magnitude at 24 h (FIG. 1i). None of these genes are present in either an innate immune response pathway or congregate into a specific genetic pathway. In contrast, lipofection treated cells showed both a dramatic increase in both the total number of genes altered and the magnitude of the increase (FIG. 1j). In addition, the numbers of genes affected increased between 12 h and 24 h, suggesting that lipofection of siRNAs into cells results in a substantial alteration to the transcriptome and may thereby caveat interpretation of experimental outcomes. Moreover, lipofection mediated GAPDH specific knockdown was significantly smaller than PTD-DRBD mediated knockdown. Taken together, these observations demonstrate that PTD-DRBD mediated siRNA delivery efficiently targets the entire cellular population in the absence of cytotoxicity.

Figure 2:
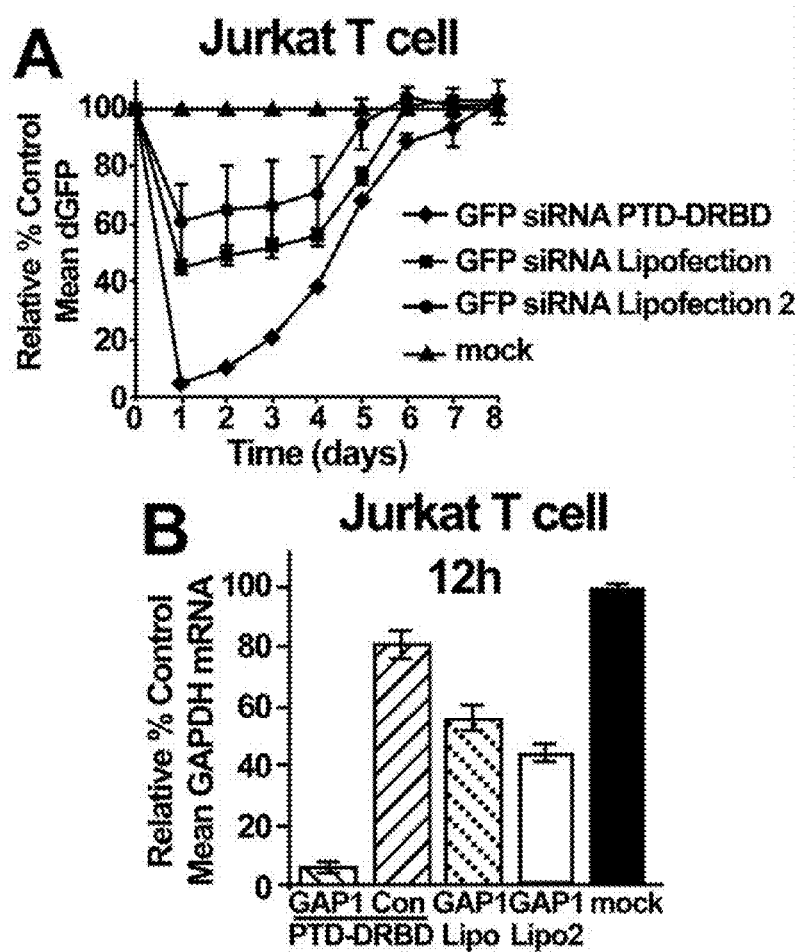
FIG. 2A-F shows PTD-DRBD siRNA delivery into T Cells and HUVECs. (a) Flow cytometry analysis of dGFP RNAi knockdown decay kinetics of dividing Jurkat dGFP cells following treatment with GFP2 siRNA plus PTD-DRBD, Lipofection-2000 (Lipofection) or RNAiMAX (Lipofection 2), as indicated. (b) Quantitative RT-PCR analysis of endogenous GAPDH mRNA expression at 12 h post-treatment of GAPDH siRNA or GFP2 (Con) siRNA plus PTD-DRBD, GAPDH siRNA plus Lipofection-2000 (Lipofection) or RNAiMAX (Lipofection 2) in Jurkat cells, as indicated. Mean values normalized to β2 microglobulin and reported as percent of mock GAPDH control. (c) Flow cytometry histogram analysis of PTD-DRBD mediated CD4 or CD8 RNAi response at 1 day post-treatment of mouse primary T cells, as indicated. (d) Quantitative RT-PCR analysis of endogenous CD4, CD8 or CD90 mRNA expression at 12 and 24 h post-treatment of PTDDRBD CD4 or CD8 siRNAs in primary T cells, as indicated. Mean values normalized to β2 microglobulin and reported as percent of mock control. *($P<0.05$) of specific siRNA vs. control siRNA delivered by PTD-DRBD. (e) Quantitative RT-PCR analysis of endogenous GAPDH mRNA expression at 6, 12, and 24 h post-treatment of PTD-DRBD GAPDH or control siRNAs in primary HUVEC cells, as indicated. Mean values normalized to β2 microglobulin and reported as percent of mock GAPDH control. **($P<0.01$) of specific siRNA vs. control siRNA delivered by PTD-DRBD. (f) PTD-DRBD cytotoxicity analysis. HUVEC cells were treated with mock (PBS), GAPDH siRNA plus PTD-DRBD or lipofection and analyzed for cytotoxicity by FACS after 24 h post-treatment with two independent means, propidium iodide and Calcein-AM. Percent indicates viable cells present in bottom, right quadrant.
Figure 2:
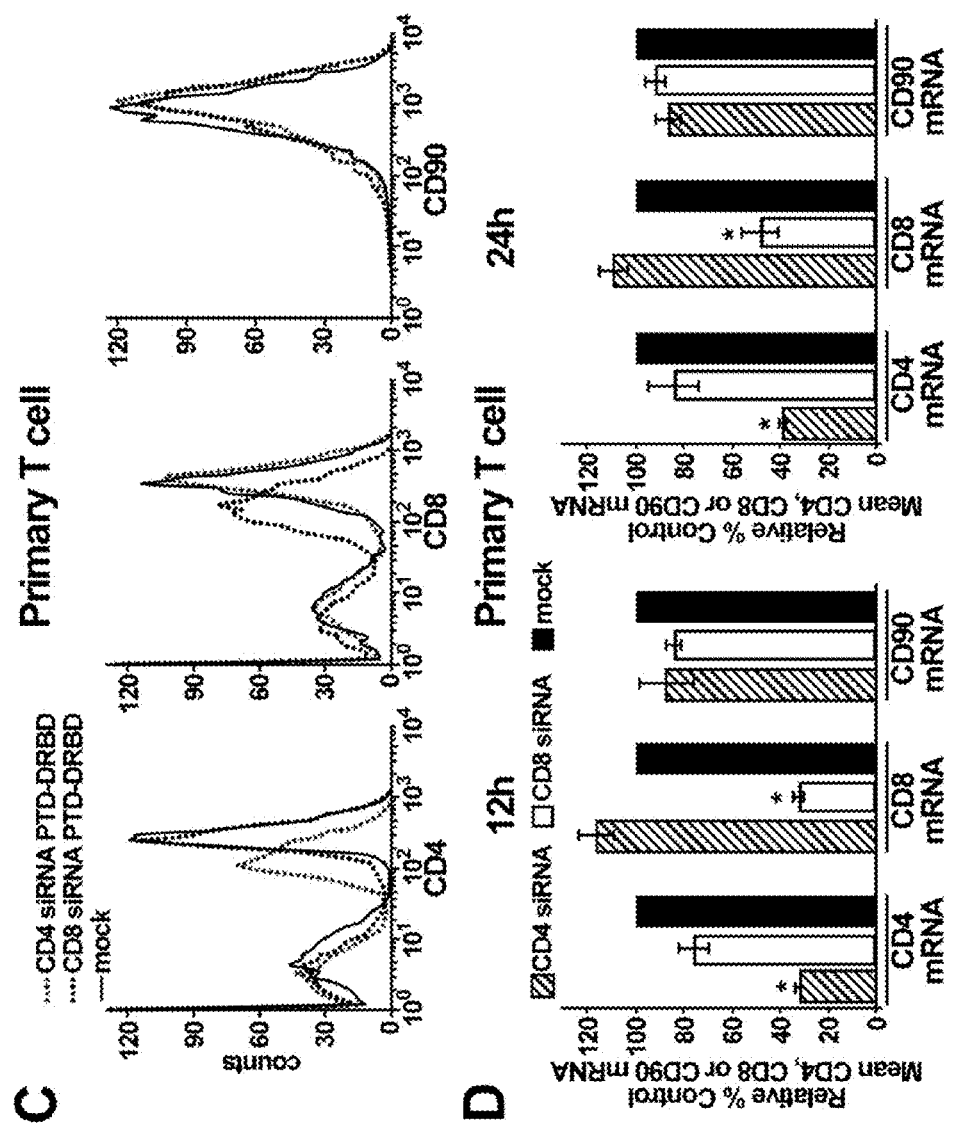
Figure 2:
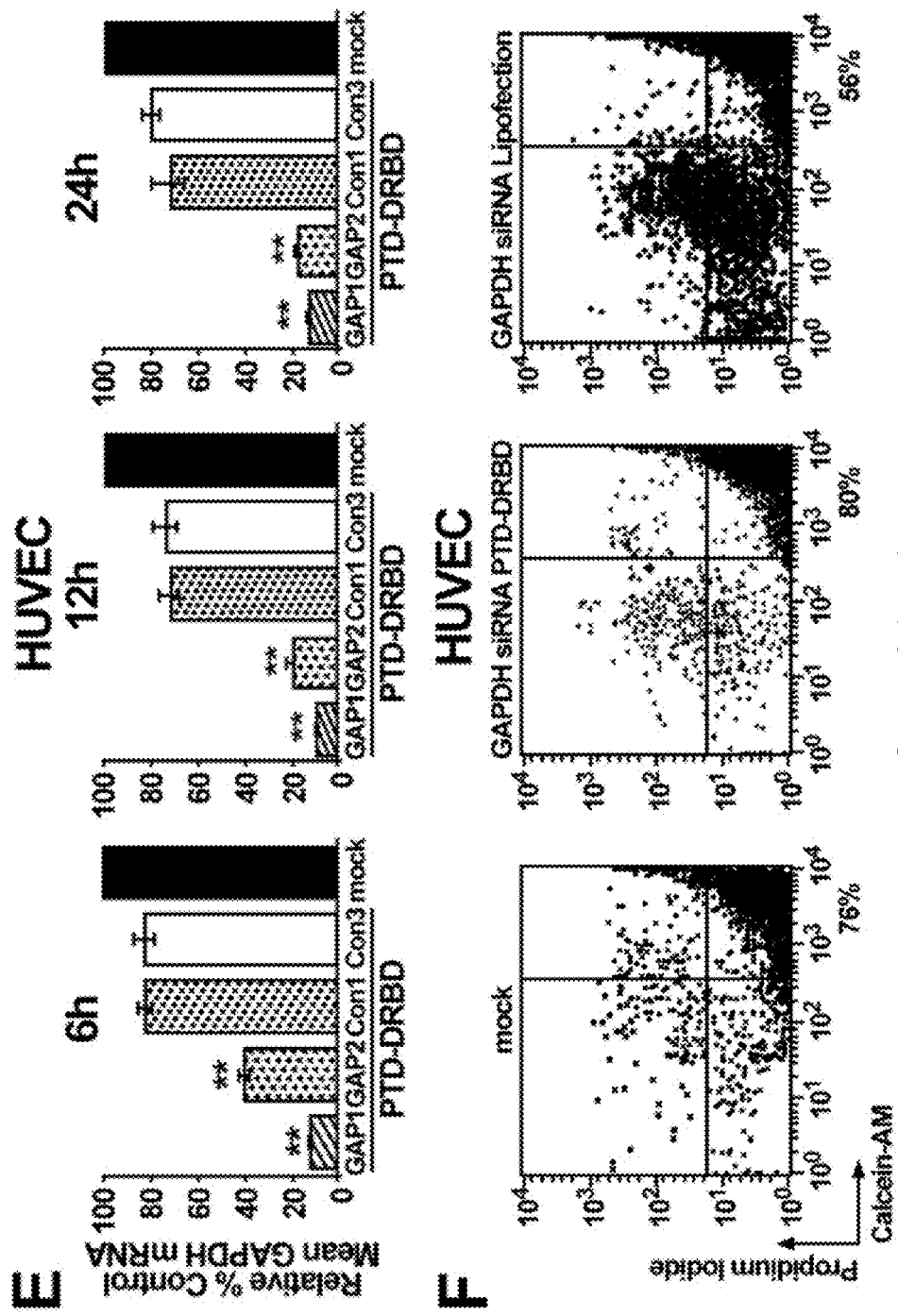

Due to inefficient siRNA delivery and associated cytotoxicities, RNAi manipulation of T cells remains problematic. Therefore, a notoriously difficult cell type to delivery siRNAs into, namely tumorigenic Jurkat T cells, was examined. Jurkat T cells containing an integrated GFP reporter gene were treated with GFP siRNA plus either PTD-DRBD or one of two lipofection reagents (Lipofection-2000 and RNAiMAX) at optimal concentrations and analyzed by flow cytometry for GFP knockdown at various time points (FIG. 2a). PTD-DRBD delivery of GFP specific siRNAs into Jurkat T cells resulted in a strong GFP RNAi response in the entire population of Jurkat T cells. In comparison, both lipofection reagents induced limited RNAi responses. Moreover, PTD-DRBD delivered GAPDH siRNA into Jurkat T cells resulted in a strong GAPDH RNAi response as measured by qRT-PCR, whereas the two lipofection reagents performed poorly (FIG. 2b). Primary murine T cells with PTD-DRBD plus CD4 specific siRNAs were treated and assayed for CD4 cellular levels by flow cytometry (FIG. 2c, left panel). The entire CD4 cellular population had undergone an RNAi response at 24 h, whereas control siRNAs did not alter CD4 levels. Similarly, PTD-DRBD mediated delivery of CD8 specific siRNAs into primary T cells resulted in a CD8 specific RNAi response with no change in CD4 levels (FIG. 2c, middle panel). Consistent with these observations, PTD-DRBD CD4 and CD8 specific RNAi responses were detected by qRT-PCR at 12 and 24 h ($P<0.01$) (FIG. 2d). Importantly, both flow cytometry and qRT-PCR analyses of internal control CD90 receptor showed little to no alteration in either PTD-DRBD CD4 or CD8 siRNA treated T cells (FIG. 2c,d).

In contrast, no RNAi responses were detected by lipofection of primary T cells.

Primary human umbilical vein endothelial cells (HUVEC) are an important cell type for large scale RNAi screen; however, lipofection delivery of HUVECs results in both poor siRNA delivery and cytotoxicity. Endogenous GAPDH mRNA was targeted by PTD-DRBD mediated RNAi. Treatment of primary HUVECs with one of two sequence-independent GAPDH siRNAs delivered by PTD-DRBD resulted in a GAPDH RNAi response that was first detected by qRT-PCR at 6 h post-addition and reached a maximal RNAi response by 12 h (P<0.01) (FIG. 2e). In contrast, all PTD-DRBD negative controls failed to induce a GAPDH RNAi response. Consistent with the observations in H1299 cells above, PTD-DRBD mediated delivery of GAPDH1 siRNA resulted in a maximal RNAi response by 6 h (FIG. 2e). Importantly, little to no alteration of HUVEC cell viability was detected in PTD-DRBD:siRNA treated cells compared to mock treated control cells (FIG. 2f). In contrast, siRNAs were unable to be lipfected into HUVECs without inducing significant levels of cytotoxicity (FIG. 2f).

Figure 3:
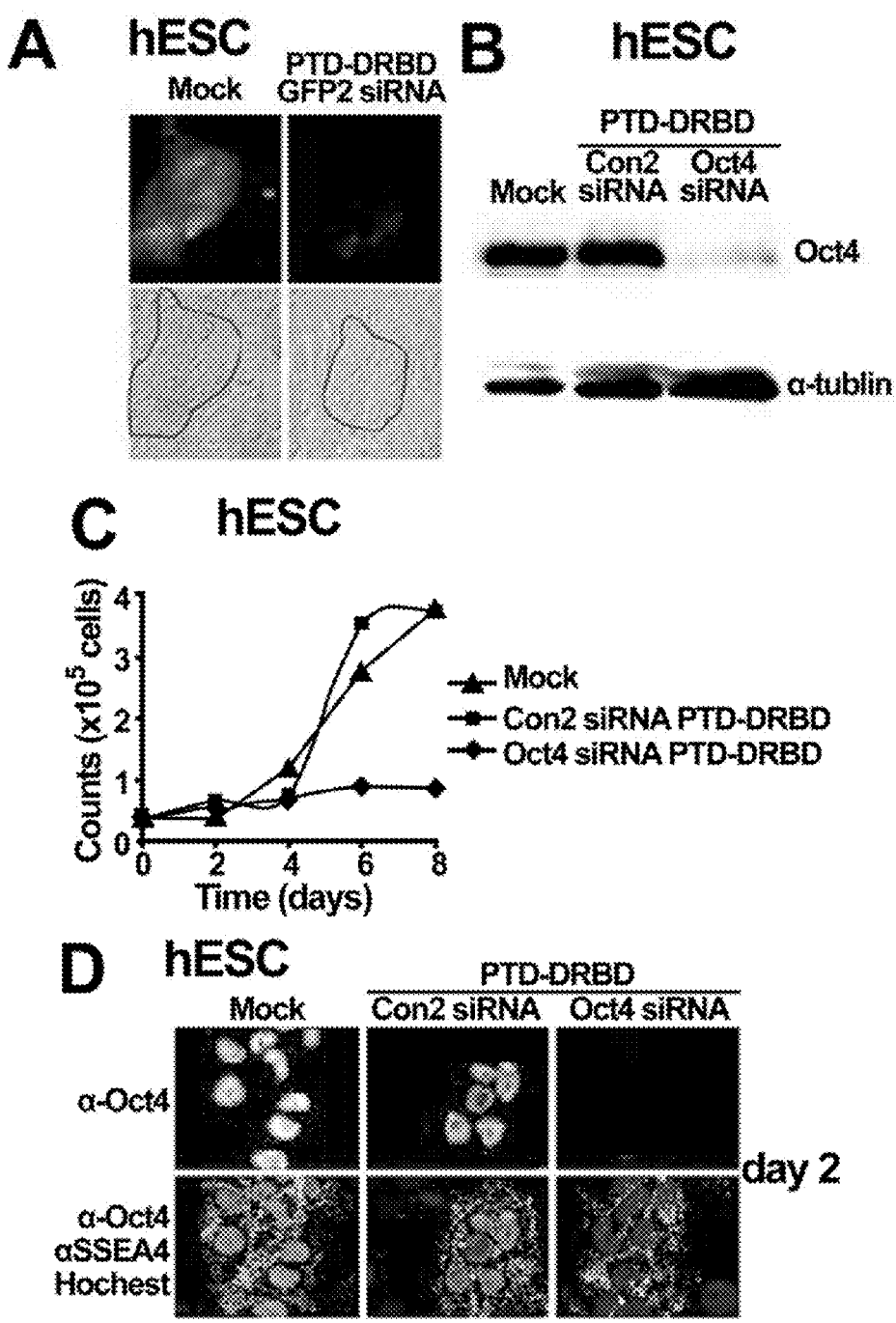
FIGS. 3A-I shows PTD-DRBD mediated RNAi Responses. (a) Fluorescent microscopy analysis of H9 hESCs constitutively expressing GFP treated with PTD-DRBD delivered GFP2 siRNA at 2 days post-addition. Black line outlines hESC colony on mouse feeder cell background. (b) Oct4 immunoblot analysis in HUES9 hESCs treated with mock (PBS), PTD-DRBD delivered Oct4 or control siRNAs at 2 days post-addition. (c) Cell division curve of human HUES9 embryonic stem cells treated with mock (PBS), PTD-DRBD delivered Oct4 or control siRNAs, as indicated. (d) Immunohistochemistry analysis of Oct4 and SSEA4 expression in HUES9 hESCs at 2 days post-treatment with mock (PBS), PTD-DRB delivered Oct4 or control siRNAs. Anti-Oct4 antibodies, anti-SSEA-4 antibodies (green), genomic DNA. (e) Immunohistochemistry analysis of GATA6 and SSEA4 expression in HUES9 hESCs at 10 days posttreatment with mock (PBS), PTD-DRB delivered Oct4 or control siRNAs. Anti-GATA6 antibodies, anti-SSEA-4 antibodies, genomic DNA. (f, g) Analysis of IFN-α and TNF-α induction in human PBMCs at 4 or 24 h post-treatment with mock (PBS), β-gal siRNA plus PTD-DRBD or plus Lipofection, as indicated. 10 μg/ml Imiquimod Imiquimod or 10 μg/ml LPS was used as a positive control for IFN-α or TNF-α, respectively. (h) Nasal and tracheal expressing ROSA26R-Luciferase transgenic mice were live animal imaged on day 0. Randomized groups of luciferase expressing mice were then treated with PBS, PTD-DRBD plus Luc siRNA or control GFP (Con) siRNA and monitored daily for luciferase expression, as indicated. Scale is in photons/s/cm2/sr. (i) Graph of percent Luciferase knockdown mice from (h) above. Luciferase expression was normalized to mock each day, error bar indicates s.e.m., n=3 for each group with two luciferase readings performed per mouse per day.
Figure 3:
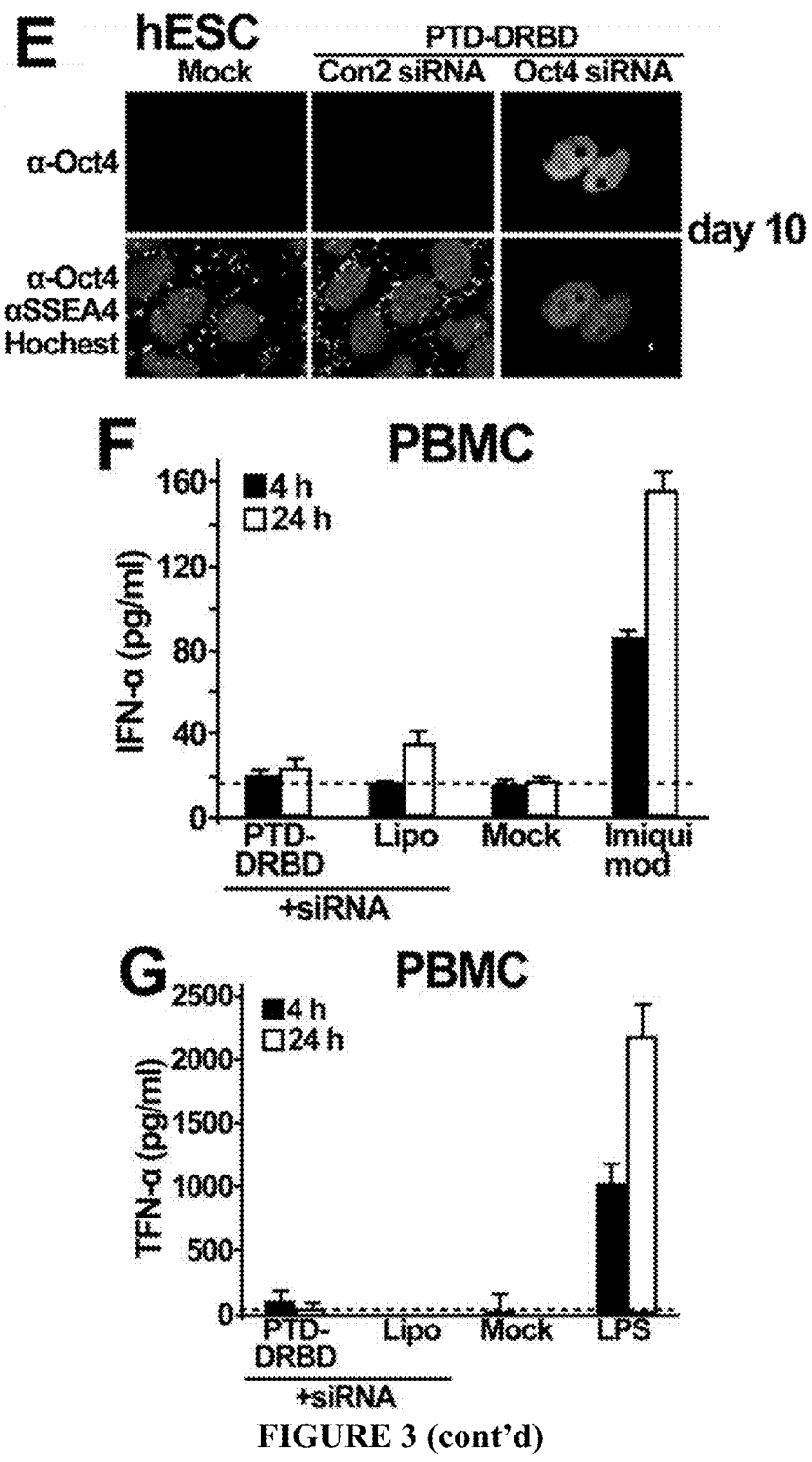
Figure 3:
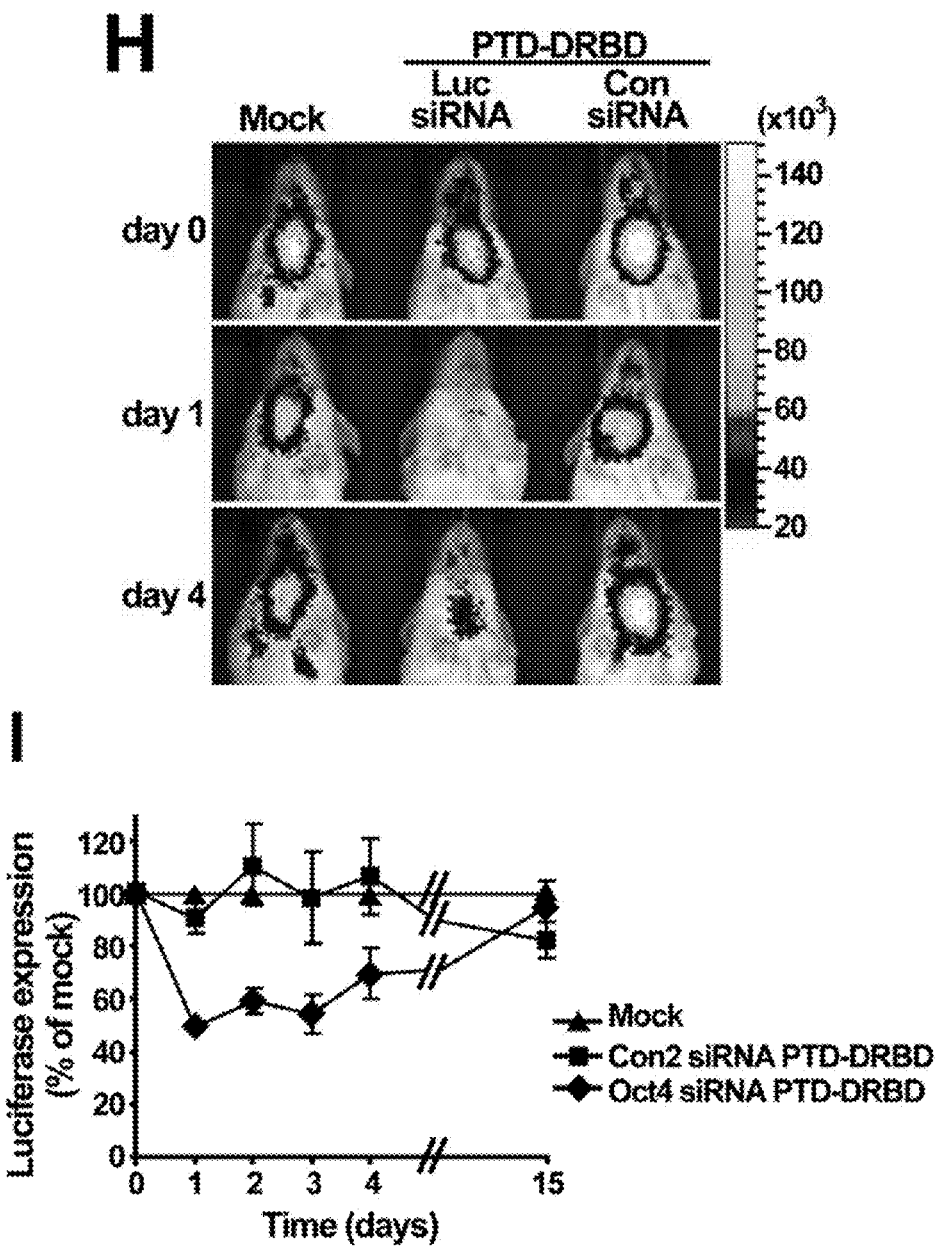

Human Embryonic Stem Cells (hESCs) have great potential to treat human disease 14; however, manipulation of hESCs into specific cell lineages by RNAi requires protocols that target the entire cell population in a non-cytotoxic manner. Thus, the ability of PTD-DRBD to deliver siRNAs into H9 hESCs stably expressing GFP was examined. Consistent with the observations above, PTD-DRBD mediated delivery of GFP siRNAs induced a marked GFP RNAi response throughout the hESC colony (FIG. 3a, circled area). The ability of PTD-DRBD mediated siRNA delivery to affect the fate of hESCs was also examined. The Oct4 (POU5F1) transcription factor is required to maintain hESC pluripotency and Oct4 RNAi knockdown results in hESC cell cycle exit and differentiation. Treatment of HUES9 hESCs with PTD-DRBD plus Oct4 siRNA resulted in both an Oct4 specific knockdown followed by a reduced growth rate and cell cycle exit indicative of pluripotency loss and initiation of differentiation (FIG. 3b,c). In contrast, both mock and PTD-DRBD plus control siRNA did not alter hESC cellular morphology, growth kinetics or Oct4 expression levels.

Pluripotent hESCs express multiple cell surface markers, including Stage-Specific Embryonic Antigen-4 (SSEA-4)15. During differentiation into endoderm, hESCs decrease SSEA-4 expression, stop dividing, increase in size and subsequently express the GATA6 differentiation transcription factor. PTD-DRBD delivered Oct4 siRNA resulted in loss of Oct4 expression by day 2 with continued SSEA-4 expression (FIG. 3d). However, by 10 days post-treatment, Oct4 siRNA treated cells had lost expression of SSEA-4 and induced expression of the GATA6 endoderm specific transcription factor (FIG. 3e). In contrast, mock and PTD-DRBD plus control siRNA treated hESCs did not induce differentiation or alter hESC marker expression. Similar results were obtained by simultaneous PTD-DRBD mediated knockdown of Oct4 and Nanog.

siRNAs have been shown to stimulate activation of Toll-Like Receptors-3, -7, -8 (TLR) to induce innate immune responses. However, PTD-DRBD mediated delivery of immunostimulatory siRNAs failed to activate IFN-α or TNF-α responses in primary human peripheral blood mononuclear cells (PBMCs) above background levels (FIG. 3f,g). Taken together, these observations demonstrate the ability of PTD-DRBD to deliver siRNA and rapidly induce RNAi responses in three important and difficult to deliver cell types: T cells, HUVECs, and hESCs.

siRNA-induced RNAi has great potential to treat human disease, including nasal delivery to treat virus infection 18; however, in vivo siRNA delivery remains problematic. Based on the efficient PTD-DRBD mediated siRNA delivery observed in primary cell culture systems, the ability of PTD-DRBD to deliver siRNAs and induce an RNAi response using an intranasal in vivo transgenic Luciferase reporter mouse model was examined. Transgenic ROSA26 mice stably expressing tissue restricted luciferase in the nasal and tracheal passage were live animal imaged for Luciferase expression then randomized into groups (FIG. 3h,i). Luciferase mice were then treated intranasally with PBS, PTD-DRBD plus Luc siRNA or control siRNA and monitored daily for 15 days for luciferase expression. Control PBS and PTD-DRBD control siRNA mice showed no change in luciferase expression over the course of the experiment. In contrast, PTD-DRBD delivered Luc siRNA showed extensive reduction of luciferase expression throughout the nasal and trachea at day 1 and gradually recovered luciferase expression by day 15 (FIG. 3h,i). These observations demonstrate the ability of PTD-DRBD mediated siRNA delivery to induce a specific RNAi response to a quantifiable target protein in reporter mouse models in vivo.

siRNA induced RNAi responses are a key experimental procedure for manipulation of cell biology, dissection of genetic pathways, target validation and have great potential for therapeutic intervention. However, due to their macromolecular size (14,000 Da) and strong anionic charge, siRNAs have limited to no ability to enter cells on their own, even at millimolar concentrations. Indeed, siRNA delivery has become the rate-limiting barrier to efficient cell culture, pre-clinical and clinical usage of siRNA therapeutics. Consequently, significant effort has been placed on devising efficient siRNA delivery approaches. While current siRNA delivery approaches have merit, they generally fail to target the entire population of cells or a high percentage of cells, especially primary cells, and often result in varying levels of cytotoxicity and alterations in cell biology. In contrast, the PTD-DRBD siRNA delivery approach described here fulfills many of the criteria for an efficient siRNA delivery system into primary cells. PTD-DRBD delivered siRNAs and induced RNAi responses in the entire population of three difficult to deliver primary cell types (T cells, HUVECs, and hESCs) in a rapid and non-cytotoxic fashion. DRBDs bind to dsRNAs (siRNAs) independent of sequence composition and therefore, in theory, PTD-DRBD can deliver any siRNA into cells. Lastly, the intranasal knockdown of luciferase in vivo begins to demonstrate an in vivo potential of PTD-DRBD mediated siRNA delivery; however, significantly more in vivo work needs to be performed to ascertain the full extent of in vivo utility. In summary, PTD-DRBD has broad implications for the scientific community in RNAi basic research, target screening and potential therapeutic applications.

The rate-limiting steps for PTD-DRBD mediated siRNA delivery is 1) release from the PTD-DRBD and 2) escape from the endosomal vesicle. To enhance PTD-DRBD release, hisitidine modifications were inserted into the DRBD of PTD-DRBD thereby making the DRBD more pH sensitive due to the insertion of Histidine residues into non-conserved areas of the DRBD. Three constructs showing enhanced RNAi activity were tested:

Construct #2. His substitutions at positions V24H/K26H
Construct #6. His substitutions at positions F52H/E54H
Construct #7. His substitutions at positions N65H/A66H To enhance escape, 12× Histidine residues were added to the C-terminus of PTD-DRBD (the original had 6× Histidines). This resulted in a dramatic increase in siRNA escape and subsequent RNAi response likely due to increased swelling and subsequent bursting of the vesicle due to the proton sponge effect of Hisitidine.

Figure 6:
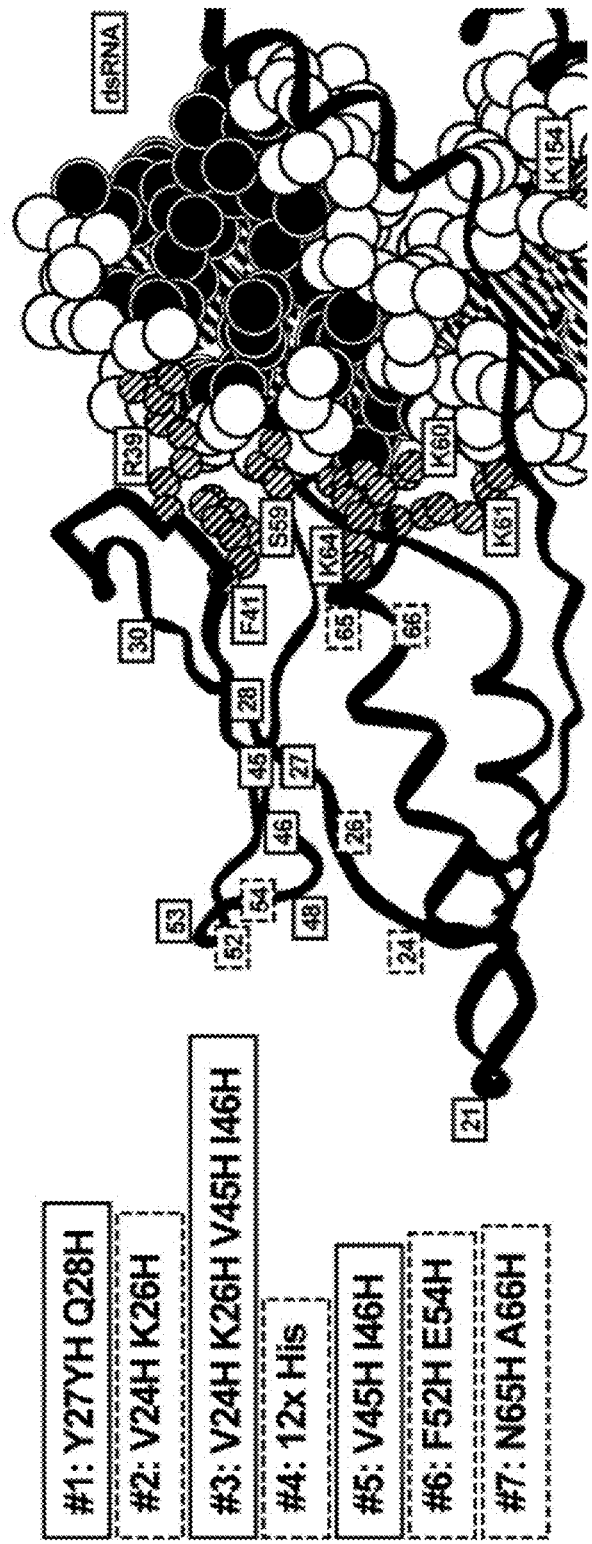
FIG. 6 shows constructs and ribbons of a mDRBD of the disclosure. Histidine codons were inserted into non-conserved areas of the dsRNA Binding Domain (DRBD) cDNA as indicated. The new PTD-DRBD protein was expressed in E. coli, purified, loaded with GFP siRNA and assayed for ability to induce RNAi responses.
Figure 7:
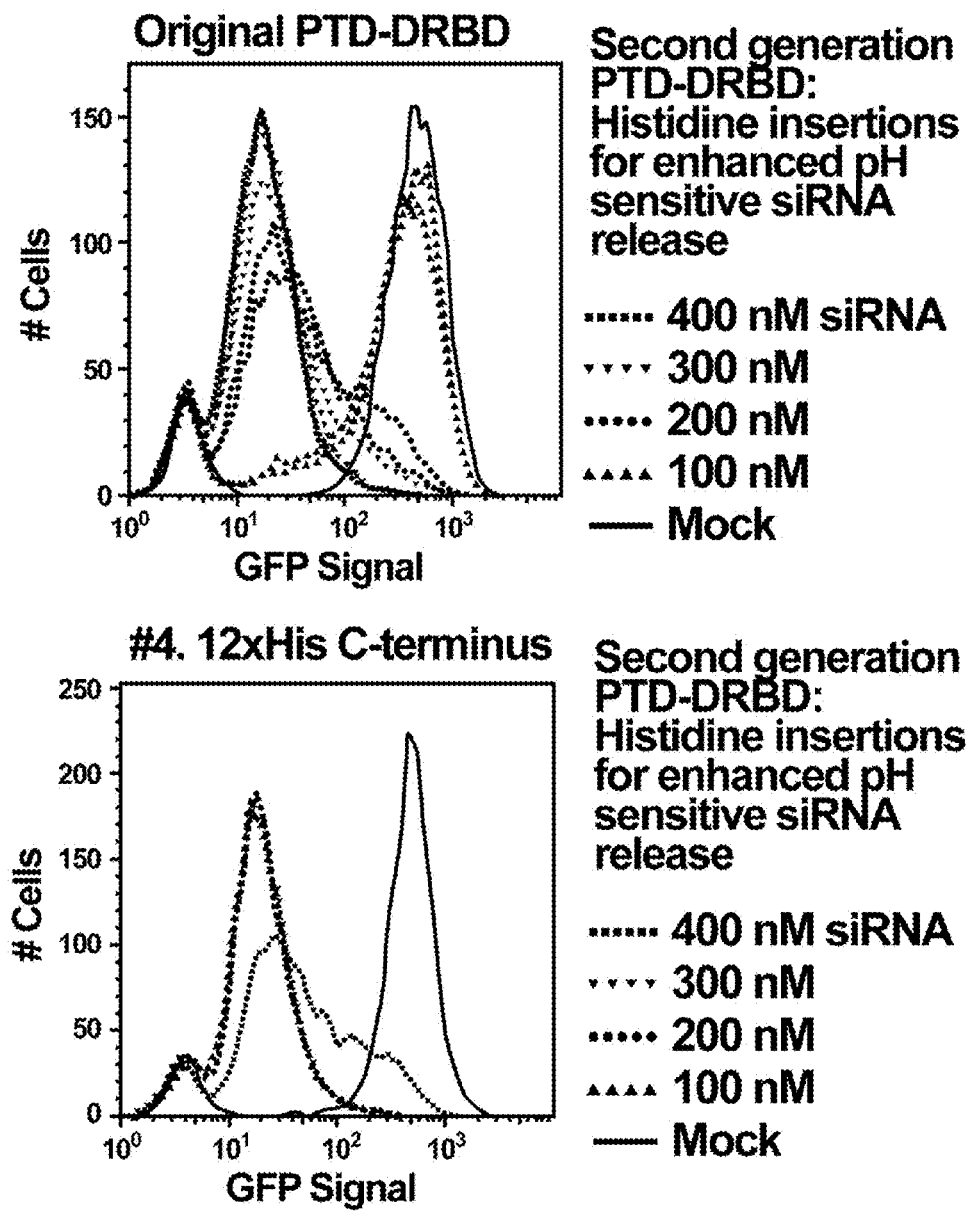
FIG. 7 shows the effect of the various constructs of FIG. 6 on siRNA release.
Figure 7:
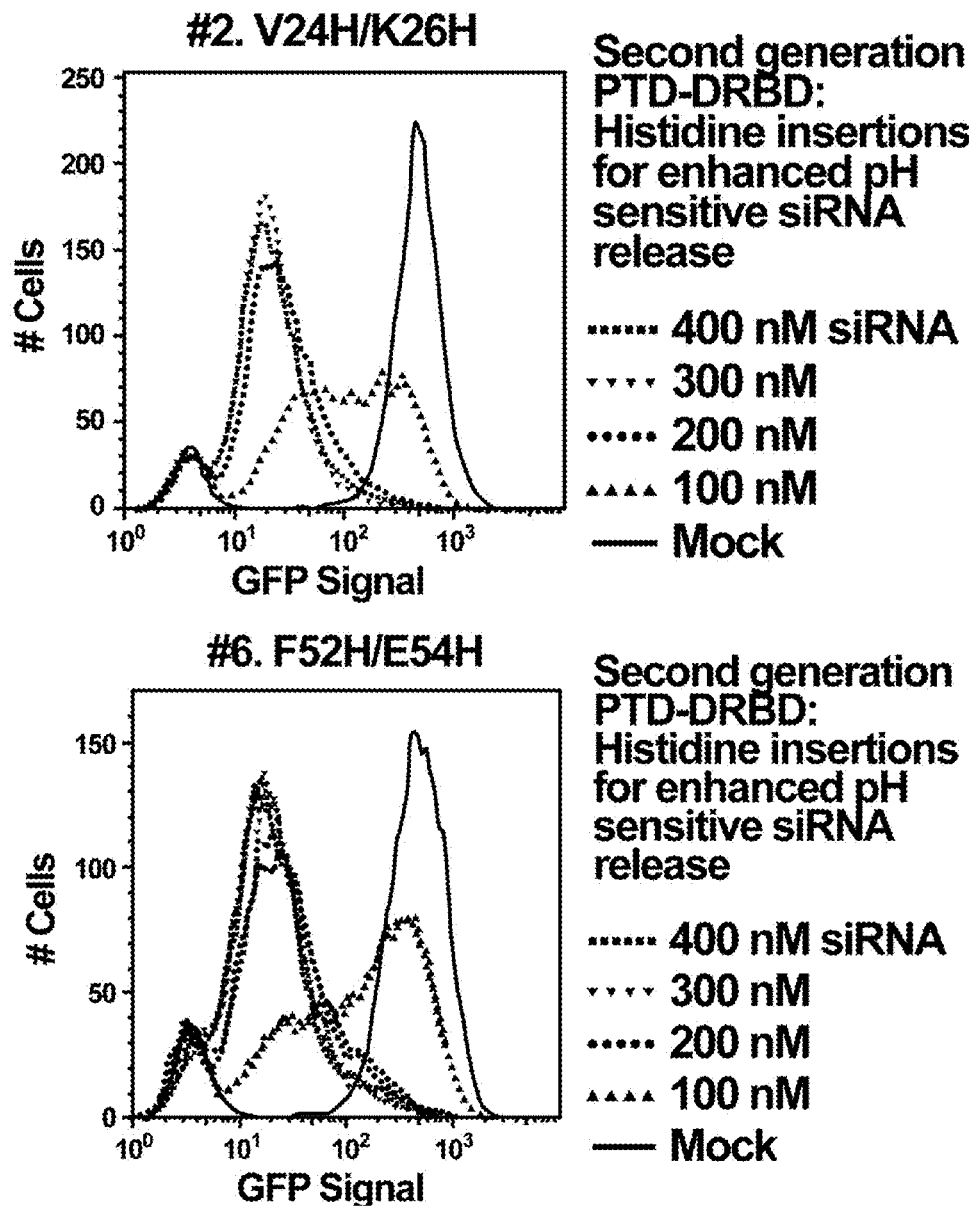
Figure 7:
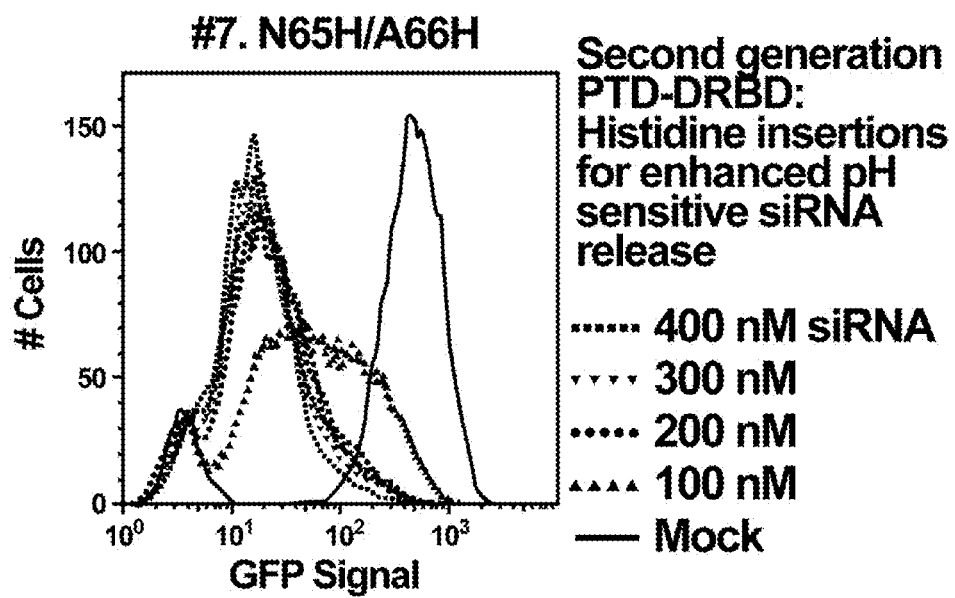

Construct #4. 12×His at C-terminus. (see FIGS. 6 and 7).

Figure 8:
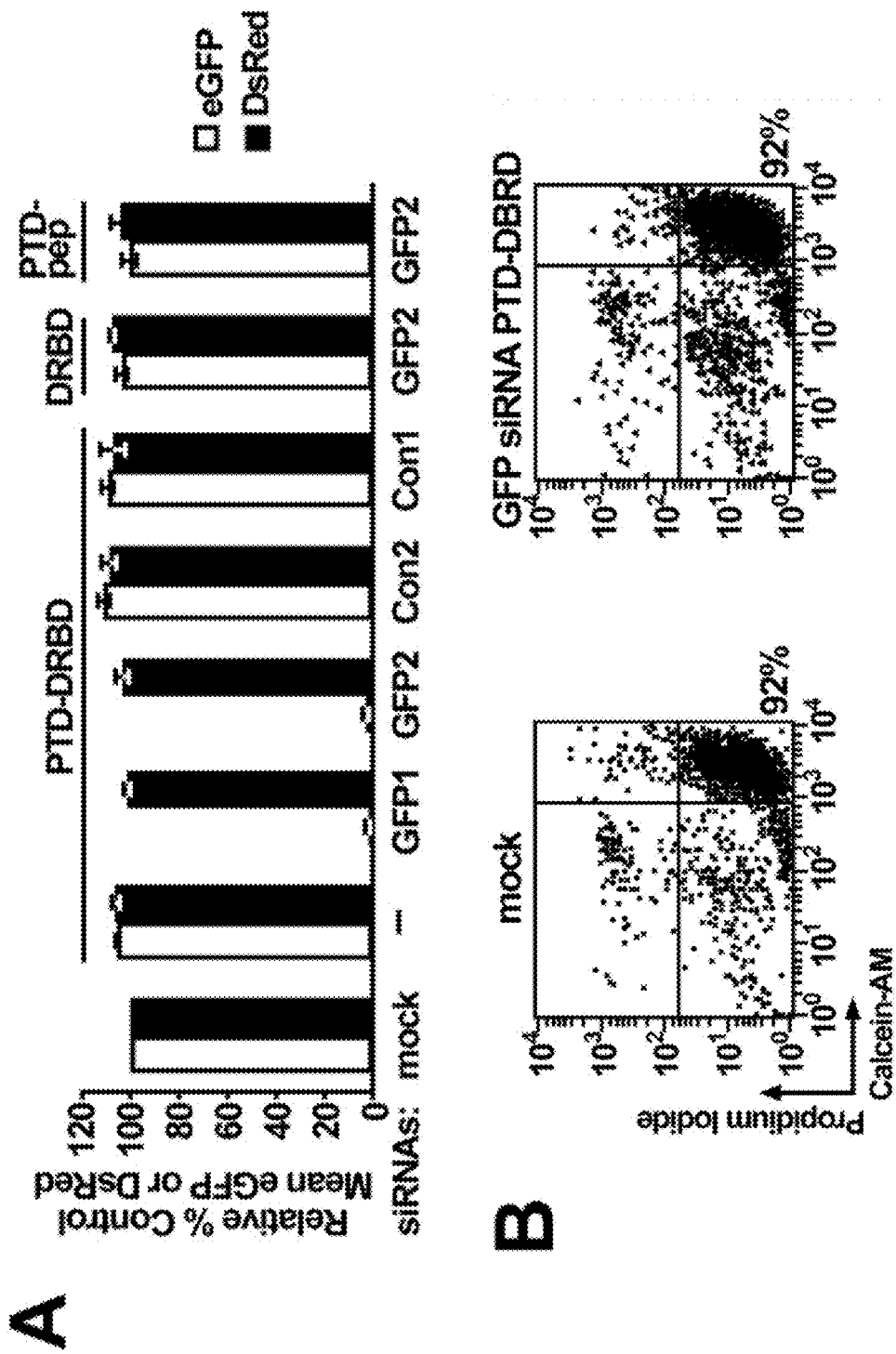
FIG. 8A-F shows PTD-DRBD mediated siRNA delivery into human T98MG glioblastoma cells. (A) Normalized RNAi knockdown of dGFP in T98MG cells constitutively co-expressing integrated destabilized dGFP and dDsRed reporter genes by PTD-DRBD, control PTD peptide, control DRBD plus siRNA, as indicated. GFP1/GFP2, sequence independent GFP siRNAs; SN, control Silencer Negative siRNA; Luc, control GL3 siRNA. (B) PTD-DRBD cytotoxicity analysis at 24 h post-treatment using two independent means, Calcein-AM (x-axis) and propidium iodide (y-axis) flow cytometry analysis, bottom-right quadrant represents viable cells. (C) Single cell flow cytometry histogram analysis of PTD-DRBD dGFP RNAi response 1 d post-treatment, as indicated. (D) Flow cytometry analysis of dGFP RNAi knockdown decay kinetics following single PTD-DRB siRNA treatment of dividing T98MG cells and (E) following multiple PTD-DRB siRNA treatments, as indicated. (F) Quantitative TaqMan RT-PCR analysis of endogenous GAPDH mRNA expression at 6 and 12 h post-addition of PTD-DRBD siRNAs, as indicated. Mean values are normalized to mock percent control, error bar indicates s.d., all experiments performed in triplicate.
Figure 8:
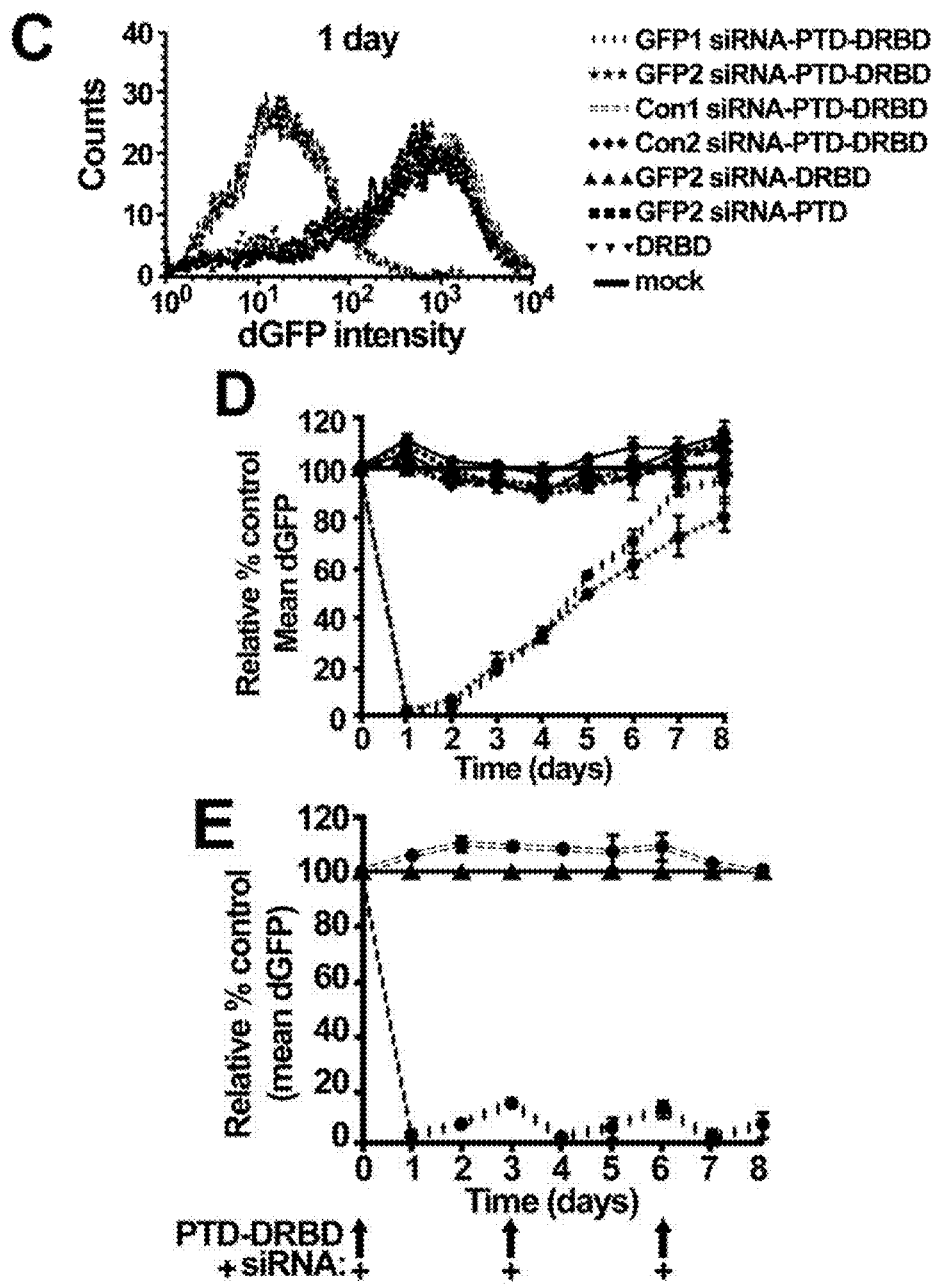
Figure 8:
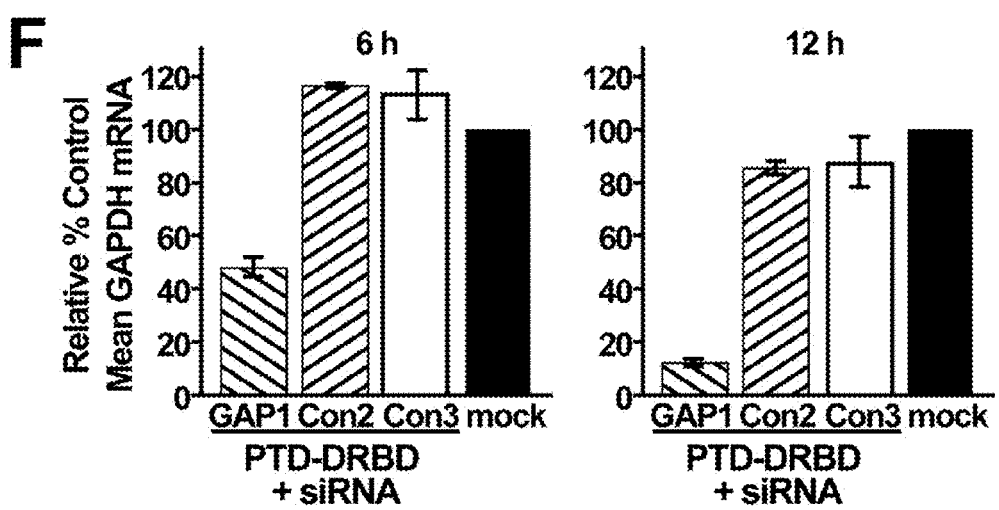
Figure 9:
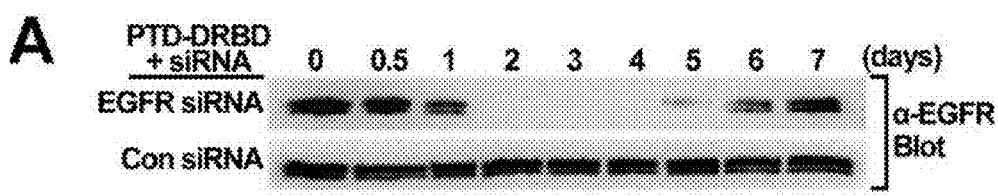
FIG. 9A-D shows synergistic effect of PTD-DRBD mediated knockdown of EGFR and Akt targets in human U87MG-EGFRvIII glioblastoma cells. (A) Anti-EGFR immunoblot analysis of U87MG-EGFRvIII cells treated with PTD-DRBD EGFRvIII siRNA or control siRNA. (B) WST-1 cell proliferation analysis of U87MG-EGFRvIII cells treated with PTD-DRBD plus control Luc siRNA or PTD-DRBD with combinatorial EGFR plus control, Akt1, Akt2 or Akt3 siRNAs, as indicated. (C) Detection of apoptotic, TUNEL-positive cells treated with combinatorial PTD-DRBD siRNAs 2 d post-addition by immunofluorescence microscopy (left panel) and by FACS (right panel). (D) Immunoblot analysis of Caspase-3 activation, as indicated.
Figure 9:
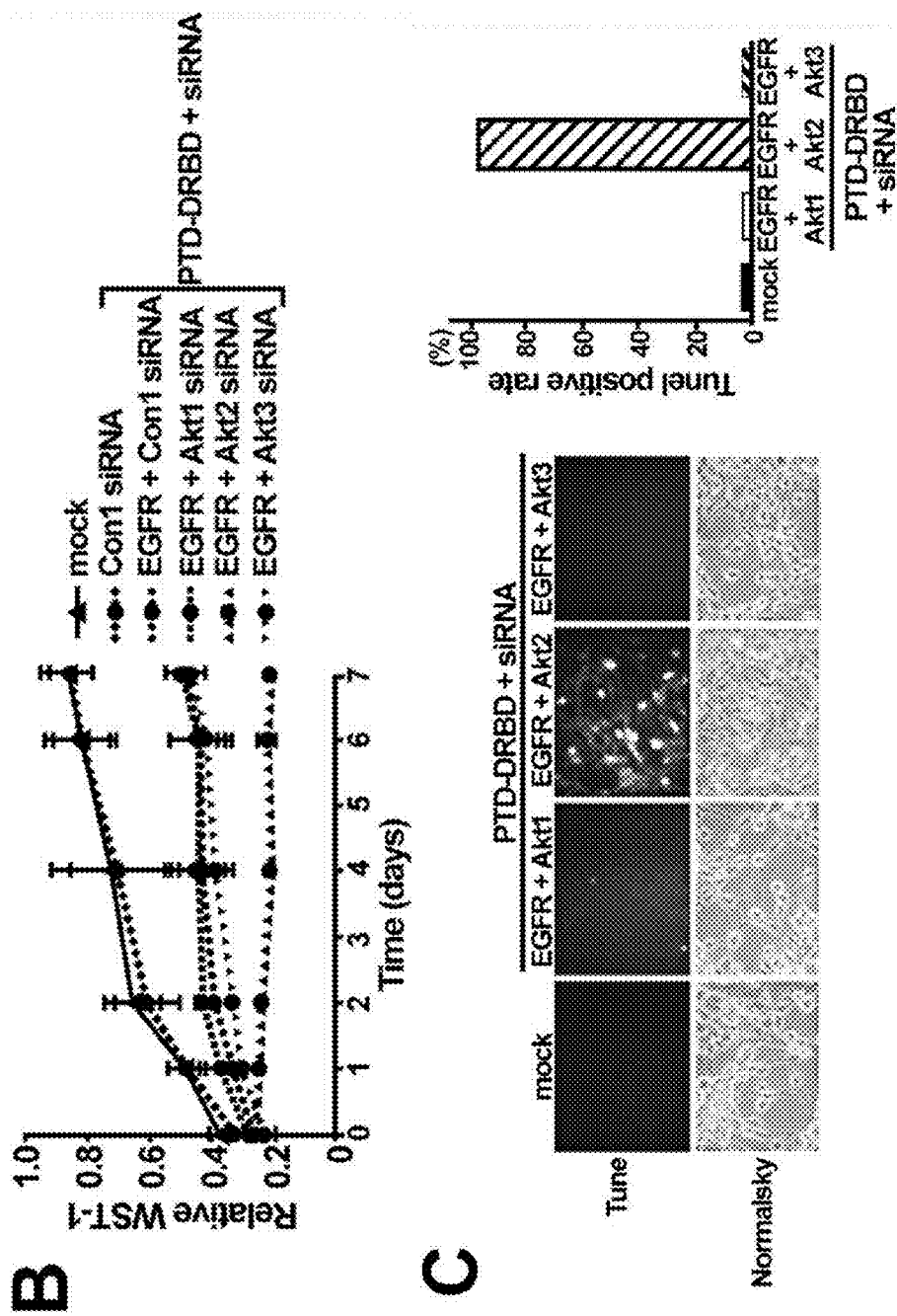
Figure 9:
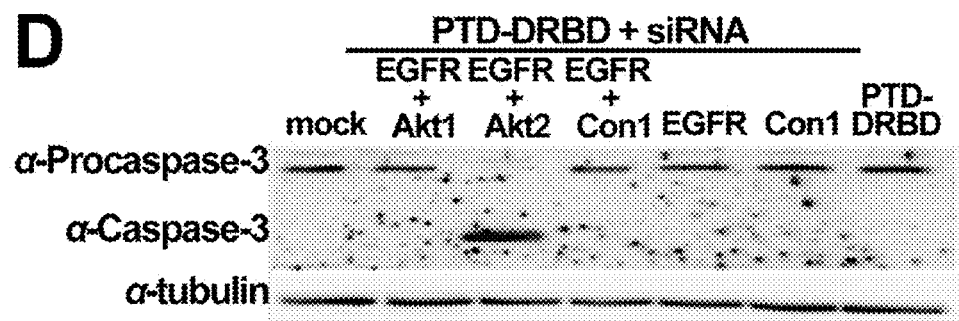
Figure 12:
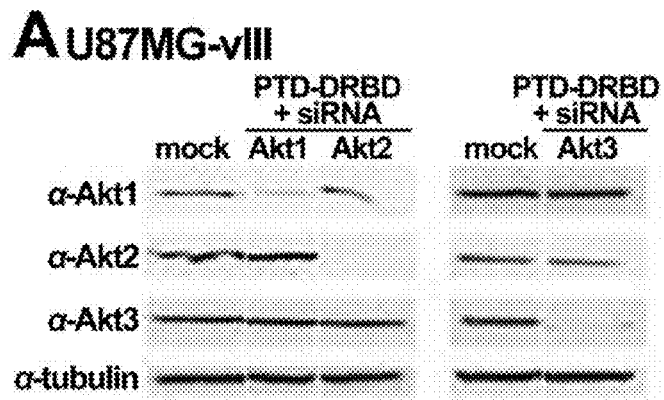
FIG. 12A-E shows additional data related to results of the methods and compositions of the disclosure. (A) Anti-Akt family immunoblot analysis in U87MG-EGFRvIII cells treated with PTD-DRBD plus Akt1, Akt2 or Akt3 siRNAs at 2 d post-addition. Note three left panels taken from same immunoblot exposure, and two right panels take from same immunoblot exposure. (B) Anti-EGFR and anti-Akt family immunoblot analysis in human HFF diploid fibroblasts treated with mock or PTD-DRBD EGFRvIII plus Akt2 siRNAs at 2 d post-addition. (C) Photomicrographs of HFF human diploid fibroblasts treated with mock or PTD-DRBD EGFRvIII plus Akt2 siRNAs at 2 d post-addition. (D) Growth curve of HFF human diploid fibroblasts treated with mock or PTD-DRBD EGFRvIII plus Akt2 siRNAs, as indicated. (E) Flow cytometry cell cycle (propidium iodide) analysis of HFF diploid fibroblasts treated with mock or PTD-DRBD EGFRvIII plus Akt2 siRNAs at 2 d post-addition.
Figure 12:
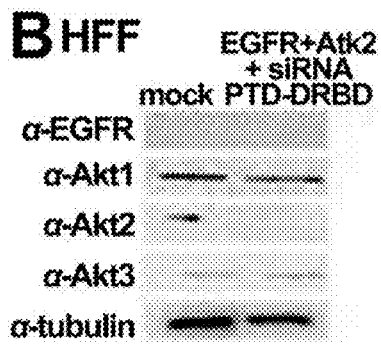
Figure 12:
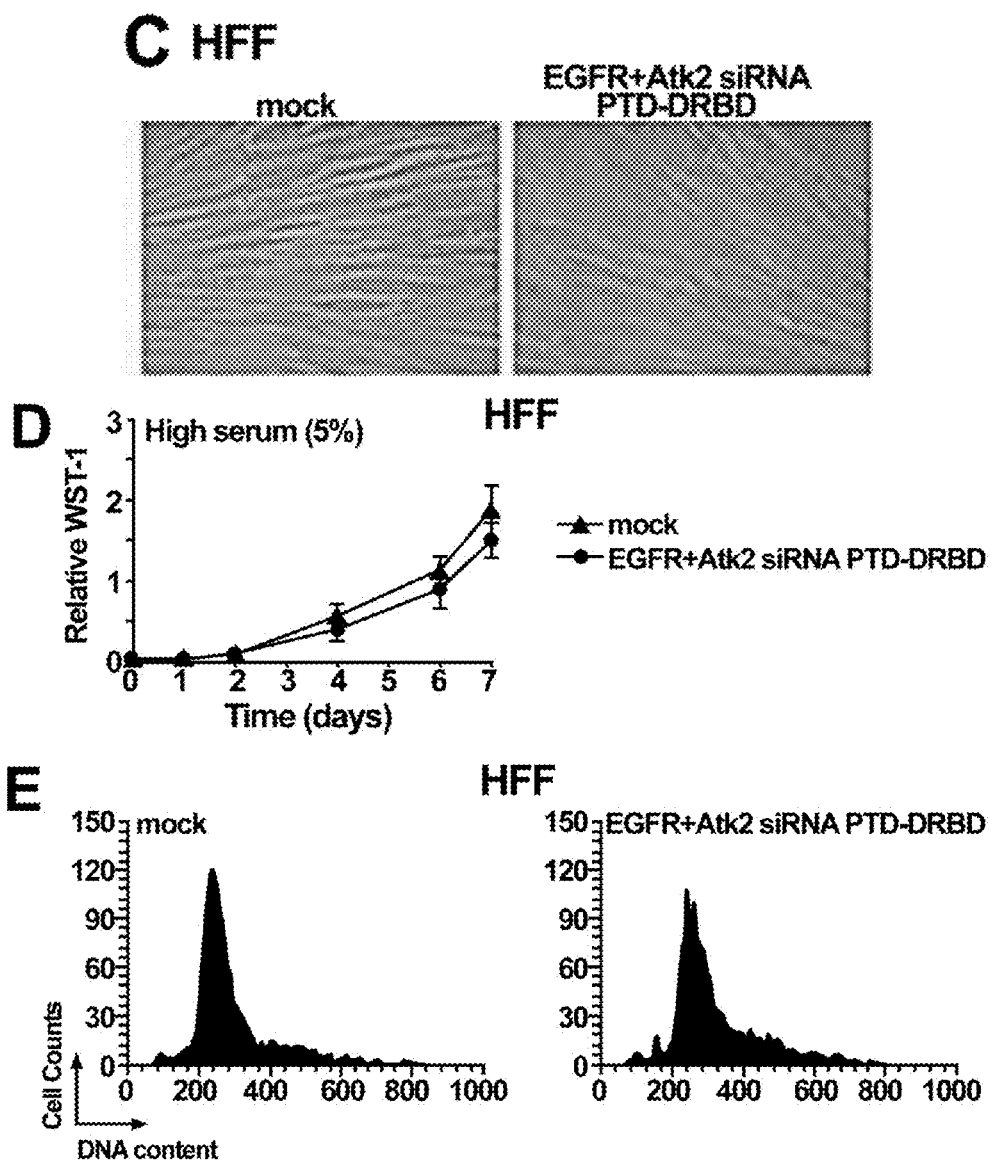

The disclosure advances and improvise the siRNA delivery approach that fuses a dsRNA Binding Domain (DRBD) with a TAT Peptide Transduction Domain (PTD) delivery peptide, termed PTD-DRBD, which is shown to deliver siRNAs into the entire population of cells. PTD-DRBD mediated siRNA delivery into glioblastoma cells resulted in RNAi responses in the entire population in a non-cytotoxic manner (FIG. 8). Treatment of human U87MG glioblastoma cells expressing constitutively active, truncated EGFRvIII, with PTD-DRBD plus EGFR siRNA resulted in an EGFR specific RNAi response, whereas PTD-DRBD delivered control (con1) siRNA did not alter EGFR expression (FIG. 9A). Due to the EGFR protein half-life, a complete EGFR knockdown occurred 2 days post-treatment and the RNAi response began to decay by 6 days. Glioblastomas express all three Akt (-1/-2/-3) family members and PTD-DRBD mediated siRNA delivery also resulted in efficient knockdown of each Akt family member (FIG. 12).

siRNA induced synthetic lethal RNAi responses were tested on glioblastoma cell viability by combinatorial delivery of EGFR plus each Akt family member. Singular PTD-DRBD:siRNA mediated knockdown of EGFR resulted in a moderately decreased proliferative index compared to mock or PTD-DRBD delivered control siRNA (FIG. 9B). Combinatorial knockdown of EGFR plus Akt1 or Akt3 siRNAs resulted in a similar slowing of cell proliferation as EGFR only knockdown. However, PTD-DRBD delivery of EGFR plus Akt2 siRNAs resulted in a substantial decrease in proliferation (FIG. 9B). PTD-DRBD mediated combinatorial siRNA knockdown induced TUNEL-positive and Caspase-3 active apoptotic cells only in PTD-DRBD EGFR plus Akt2 siRNAs treated cells, and not in PTD-DRBD EGFR plus Akt1 or Akt3 siRNA treated cells (FIG. 9C,D). Importantly, PTD-DRBD delivery of EGFR plus Akt2 siRNAs had no detectable effect on dividing human primary fibroblasts (FIG. 12). These observations demonstrate the selective dependency of glioblastoma tumor cell survival on EGFR and Akt2 signaling pathways.

Figure 10:
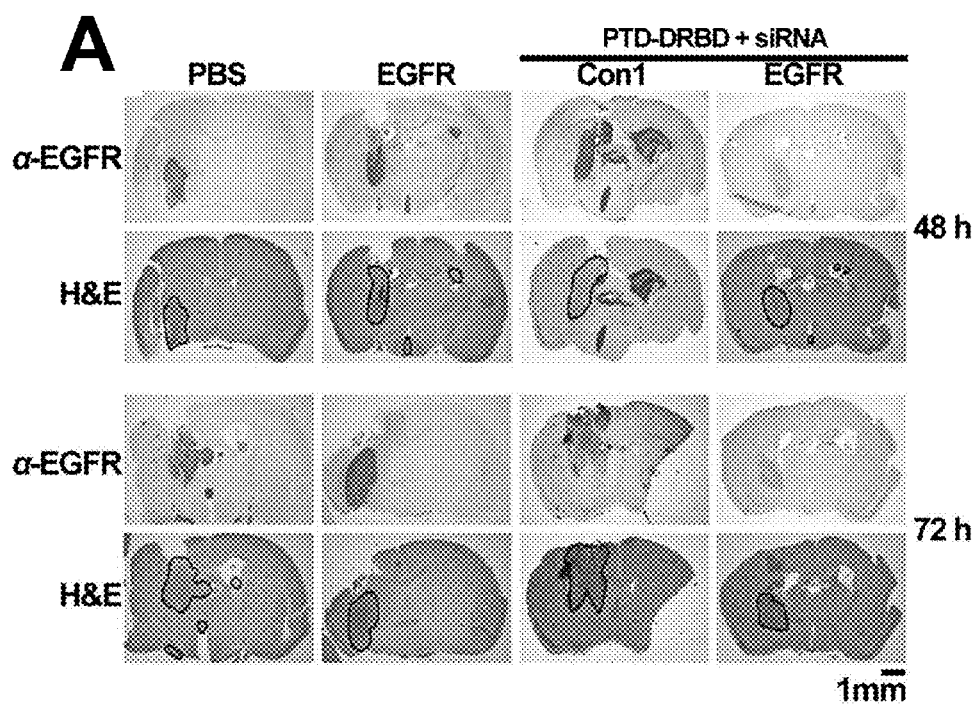
FIG. 10A-B shows in vivo PTD-DRBD mediated EGFR knockdown in glioblastoma mouse models. (A) Nude mice harboring right hemisphere, intracerebral U87MG-EGFRvIII glioblastoma tumors were stereotactically treated on day 7 with PBS, naked EGFR siRNA, PTD-DRBD control siRNA or PTD-DRBD EGFR siRNA. Sequential brain sections were analyzed by H&E and immunohistochemistry for EGFRvIII expression at 48 or 72 h post-administration, as indicated. Outlined area in H&E panels indicates extent of tumor area. (B) High magnification of H&E and anti-EG- FRvIII immunohistochemistry of PTD-DRBD EGFRvIII siRNA or control siRNA treated mice from (A) at 72 h.
Figure 10:
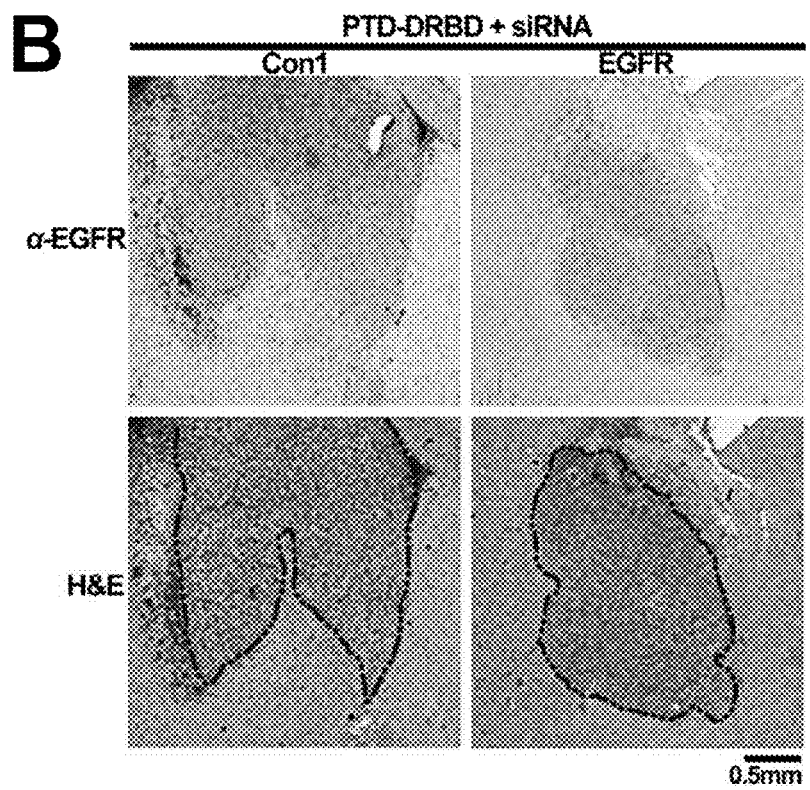
Figure 13:
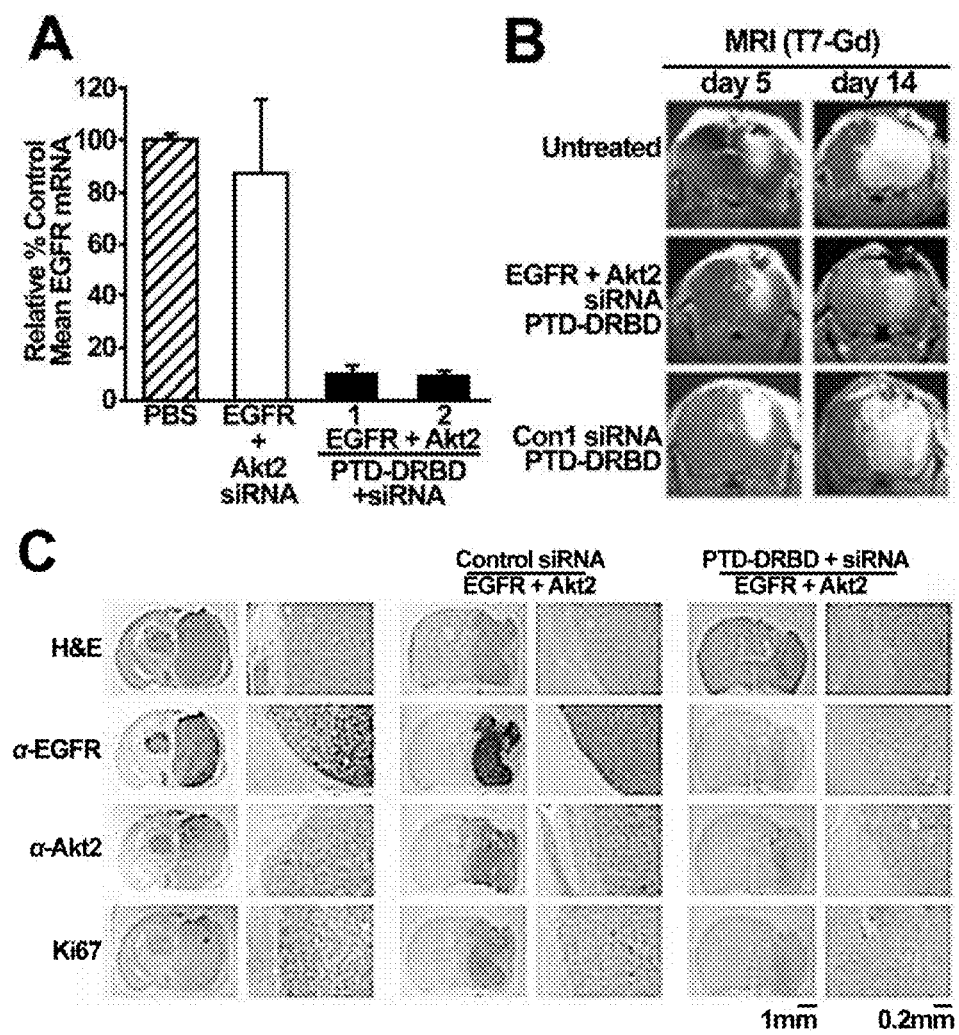
FIG. 13A-C shows additional data related to the methods and compositions of the disclosure. (A) Quantitative TagMan RT-PCR of EGFR mRNA from brain sections of mice treated on 3 and 8 d with PBS, naked EGFR plus Akt2 siRNAs or PTD-DRBD EGFR plus Akt2 siRNAs. mRNA isolated on 10 d. (B) Day 5 and 14 MR images of intracerebral tumor bearing mice untreated or treated on 3, 8, 13 d with PTD-DRBD EGFR plus Akt2 siRNAs or PTD-DRBD plus control siRNAs, as indicated. (C) Anti-EGFR, anti-Akt2, anti-Ki67 immunohistochemistry analysis and H&E staining at 10 d post-inoculation of sequential brain sections from tumor bearing mice treated on 3 and 8 d with PBS, naked EGFR plus Akt2 siRNAs or PTD-DRBD EGFR plus Akt2 siRNAs.

To test the ability of PTD-DRBD mediated siRNA delivery to induce in vivo synthetic lethal RNAi responses, human U87MG-EGFRvIII glioblastoma cells were stereotactically inoculated into the right cerebral hemisphere of mice via insertion of a cranial guide screw (day 0). Mice were stereotactically treated on day 7 and based on the EGFR half-life (FIG. 9A), mice were sacrificed 48 and 72 h post-treatment, sectioned and histologically (H&E) stained (FIG. 10). Treatment with PBS, control naked EGFR siRNA or PTD-DRBD delivered control siRNA did not detectably alter EGFR expression in vivo. In contrast, PTD-DRBD delivery of EGFR siRNA resulted in a substantial EGFR knockdown throughout the tumor at 48 and 72 h post-treatment below the level of detection (FIG. 10) and showed a 10-fold decrease of EGFR mRNA by qRT-PCR (FIG. 13). Combinatorial delivery of EGFR plus Akt2 siRNAs also resulted in loss of detection of EGFR and Akt2 (FIG. 13). MRI imaging of tumor bearing mice treated on days 3, 8, 13 with PTD-DRBD EGFR plus Akt2 siRNAs resulted in a substantial reduction in tumor volume at day 14 compared to both untreated (PBS) control mice or PTD-DRBD control siRNA treated mice (FIG. 11A, B) (FIG. 13). Consistent with tumor volume reduction, extensive apoptotic TUNEL positive cells were detected throughout the tumor in brain sections from PTD-DRBD EGFR plus Akt2 siRNA treated mice (FIG. 11C).

Figure 11:
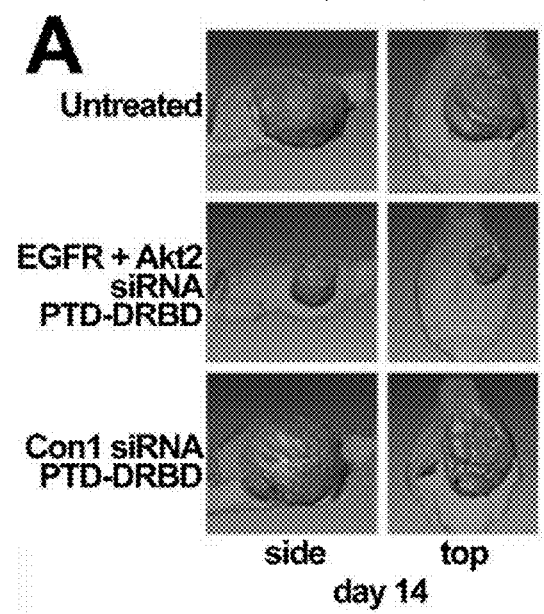
FIG. 11A-D shows in vivo induction of tumor specific synthetic lethal RNAi response. (A) and (B) MRI analysis of tumor bearing mice treated on 3, 8, 13 d with PTD-DRBD EGFRvIII plus Akt2 siRNA or PTD-DRBD plus control siRNA and imaged on 5 and 14 d. Reconstruction 3D MRI image from side and top on day 14 (left panel) and calculated tumor volume (right panel). (C) Fluorescent TUNEL staining of brain sections from at 10 d post-treatment, as indicated. Upper panel, fluorescent confocal microscopy; lower panel, merge of fluorescent and light microscopy. (D) Kaplan-Meier survival curve of right hemisphere, intracerebral glioblastoma tumor bearing mice that were untreated (n=10) or stereotactically treated on 3, 8, 13 d with PBS (n=8), naked EGFR plus Akt2 siRNAs (n=8), PTD-DRBD Akt2 plus control siRNAs (to balance total amount of siRNA) (n=8), PTD-DRBD EGFR plus control siRNAs (n=8), or PTD-DRBD EGFR plus Akt2 siRNAs (n=10), as indicated. Median survival from day 14 to 19 (p<0.001) with PTD-DRBD plus EGFRvIII siRNA and from 14 d to 31.5 d (p<0.0005) with PTD-DRBD EGFRvIII plus Akt2 siRNAs.
Figure 11:
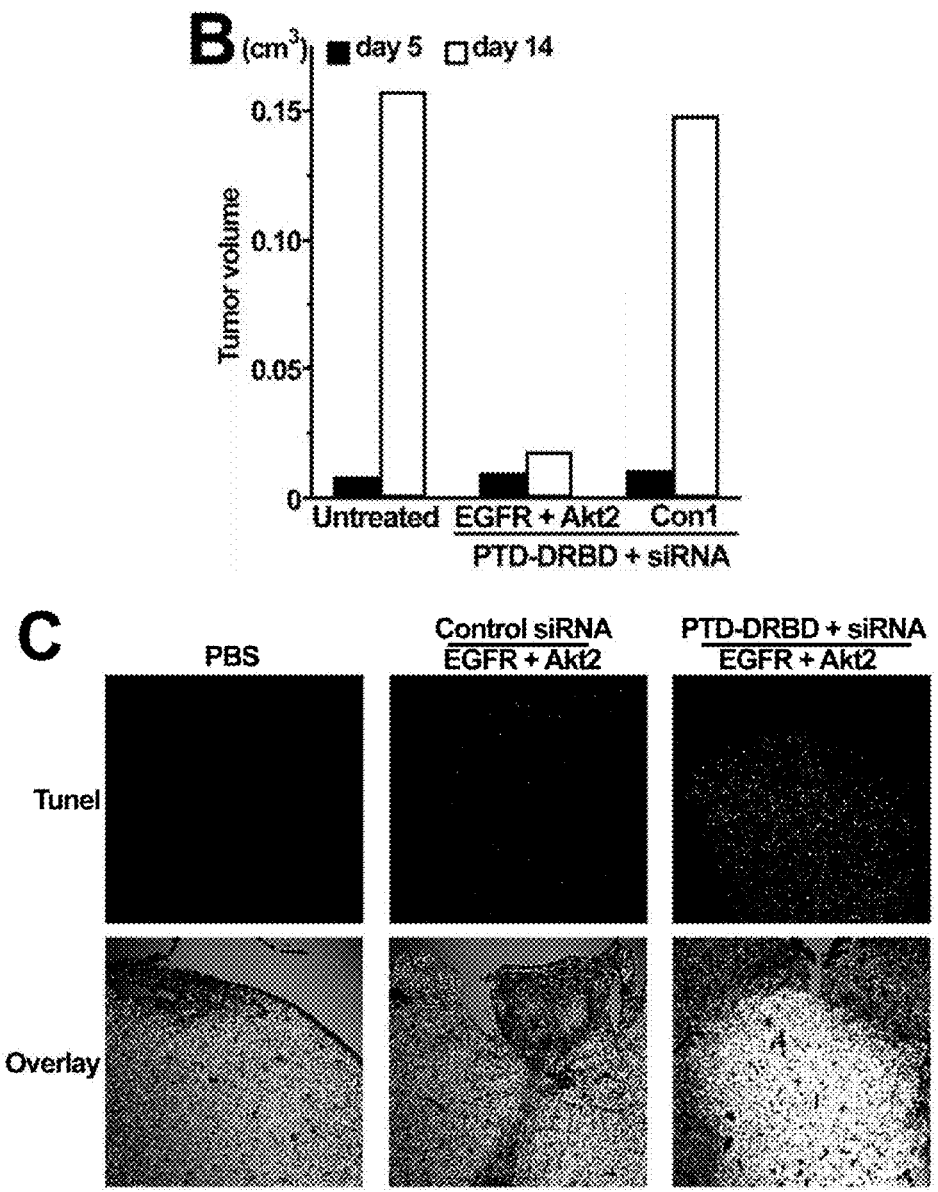
Figure 11:
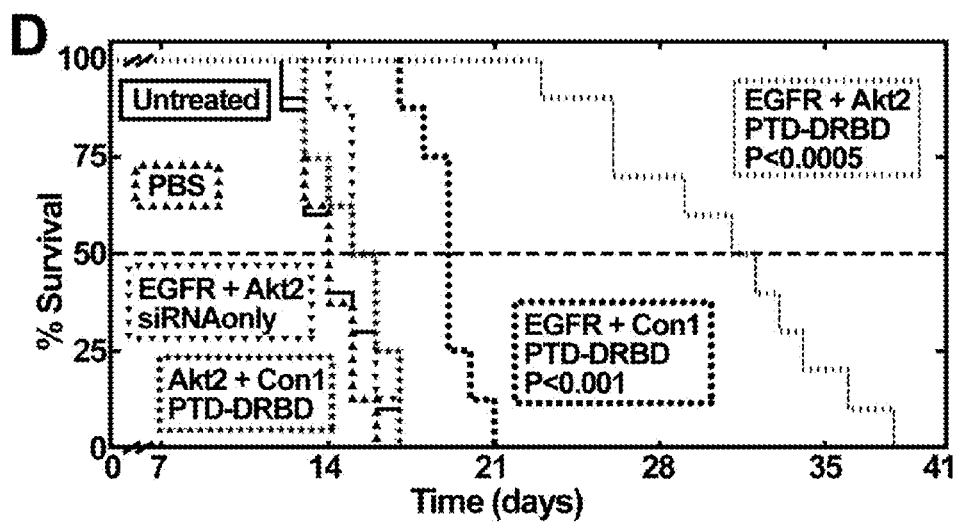

To test the ability of in vivo siRNA induced synthetic lethal RNAi responses to increase longevity, the right cerebral hemisphere of glioblastoma tumor bearing mice were treated on days 3, 8, 13 and assayed for survival (FIG. 11D). Untreated glioblastoma resulted in a rapid onset with a median survival of 14 days (FIG. 11D). PBS (vehicle) or naked EGFR plus Akt2 siRNA treated mice did not show any significant alteration of the survival curve. Surprisingly, PTD-DRBD mediated singular RNAi knockdown of Akt2 did not alter disease outcome. In contrast, PTD-DRBD mediated singular RNAi knockdown of EGFR resulted in a minor, but significant increase in median survival from 14 to 19 days ($p<0.001$) (FIG. 11D). However, PTD-DRBD mediated combinatorial RNAi knockdown of EGFR and Akt2 synergized to significantly increase median survival from 14 to 31.5 days ($p<0.0005$). These observations demonstrate the selective and synthetic lethal effects of combinatorial RNAi to modulate tumor biology in vivo.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A composition comprising a nucleic acid binding polypeptide containing the sequence selected from the group consisting of:
   (a) SEQ ID NO:2, wherein at least 2 histidines are present in the sequence at a position selected from residues selected from the group consisting of 16, 18, 19, 20, 37, 38, 44, 46, 57 and 58;
   (b) SEQ ID NO:3;
   (c) SEQ ID NO:4;
   (d) SEQ ID NO:5; and
   (e) SEQ ID NO:6, wherein the polypeptide is in complex with an anionically charged nucleic acid to form a nucleic acid binding protein-nucleic acid complex having a net cationic charge.

2. A composition of claim 1, further comprising a protein transduction domain (PTD) linked to the anionically charged nucleic acid or the polypeptide.

3. The composition of claim 1, wherein the histidines are immediately adjacent.

4. The composition of claim 1, wherein the histidines are separated by 1, 2 or 3 amino acid residues.

5. The composition of claim 1, wherein the nucleic acid binding protein comprises a plurality of histidines at the C-terminus.

6. The composition of claim 1, wherein the nucleic acid comprises a dsRNA.

7. The composition of claim 2, wherein the PTD is operably linked to the nucleic acid binding polypeptide.

8. The composition of claim 2, wherein the PTD is operably linked to the nucleic acid.

9. The composition of claim 1, wherein the ratio of nucleic acid binding polypeptide to nucleic acid is 1:1.

10. The composition of claim 1, wherein the ratio of nucleic acid binding polypeptide to nucleic acid is 2:1.

11. The composition of claim 2, wherein the protein transduction moiety is selected from the group consisting of a polypeptide comprising a herpesviral VP22 protein; a polypeptide comprising a human immunodeficiency virus (HIV) TAT protein; a polypeptide comprising a homeodomain of an Antennapedia protein (Antp HD), and functional fragments thereof.

12. The composition of claim 2, wherein the protein transduction domain is operably linked to at least 1 nucleic acid binding polypeptide.

* * * * *

SEQUENCE LISTING

```
<160> NUMBER OF SEQ ID NOS: 22

<210> SEQ ID NO 1
<211> LENGTH: 70
<212> TYPE: PRT
<213> ORGANISM: Artificial Sequence
<220> FEATURE:
<223> OTHER INFORMATION: RNA Binding Peptide Consensus Sequence
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is F or Y
<220> FEATURE:
<221> NAME/KEY: MISC_FEATURE
<222> LOCATION: (3)..(5)
<223> OTHER INFORMATION: Xaa is any amino acid
<220> FEATURE:
<221> NAME/KEY: MISC_FEATURE
```

```
<222> LOCATION: (6)..(6)
<223> OTHER INFORMATION: Xaa is L or I
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Y or I
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (13)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is V or L
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is V or L
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (20)..(25)
<223> OTHER INFORMATION: Xaa is any amino acid
<220> FEATURE:
<221> NAME/KEY: MISC_FEATURE
<222> LOCATION: (27)..(32)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is any amino acid
<220> FEATURE:
<221> NAME/KEY: MISC_FEATURE
<222> LOCATION: (35)..(35)
<223> OTHER INFORMATION: Xaa is F or Y
<220> FEATURE:
<221> NAME/KEY: MISC_FEATURE
<222> LOCATION: (36)..(38)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is I or M
<220> FEATURE:
<221> NAME/KEY: MISC_FEATURE
<222> LOCATION: (40)..(41)
<223> OTHER INFORMATION: Xaa is any amino acid
<220> FEATURE:
<221> NAME/KEY: MISC_FEATURE
<222> LOCATION: (42)..(42)
<223> OTHER INFORMATION: Xaa is R or K
<220> FEATURE:
<221> NAME/KEY: MISC_FEATURE
<222> LOCATION: (44)..(44)
<223> OTHER INFORMATION: Xaa is F or Y
<220> FEATURE:
<221> NAME/KEY: MISC_FEATURE
<222> LOCATION: (45)..(46)
<223> OTHER INFORMATION: Xaa is any amino acid
<220> FEATURE:
<221> NAME/KEY: MISC_FEATURE
<222> LOCATION: (48)..(48)
<223> OTHER INFORMATION: Xaa is any amino acid
<220> FEATURE:
```

```
<221> NAME/KEY: MISC_FEATURE
<222> LOCATION: (50)..(50)
<223> OTHER INFORMATION: Xaa is any amino acid
<220> FEATURE:
<221> NAME/KEY: MISC_FEATURE
<222> LOCATION: (51)..(51)
<223> OTHER INFORMATION: Xaa is S or T
<220> FEATURE:
<221> NAME/KEY: MISC_FEATURE
<222> LOCATION: (53)..(53)
<223> OTHER INFORMATION: Xaa is any amino acid
<220> FEATURE:
<221> NAME/KEY: MISC_FEATURE
<222> LOCATION: (57)..(57)
<223> OTHER INFORMATION: Xaa is N or Q
<220> FEATURE:
<221> NAME/KEY: MISC_FEATURE
<222> LOCATION: (58)..(58)
<223> OTHER INFORMATION: Xaa is any amino acid
<220> FEATURE:
<221> NAME/KEY: MISC_FEATURE
<222> LOCATION: (64)..(64)
<223> OTHER INFORMATION: Xaa is V or Y
<220> FEATURE:
<221> NAME/KEY: MISC_FEATURE
<222> LOCATION: (65)..(66)
<223> OTHER INFORMATION: Xaa is any amino acid
<220> FEATURE:
<221> NAME/KEY: MISC_FEATURE
<222> LOCATION: (67)..(67)
<223> OTHER INFORMATION: Xaa is L or I
<220> FEATURE:
<221> NAME/KEY: MISC_FEATURE
<222> LOCATION: (68)..(69)
<223> OTHER INFORMATION: Xaa is any amino acid

<400> SEQUENCE: 1

Xaa Xaa Xaa Xaa Xaa Xaa Asn Xaa Xaa Xaa Gln Lys Xaa Xaa Xaa
1               5                   10                  15

Xaa Xaa Tyr Xaa Xaa Xaa Xaa Xaa Gly Xaa Xaa Xaa Xaa Xaa Xaa
            20                  25                  30

Phe Xaa Xaa Xaa Xaa Xaa Xaa Xaa Xaa Glu Xaa Xaa Xaa Xaa Gly Xaa
        35                  40                  45

Gly Xaa Xaa Lys Xaa Glu Ala Lys Xaa Xaa Ala Ala Lys Leu Ala Xaa
    50                  55                  60

Xaa Xaa Xaa Xaa Xaa Glu
65                  70

<210> SEQ ID NO 2
<211> LENGTH: 70
<212> TYPE: PRT
<213> ORGANISM: Artificial Sequence
<220> FEATURE:
<223> OTHER INFORMATION: RNA binding peptide fragment

<400> SEQUENCE: 2

Phe Phe Met Glu Glu Leu Asn Thr Tyr Arg Gln Lys Gln Gly Val Val
1               5                   10                  15

Leu Lys Tyr Gln Glu Leu Pro Asn Ser Gly Pro Pro His Asp Arg Arg
            20                  25                  30

Phe Thr Phe Gln Val Ile Ile Asp Gly Arg Glu Phe Pro Glu Gly Glu
        35                  40                  45

Gly Arg Ser Lys Lys Glu Ala Lys Asn Ala Ala Ala Lys Leu Ala Val
    50                  55                  60

Glu Ile Leu Asn Lys Glu
65                  70
```

```
<210> SEQ ID NO 3
<211> LENGTH: 70
<212> TYPE: PRT
<213> ORGANISM: Artificial Sequence
<220> FEATURE:
<223> OTHER INFORMATION: RNA Binding Peptide Fragment

<400> SEQUENCE: 3

Phe Phe Met Glu Glu Leu Asn Thr Tyr Arg Gln Lys Gln Gly Val His
1               5                   10                  15

Leu His Tyr Gln Glu Leu Pro Asn Ser Gly Pro Pro His Asp Arg Arg
            20                  25                  30

Phe Thr Phe Gln Val Ile Ile Asp Gly Arg Glu Phe Pro Glu Gly Glu
        35                  40                  45

Gly Arg Ser Lys Lys Glu Ala Lys Asn Ala Ala Ala Lys Leu Ala Val
    50                  55                  60

Glu Ile Leu Asn Lys Glu
65                  70

<210> SEQ ID NO 4
<211> LENGTH: 82
<212> TYPE: PRT
<213> ORGANISM: Artificial Sequence
<220> FEATURE:
<223> OTHER INFORMATION: RNA Binding Peptide

<400> SEQUENCE: 4

Phe Phe Met Glu Glu Leu Asn Thr Tyr Arg Gln Lys Gln Gly Val Val
1               5                   10                  15

Leu Lys Tyr Gln Glu Leu Pro Asn Ser Gly Pro Pro His Asp Arg Arg
            20                  25                  30

Phe Thr Phe Gln Val Ile Ile Asp Gly Arg Glu Phe Pro Glu Gly Glu
        35                  40                  45

Gly Arg Ser Lys Lys Glu Ala Lys Asn Ala Ala Ala Lys Leu Ala Val
    50                  55                  60

Glu Ile Leu Asn Lys Glu His His His His His His His His
65                  70                  75                  80

His His

<210> SEQ ID NO 5
<211> LENGTH: 70
<212> TYPE: PRT
<213> ORGANISM: Artificial Sequence
<220> FEATURE:
<223> OTHER INFORMATION: RNA Binding Peptide

<400> SEQUENCE: 5

Phe Phe Met Glu Glu Leu Asn Thr Tyr Arg Gln Lys Gln Gly Val Val
1               5                   10                  15

Leu Lys Tyr Gln Glu Leu Pro Asn Ser Gly Pro Pro His Asp Arg Arg
            20                  25                  30

Phe Thr Phe Gln Val Ile Ile Asp Gly Arg Glu His Pro His Gly Glu
        35                  40                  45

Gly Arg Ser Lys Lys Glu Ala Lys Asn Ala Ala Ala Lys Leu Ala Val
    50                  55                  60

Glu Ile Leu Asn Lys Glu
65                  70

<210> SEQ ID NO 6
<211> LENGTH: 70
```

```
<212> TYPE: PRT
<213> ORGANISM: Artificial Sequence
<220> FEATURE:
<223> OTHER INFORMATION: RNA Binding Peptide

<400> SEQUENCE: 6

Phe Phe Met Glu Glu Leu Asn Thr Tyr Arg Gln Lys Gln Gly Val Val
1               5                   10                  15

Leu Lys Tyr Gln Glu Leu Pro Asn Ser Gly Pro Pro His Asp Arg Arg
            20                  25                  30

Phe Thr Phe Gln Val Ile Ile Asp Gly Arg Glu Phe Pro Glu Gly Glu
        35                  40                  45

Gly Arg Ser Lys Lys Glu Ala Lys His His Ala Ala Lys Leu Ala Val
50                  55                  60

Glu Ile Leu Asn Lys Glu
65                  70

<210> SEQ ID NO 7
<211> LENGTH: 551
<212> TYPE: PRT
<213> ORGANISM: Homo sapiens

<400> SEQUENCE: 7

Met Ala Gly Asp Leu Ser Ala Gly Phe Phe Met Glu Glu Leu Asn Thr
1               5                   10                  15

Tyr Arg Gln Lys Gln Gly Val Val Leu Lys Tyr Gln Glu Leu Pro Asn
            20                  25                  30

Ser Gly Pro Pro His Asp Arg Arg Phe Thr Phe Gln Val Ile Ile Asp
        35                  40                  45

Gly Arg Glu Phe Pro Glu Gly Glu Gly Arg Ser Lys Lys Glu Ala Lys
50                  55                  60

Asn Ala Ala Ala Lys Leu Ala Val Glu Ile Leu Asn Lys Glu Lys Lys
65                  70                  75                  80

Ala Val Ser Pro Leu Leu Leu Thr Thr Thr Asn Ser Ser Glu Gly Leu
                85                  90                  95

Ser Met Gly Asn Tyr Ile Gly Leu Ile Asn Arg Ile Ala Gln Lys Lys
            100                 105                 110

Arg Leu Thr Val Asn Tyr Glu Gln Cys Ala Ser Gly Val His Gly Pro
        115                 120                 125

Glu Gly Phe His Tyr Lys Cys Lys Met Gly Gln Lys Glu Tyr Ser Ile
130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr Thr Cys Glu Ser Gln Ser Asn Ser
            180                 185                 190

Leu Val Thr Ser Thr Leu Ala Ser Glu Ser Ser Glu Gly Asp Phe
        195                 200                 205

Ser Ala Asp Thr Ser Glu Ile Asn Ser Asn Ser Asp Ser Leu Asn Ser
210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Phe Gly Met Asp Phe Lys Glu Ile Glu Leu
```

```
            260                 265                 270
Ile Gly Ser Gly Gly Phe Gly Gln Val Phe Lys Ala Lys His Arg Ile
        275                 280                 285

Asp Gly Lys Thr Tyr Val Ile Lys Arg Val Lys Tyr Asn Asn Glu Lys
    290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
                325                 330                 335

Ser Asp Asp Ser Leu Glu Ser Ser Asp Tyr Asp Pro Glu Asn Ser Lys
            340                 345                 350

Asn Ser Ser Arg Ser Lys Thr Lys Cys Leu Phe Ile Gln Met Glu Phe
        355                 360                 365

Cys Asp Lys Gly Thr Leu Glu Gln Trp Ile Glu Lys Arg Arg Gly Glu
    370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                405                 410                 415

Pro Ser Asn Ile Phe Leu Val Asp Thr Lys Gln Val Lys Ile Gly Asp
            420                 425                 430

Phe Gly Leu Val Thr Ser Leu Lys Asn Asp Gly Lys Arg Thr Arg Ser
        435                 440                 445

Lys Gly Thr Leu Arg Tyr Met Ser Pro Glu Gln Ile Ser Ser Gln Asp
    450                 455                 460

Tyr Gly Lys Glu Val Asp Leu Tyr Ala Leu Gly Leu Ile Leu Ala Glu
465                 470                 475                 480

Leu Leu His Val Cys Asp Thr Ala Phe Glu Thr Ser Lys Phe Phe Thr
                485                 490                 495

Asp Leu Arg Asp Gly Ile Ile Ser Asp Ile Phe Asp Lys Lys Glu Lys
            500                 505                 510

Thr Leu Leu Gln Lys Leu Leu Ser Lys Lys Pro Glu Asp Arg Pro Asn
        515                 520                 525

Thr Ser Glu Ile Leu Arg Thr Leu Thr Val Trp Lys Lys Ser Pro Glu
    530                 535                 540

Lys Asn Glu Arg His Thr Cys
545                 550

<210> SEQ ID NO 8
<211> LENGTH: 8
<212> TYPE: PRT
<213> ORGANISM: Artificial Sequence
<220> FEATURE:
<223> OTHER INFORMATION: Protein Transduction Domain Consensus Sequence
<220> FEATURE:
<221> NAME/KEY: MISC_FEATURE
<222> LOCATION: (1)..(1)
<223> OTHER INFORMATION: Xaa is a basic amino acid
<220> FEATURE:
<221> NAME/KEY: MISC_FEATURE
<222> LOCATION: (2)..(4)
<223> OTHER INFORMATION: Xaa is an alpha-helix enhacing amino acid
<220> FEATURE:
<221> NAME/KEY: MISC_FEATURE
<222> LOCATION: (5)..(5)
<223> OTHER INFORMATION: Xaa is a basic amino acid
<220> FEATURE:
<221> NAME/KEY: MISC_FEATURE
<222> LOCATION: (6)..(7)
<223> OTHER INFORMATION: Xaa is an alpha-helix enhancing amino acid
```

<220> FEATURE:
<221> NAME/KEY: MISC_FEATURE
<222> LOCATION: (8)..(8)
<223> OTHER INFORMATION: Xaa is a basic amino acid

<400> SEQUENCE: 8

Xaa Xaa Xaa Xaa Xaa Xaa Xaa Xaa
1               5

<210> SEQ ID NO 9
<211> LENGTH: 8
<212> TYPE: PRT
<213> ORGANISM: Artificial Sequence
<220> FEATURE:
<223> OTHER INFORMATION: Protein Transduction Domain Consensus Sequence
<220> FEATURE:
<221> NAME/KEY: MISC_FEATURE
<222> LOCATION: (1)..(1)
<223> OTHER INFORMATION: Xaa is a basic amino acid
<220> FEATURE:
<221> NAME/KEY: MISC_FEATURE
<222> LOCATION: (2)..(3)
<223> OTHER INFORMATION: Xaa is an alpha-helix
<220> FEATURE:
<221> NAME/KEY: MISC_FEATURE
<222> LOCATION: (4)..(5)
<223> OTHER INFORMATION: Xaa is basic amino acid
<220> FEATURE:
<221> NAME/KEY: MISC_FEATURE
<222> LOCATION: (6)..(7)
<223> OTHER INFORMATION: Xaa is an alpha-helix enhancing amino acid
<220> FEATURE:
<221> NAME/KEY: MISC_FEATURE
<222> LOCATION: (8)..(8)
<223> OTHER INFORMATION: Xaa is a basic amino acid

<400> SEQUENCE: 9

Xaa Xaa Xaa Xaa Xaa Xaa Xaa Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Protein Transduction Domain

<400> SEQUENCE: 10

Lys Lys Arg Pro Lys Pro Gly
1               5

<210> SEQ ID NO 11
<211> LENGTH: 11
<212> TYPE: PRT
<213> ORGANISM: Artificial Sequence
<220> FEATURE:
<223> OTHER INFORMATION: Protein Transduction Domain Consensus Sequence
<220> FEATURE:
<221> NAME/KEY: MISC_FEATURE
<222> LOCATION: (1)..(2)
<223> OTHER INFORMATION: Xaa is an alpha-helical enhancing amino acid
<220> FEATURE:
<221> NAME/KEY: MISC_FEATURE
<222> LOCATION: (4)..(4)
<223> OTHER INFORMATION: Xaa is an alpha-helical enhancing amino acid
<220> FEATURE:
<221> NAME/KEY: MISC_FEATURE
<222> LOCATION: (5)..(5)
<223> OTHER INFORMATION: Xaa is P or an alpha-helical enhancing amino acid
<220> FEATURE:
<221> NAME/KEY: MISC_FEATURE
<222> LOCATION: (6)..(6)

```
<223> OTHER INFORMATION: Xaa is a basic amino acid or an alpha-helical
      enhancing amino acid
<220> FEATURE:
<221> NAME/KEY: MISC_FEATURE
<222> LOCATION: (7)..(7)
<223> OTHER INFORMATION: Xaa is a basic amino acid
<220> FEATURE:
<221> NAME/KEY: MISC_FEATURE
<222> LOCATION: (8)..(8)
<223> OTHER INFORMATION: Xaa is proline or an alpha-helical enhancing
      amino acid
<220> FEATURE:
<221> NAME/KEY: MISC_FEATURE
<222> LOCATION: (9)..(9)
<223> OTHER INFORMATION: Xaa is an alpha-helical enhancing amino acid
<220> FEATURE:
<221> NAME/KEY: MISC_FEATURE
<222> LOCATION: (10)..(10)
<223> OTHER INFORMATION: Xaa is a basic amino acid
<220> FEATURE:
<221> NAME/KEY: MISC_FEATURE
<222> LOCATION: (11)..(11)
<223> OTHER INFORMATION: Xaa is a basic amino acid or an alpha-helical
      enhancing amino acid

<400> SEQUENCE: 11

Xaa Xaa Arg Xaa Xaa Xaa Xaa Xaa Xaa Xaa Xaa
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Protein Transduction Domain Consensus Sequence
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid

<400> SEQUENCE: 12

Lys Xaa Arg Xaa Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Protein Transduction Domain

<400> SEQUENCE: 13

Arg Lys Lys Arg Arg Gln Arg Arg Arg
1               5

<210> SEQ ID NO 14
<211> LENGTH: 86
<212> TYPE: PRT
<213> ORGANISM: Human immunodeficiency virus

<400> SEQUENCE: 14

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
```

-continued

```
                35                  40                  45
Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 15
<211> LENGTH: 15
<212> TYPE: PRT
<213> ORGANISM: Artificial Sequence
<220> FEATURE:
<223> OTHER INFORMATION: Protamine fragment

<400> SEQUENCE: 15

Arg Ser Arg Arg Arg Arg Arg Ser Cys Gln Thr Arg Arg Arg
1               5                  10                  15

<210> SEQ ID NO 16
<211> LENGTH: 5
<212> TYPE: PRT
<213> ORGANISM: Artificial Sequence
<220> FEATURE:
<223> OTHER INFORMATION: Peptide Linker

<400> SEQUENCE: 16

Gly Gly Gly Gly Ser
1               5

<210> SEQ ID NO 17
<211> LENGTH: 12
<212> TYPE: PRT
<213> ORGANISM: Artificial Sequence
<220> FEATURE:
<223> OTHER INFORMATION: Peptide Linker

<400> SEQUENCE: 17

Gly Lys Ser Ser Gly Ser Gly Ser Glu Ser Lys Ser
1               5                  10

<210> SEQ ID NO 18
<211> LENGTH: 14
<212> TYPE: PRT
<213> ORGANISM: Artificial Sequence
<220> FEATURE:
<223> OTHER INFORMATION: Peptide Linker

<400> SEQUENCE: 18

Gly Ser Thr Ser Gly Ser Gly Lys Ser Ser Glu Gly Lys Gly
1               5                  10

<210> SEQ ID NO 19
<211> LENGTH: 18
<212> TYPE: PRT
<213> ORGANISM: Artificial Sequence
<220> FEATURE:
<223> OTHER INFORMATION: Peptide Linker

<400> SEQUENCE: 19

Gly Ser Thr Ser Gly Ser Gly Lys Ser Ser Glu Gly Ser Gly Ser Thr
1               5                  10                  15

Lys Gly
```

```
<210> SEQ ID NO 20
<211> LENGTH: 18
<212> TYPE: PRT
<213> ORGANISM: Artificial Sequence
<220> FEATURE:
<223> OTHER INFORMATION: Peptide Linker

<400> SEQUENCE: 20

Gly Ser Thr Ser Gly Ser Gly Lys Pro Gly Ser Gly Glu Gly Ser Thr
1               5                   10                  15

Lys Gly

<210> SEQ ID NO 21
<211> LENGTH: 14
<212> TYPE: PRT
<213> ORGANISM: Artificial Sequence
<220> FEATURE:
<223> OTHER INFORMATION: Peptide Linker

<400> SEQUENCE: 21

Glu Gly Lys Ser Ser Gly Ser Gly Ser Glu Ser Lys Glu Phe
1               5                   10

<210> SEQ ID NO 22
<211> LENGTH: 142
<212> TYPE: PRT
<213> ORGANISM: Artificial Sequence
<220> FEATURE:
<223> OTHER INFORMATION: Fusion protein construct

<400> SEQUENCE: 22

Met Gly Arg Lys Lys Arg Arg Gln Arg Arg Gly His Ser Gly Arg
1               5                   10                  15

Lys Lys Arg Arg Gln Arg Arg Gly His Ile Tyr Pro Tyr Asp Val
                20                  25                  30

Pro Asp Tyr Ala Gly Asp Pro Gly Arg Lys Lys Arg Arg Gln Arg Arg
                35                  40                  45

Arg Gly Asp Pro Ala Gly Asp Leu Ser Ala Gly Phe Phe Met Glu Glu
        50                  55                  60

Leu Asn Thr Tyr Arg Gln Lys Gln Gly Val Val Leu Tyr Gln Glu
65                  70                  75                  80

Leu Pro Asn Ser Gly Pro Pro His Asp Arg Arg Phe Thr Phe Gln Val
                85                  90                  95

Ile Ile Asp Gly Arg Glu Phe Pro Glu Gly Glu Gly Arg Ser Lys Lys
                100                 105                 110

Glu Ala Lys Asn Ala Ala Ala Lys Leu Ala Val Glu Ile Leu Asn Lys
            115                 120                 125

Glu Lys Lys Ala Ala Ala Leu Glu His His His His His
            130                 135                 140
```